United States Patent [19]
Hill et al.

[11] Patent Number: 5,923,015
[45] Date of Patent: Jul. 13, 1999

[54] EMBOSSED CARD PACKAGE PRODUCTION SYSTEM WITH MODULAR INSERTERS FOR MULTIPLE FORMS AND CARD VERIFICATION APPARATUS

[75] Inventors: Jeffery L. Hill, Mundelein; Gregory S. Hill, Lake Zurich, both of Ill.; Robert J. Bretl, Menominee, Mich.; Fred J. Kassabian, Arlington Heights, Ill.

[73] Assignee: Dynetics Engineering Corporation, Lincolnshire, Ill.

[21] Appl. No.: 08/647,158

[22] Filed: May 9, 1996

Related U.S. Application Data

[62] Division of application No. 08/340,268, Nov. 15, 1994, which is a division of application No. 08/036,664, Mar. 24, 1993, Pat. No. 5,388,815, which is a continuation-in-part of application No. 08/019,865, Feb. 19, 1993, abandoned.

[51] Int. Cl.⁶ .................................................. G06K 5/00
[52] U.S. Cl. ........................... 235/380; 235/375; 235/486
[58] Field of Search .................................... 235/380, 462, 235/385, 470, 435, 440, 462.01, 486, 375

[56] References Cited

U.S. PATENT DOCUMENTS

| 3,861,299 | 1/1975 | Drillick ..................................... 101/18 |
| 4,034,210 | 7/1977 | Hill et al. ................................ 235/487 |
| 4,088,216 | 5/1978 | LaManna et al. ....................... 400/130 |
| 4,194,685 | 3/1980 | Hill et al. ............................. 235/375 X |
| 4,271,012 | 6/1981 | LaManna et al. ....................... 209/653 |
| 4,349,741 | 9/1982 | Bobart et al. ......................... 235/462 X |
| 4,384,196 | 5/1983 | McCumber et al. ..................... 235/375 |
| 4,384,711 | 5/1983 | Gabel et al. ............................. 271/129 |
| 4,420,819 | 12/1983 | Price et al. .............................. 364/900 |
| 4,429,217 | 1/1984 | Hill et al. ................................ 235/380 |
| 4,541,337 | 9/1985 | Schaul ..................................... 101/227 |
| 4,686,898 | 8/1987 | LaManna et al. ......................... 101/18 |
| 4,688,785 | 8/1987 | Nubson et al. .......................... 271/266 |
| 4,755,069 | 7/1988 | LaManna et al. ....................... 400/130 |
| 4,784,059 | 11/1988 | LaManna et al. ......................... 101/18 |
| 4,789,420 | 12/1988 | LaManna et al. ....................... 156/540 |
| 4,866,545 | 9/1989 | LaManna et al. .................. 235/437 X |
| 4,900,168 | 2/1990 | LaManna et al. ....................... 400/130 |
| 4,969,760 | 11/1990 | LaManna et al. ....................... 400/134 |
| 5,151,582 | 9/1992 | Fujioka ................................... 235/469 |
| 5,426,283 | 6/1995 | Berthozat et al. ...................... 235/380 |
| 5,494,544 | 2/1996 | Hill et al. ............................. 235/437 X |

Primary Examiner—Michael G. Lee
Attorney, Agent, or Firm—James W. Potthast

[57] ABSTRACT

A card package production system (10) with interchangeable inserters (24A, 24B) and carrier folders 86B) to enable use of forms (26A, 26B) of different types verifies the carriers (30) if they are properly produced and rejects them if they are not prior to the attachment to a carrier. The embossed characters and encoding read from the card are compared with the stored card data to verify accuracy and are compared to coding on the carrier form (26A, 26B) to determine if there is a match. A code on the carrier is also compared to stored carrier data and to the cards provided for insertion and are rejected without cards if incorrectly prepared.

4 Claims, 13 Drawing Sheets

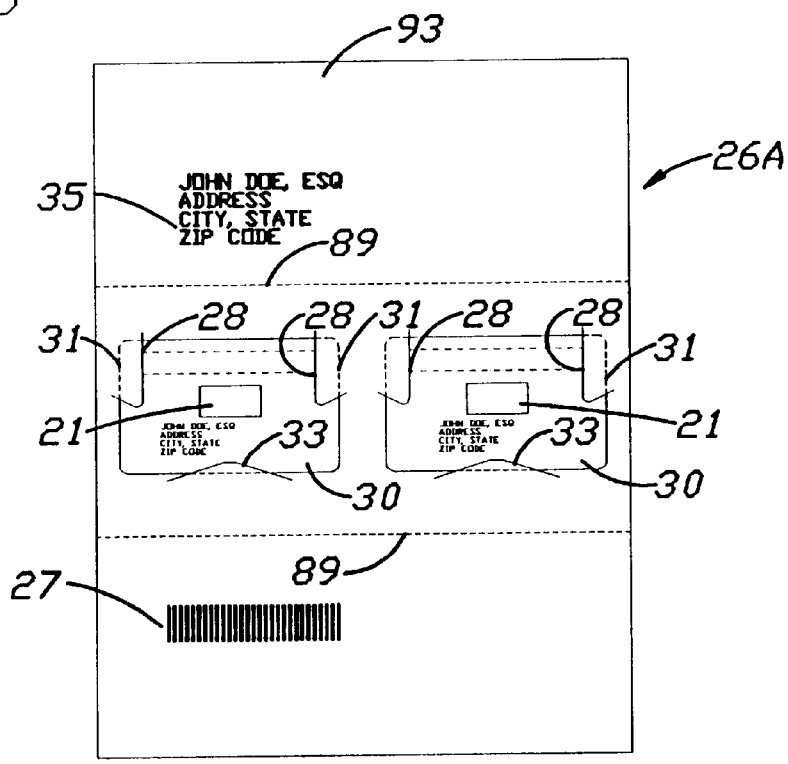
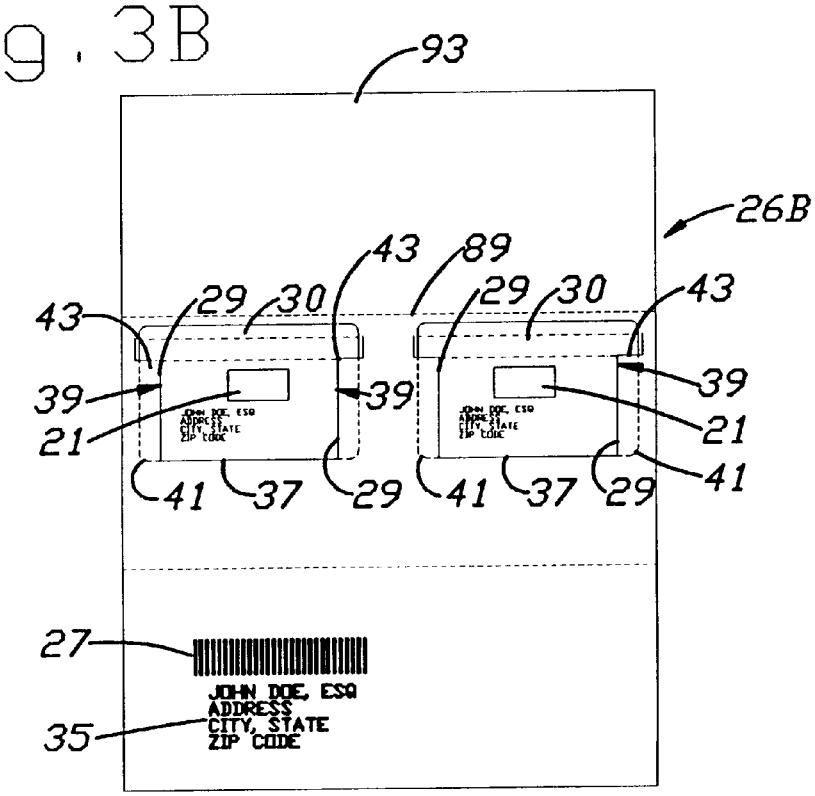

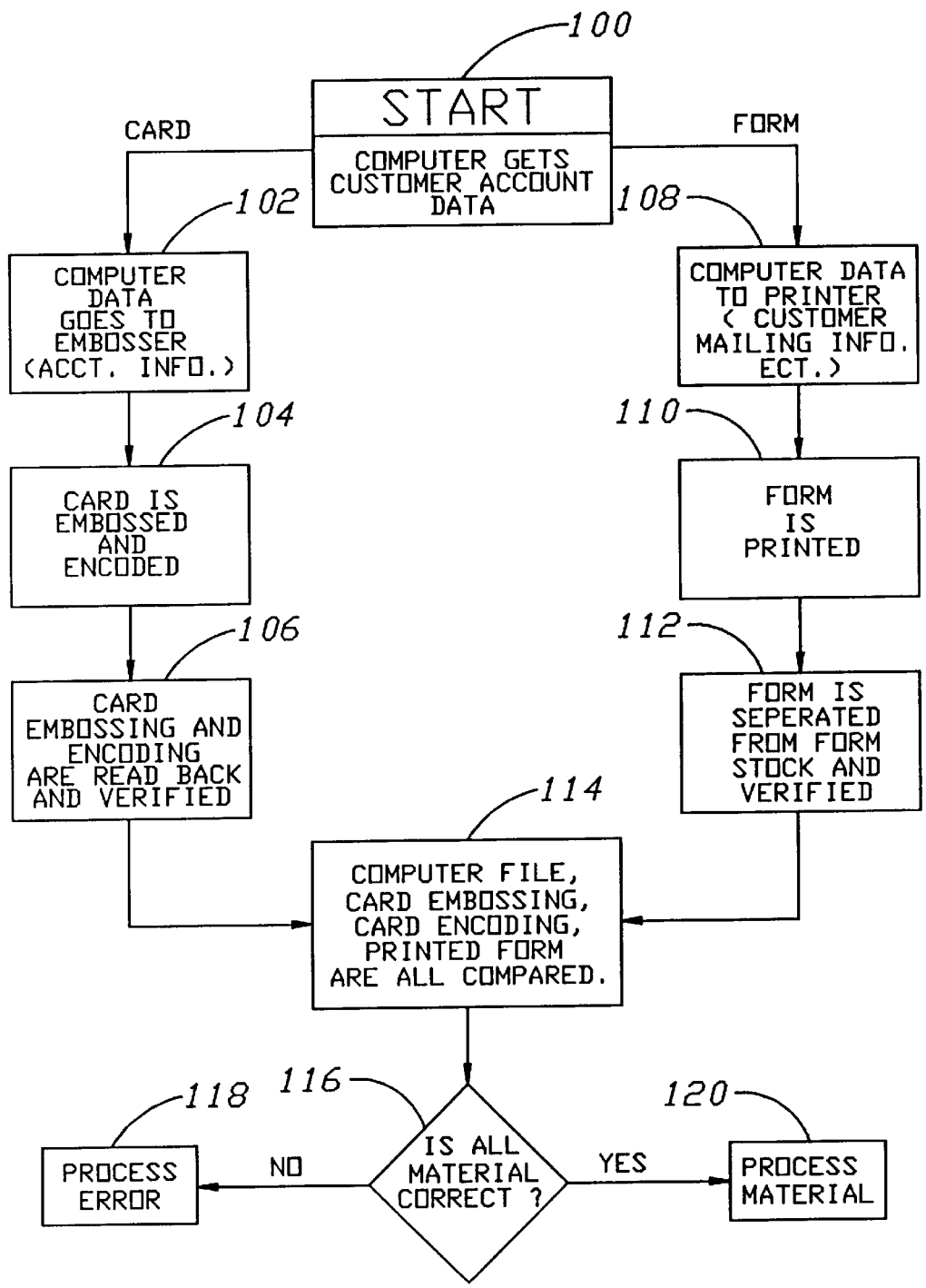

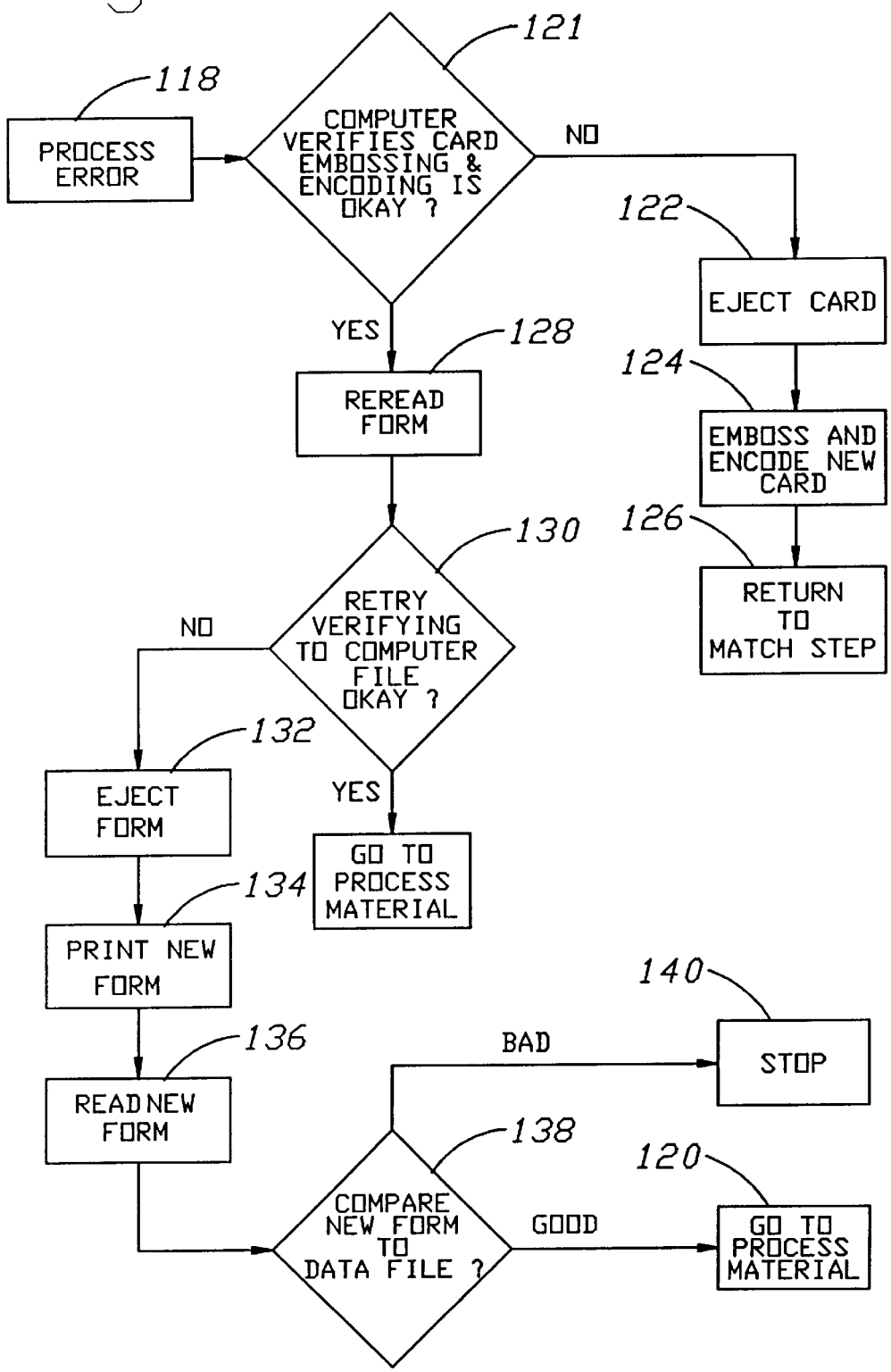

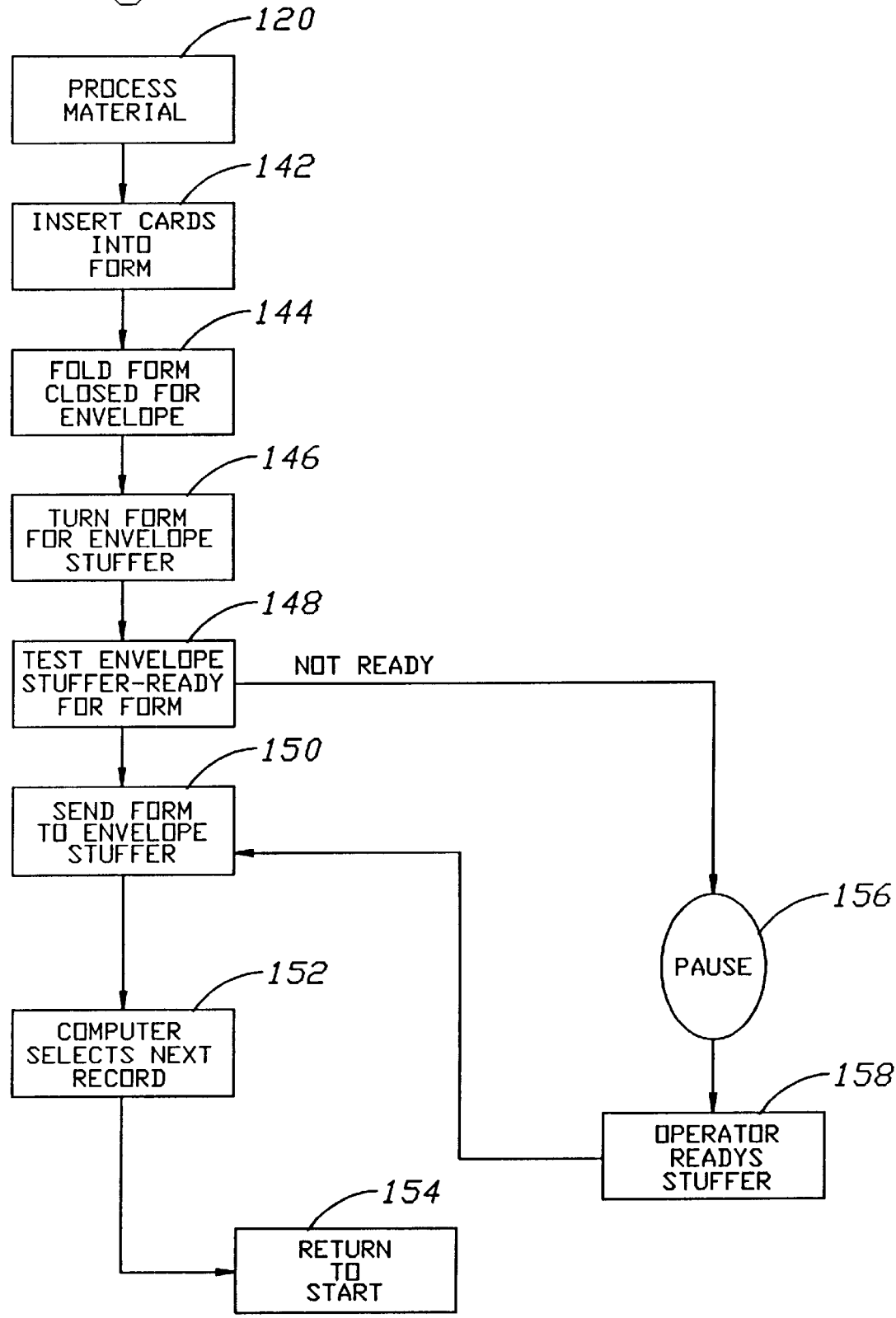

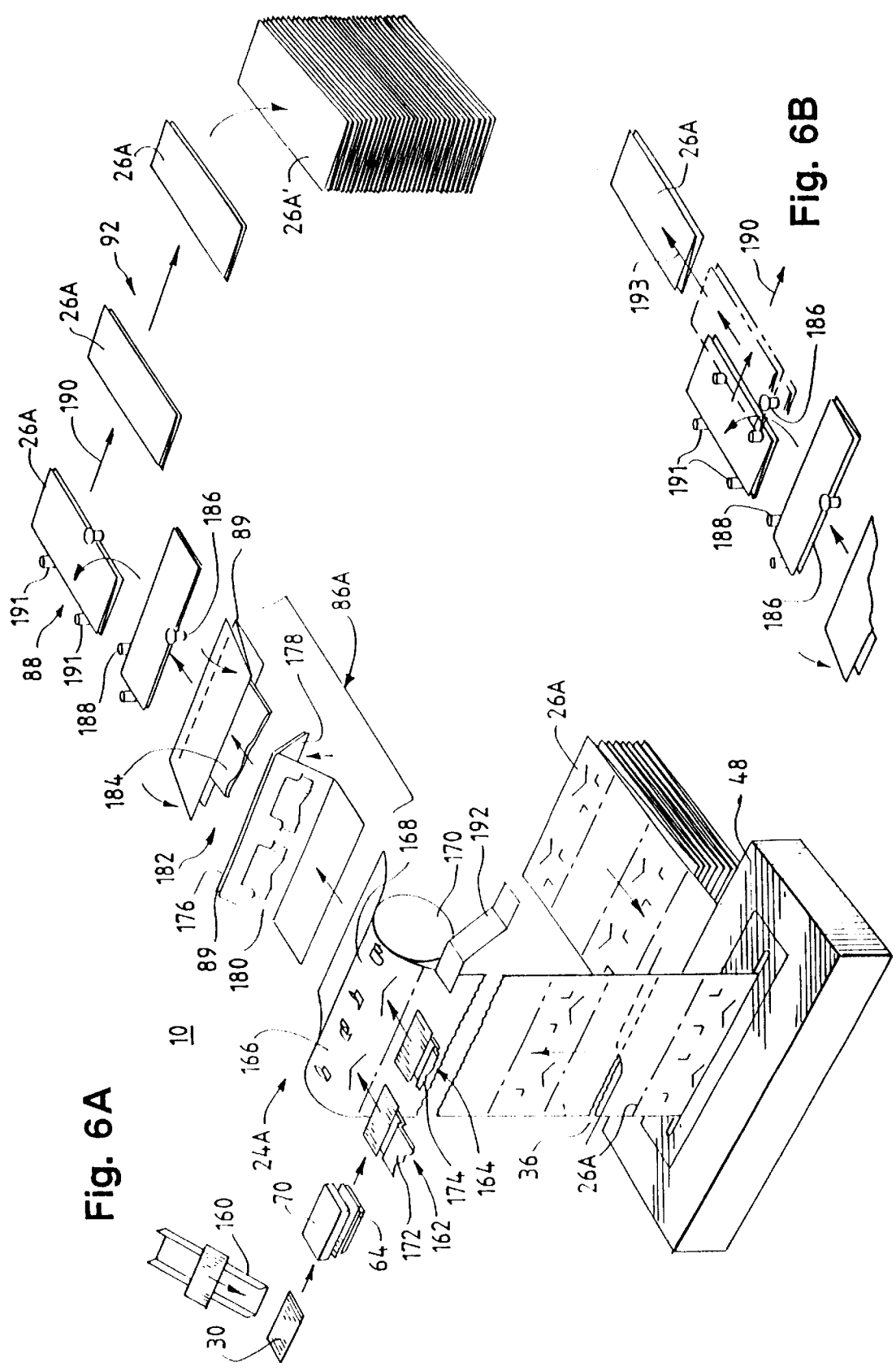

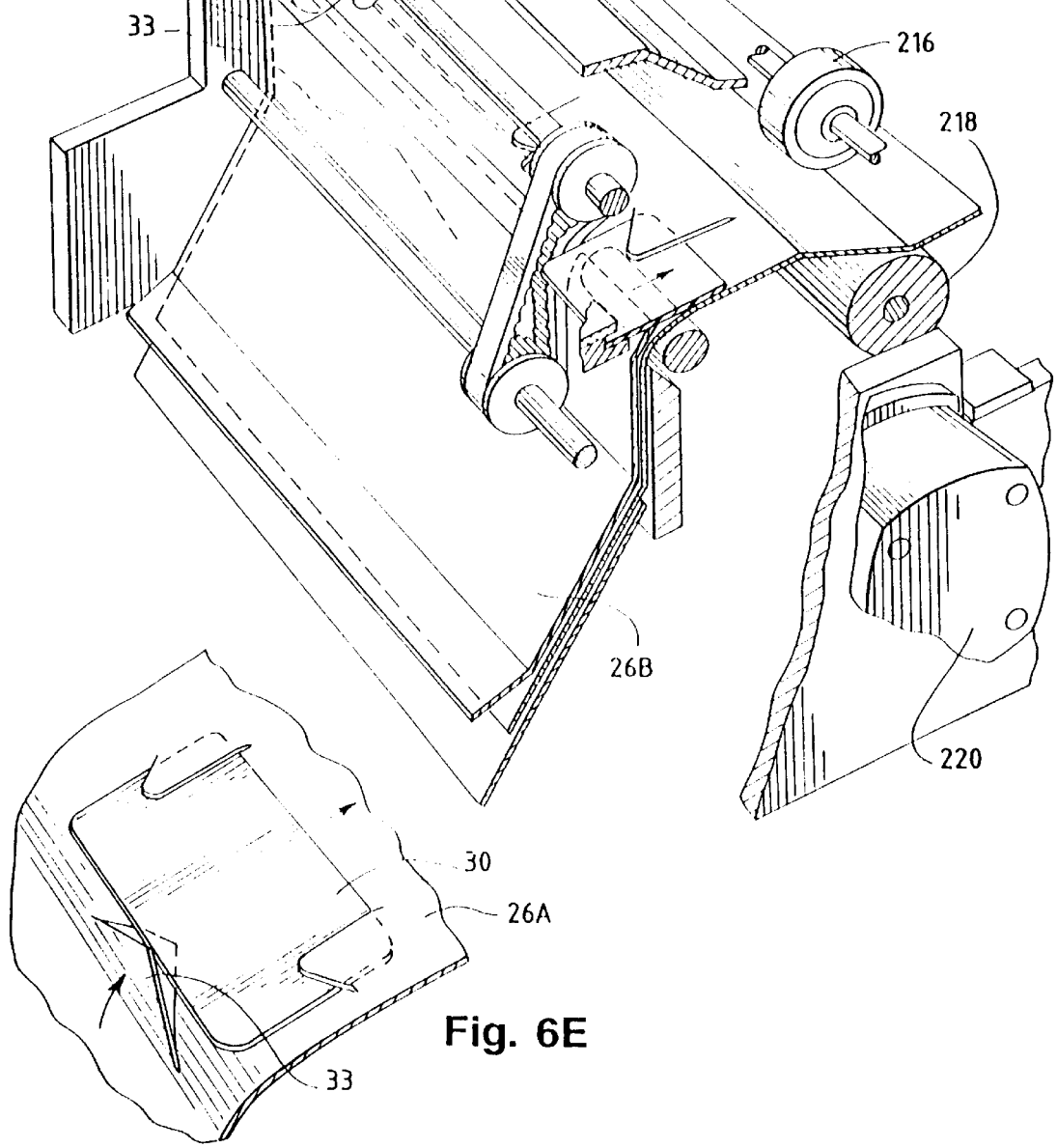

EMBOSSED CARD PACKAGE PRODUCTION SYSTEM WITH MODULAR INSERTERS FOR MULTIPLE FORMS AND CARD VERIFICATION APPARATUS

CROSS-REFERENCES TO RELATED APPLICATION

This application is a division of application Ser. No. 08/340,268, filed Nov. 15, 1994, which is a division of application Ser. No. 08/036,664 filed Mar. 24, 1993, U.S. Pat. No. 5,388,815 which is a continuation-in-part of appln. Ser. No. 08/019,865 filed Feb. 19, 1993 now abandoned.

APPENDIX

This application includes Appendix A.

BACKGROUND OF THE INVENTION

1. Field of the Invention

This invention generally relates to embossed card package production systems which produce card packages including embossed cards or the like mounted to pair card carrying matching forms, or carriers and, more particularly, to card inserters.

2. Description of the Related Art Including Information Disclosed Under 37 CFR 1.97–1.99

Embossed card production systems such as shown in U.S. Pat. No. 4,384,196 issued May 17, 1983 to McCumber et al. entitled "Apparatus and System for Preparing Data Cards and Mailer Forms and for Attaching Data Cards to Respectively Associated Mailer Forms" and U.S. Pat. No. B1 4,034,210 reexamination certificate issued Feb. 7, 1984 to Hill et al. entitled "Credit Card Carriers and Methods of Manufacture" are known which automatically mount one or more embossed cards, such as plastic credit cards or the like, to corresponding card carrying mailing forms, or carriers, which, in turn, are "stuffed" into window mailing envelopes through which the name and address of the account holder printed on the carrier are viewable for mailing to the holder of the account associated with the cards enclosed in the carrier.

Each of the different types of known card package production systems and card inserters require a different kind of form and, thus, there are a plurality of different types of carrier forms produced for use with these card package production systems. In order for card issuers to automatically issue cards using different types of carriers, it has been required for the issuer to produce and operate a different type of system for each different type of form. The versatility and thus value of these known monoform card package production systems has therefore disadvantageously been severely restrained.

Another problem with known embossed card package production systems is that the carriers which are employed all require the folding of a section of the body of the carrier over an edge of the card to hold the card within a slot or corner pockets. Such wedge trapping of cards disadvantageously require a larger carrier to form the folding section. In addition, when the carrier is unopened, the card is no longer securely mounted to the carrier and is susceptible to inadvertent separation from the mailing carriers. Moreover, in known carrier forms with carrier pockets, the pockets are formed with diagonal cuts which require nonrotary oscillating members to open the card pockets to enable card insertion.

Another difficulty with known card production systems is the failure to obtain full verification of the correctness of the card embossment, the card magnetic stripe encoding and the information printed on the carrier. While in the card pack production system of Hill et al., U.S. Pat. No. B1 4,034,210 cited above, information from the embossed characters is compared with information automatically obtained from the carrier to determine there is a match, there is no independent verification of the correctness of the information. In the system of McCumber et al., on the other hand, no comparison is made between the card and carrier to determine if there is a match. Encoding on a magnetic stripe is compared against stored data for the card and an echo check determines whether an embossment has been made, there is no verification of whether the embossment is the correct embossment or whether it matches the encoding on the card; there is no verification of whether the information printed on the carrier is correct or whether it matches either the embossed or encoded information on the card. Instead, correctness of embossed and printed information is assumed correct and a correct match is assumed by maintaining strict synchronization between production of cards and corresponding characters.

Another serious problem with the card package production system of McCumber et al. is that because of the synchronization require to hopefully obtain a match, it is necessary to insert incorrectly prepared cards, known to be incorrect because of incorrect magnetic stripe encoded information, into corresponding carriers. Although this incorrect card package is supposed to be automatically mounted to a reject station away from the correctly prepared package, if they are not separated, an incorrect package is easily combined with the correctly prepared packages.

Also, the versatility of the known card package production systems is severely limited due to the fact that it is usable with only a single type of inserter section which can process only single type of carrier.

SUMMARY OF THE INVENTION

It is therefore the principal object of the present invention to provide a card package production system with full verification which overcomes the disadvantages of known systems.

The object of the invention is also achieved by provision of a method of mounting cards to a plurality of different mailing forms, comprising the steps of (a) automatically mounting cards to a first type of mailing form with an automatic card mounting apparatus having an insertion station at which cards are mounted to forms, a card feeder for feeding cards to the insertion station and a forms feeder adapted to feed different types of mailing forms to the insertion station, (b) releasably mounting a first type of insertion apparatus at the insertion station to insert cards into a first type of carrier, (c) automatically mounting cards to the first type of carrier forms with the first type of insertion apparatus, (d) removing the first type of inserter from insertion station and mounting in its place a second type of insertion apparatus for inserting cards into a second type of carrier form and (e) automatically mounting cards to the second type of mailing forms by using the second type of insertion apparatus.

BRIEF DESCRIPTIONS OF THE DRAWINGS

The foregoing objects and advantageous features of the invention will be explained in greater detail and others will be made apparent from the detailed description of the preferred embodiment of the present invention which is given with reference to the several figures of the drawing, in which:

FIGS. 3A and 3B are front views of preferred embodiments of different types of card carrier forms preferably used in the preferred embodiment;

Figure 1:
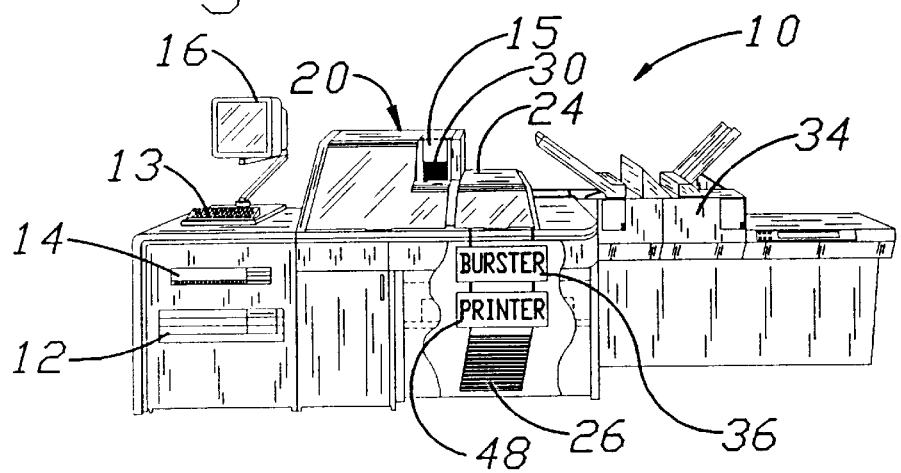
FIG. 1 is a front view of the preferred embodiment of the embossed card pack production system.
Figure 4:
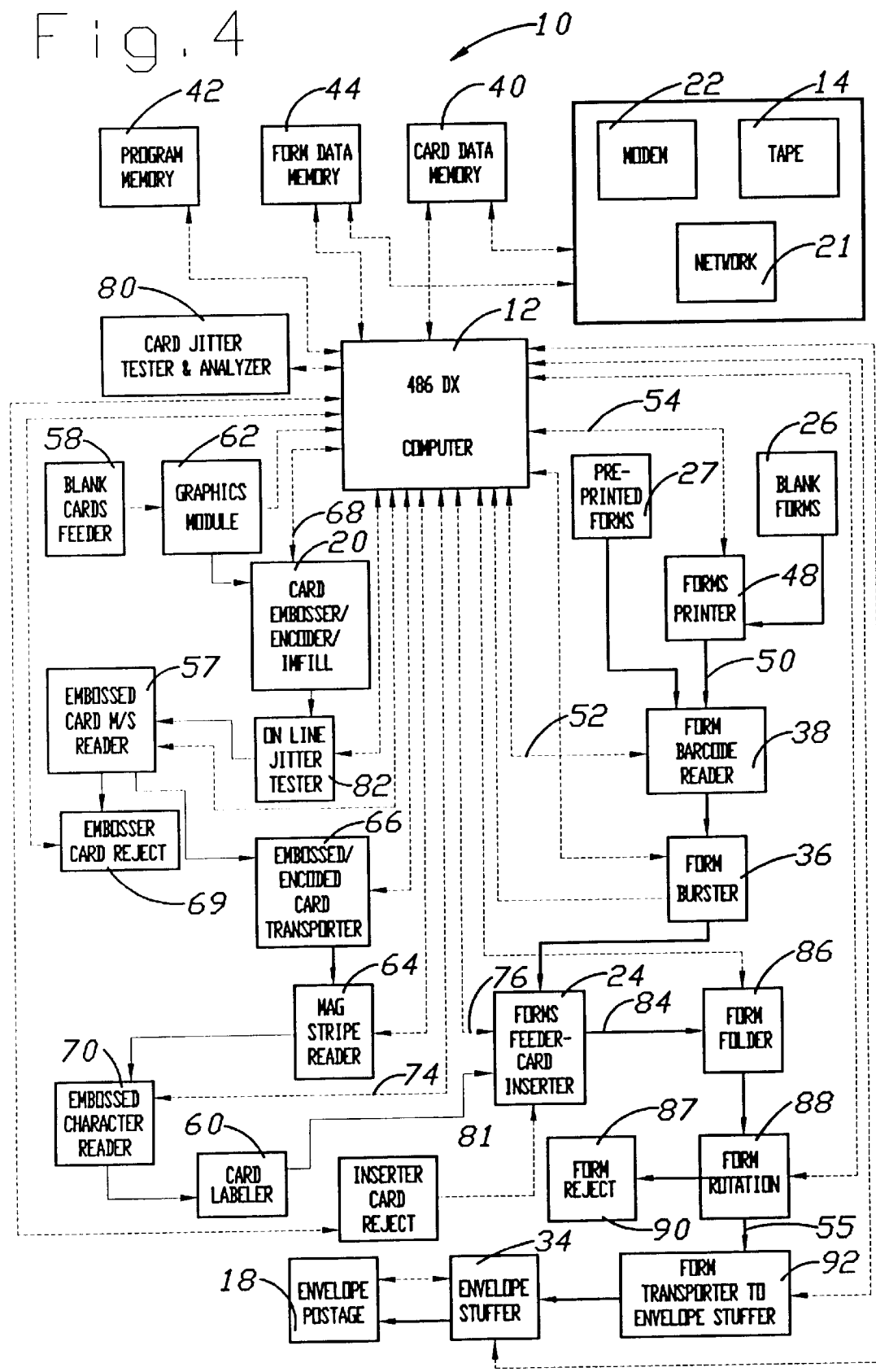
FIG. 4 is a functional block diagram of the preferred embodiment of the embossed card pack production system illustrating the preferred steps for producing an embossed card pack.
Figure 6C:
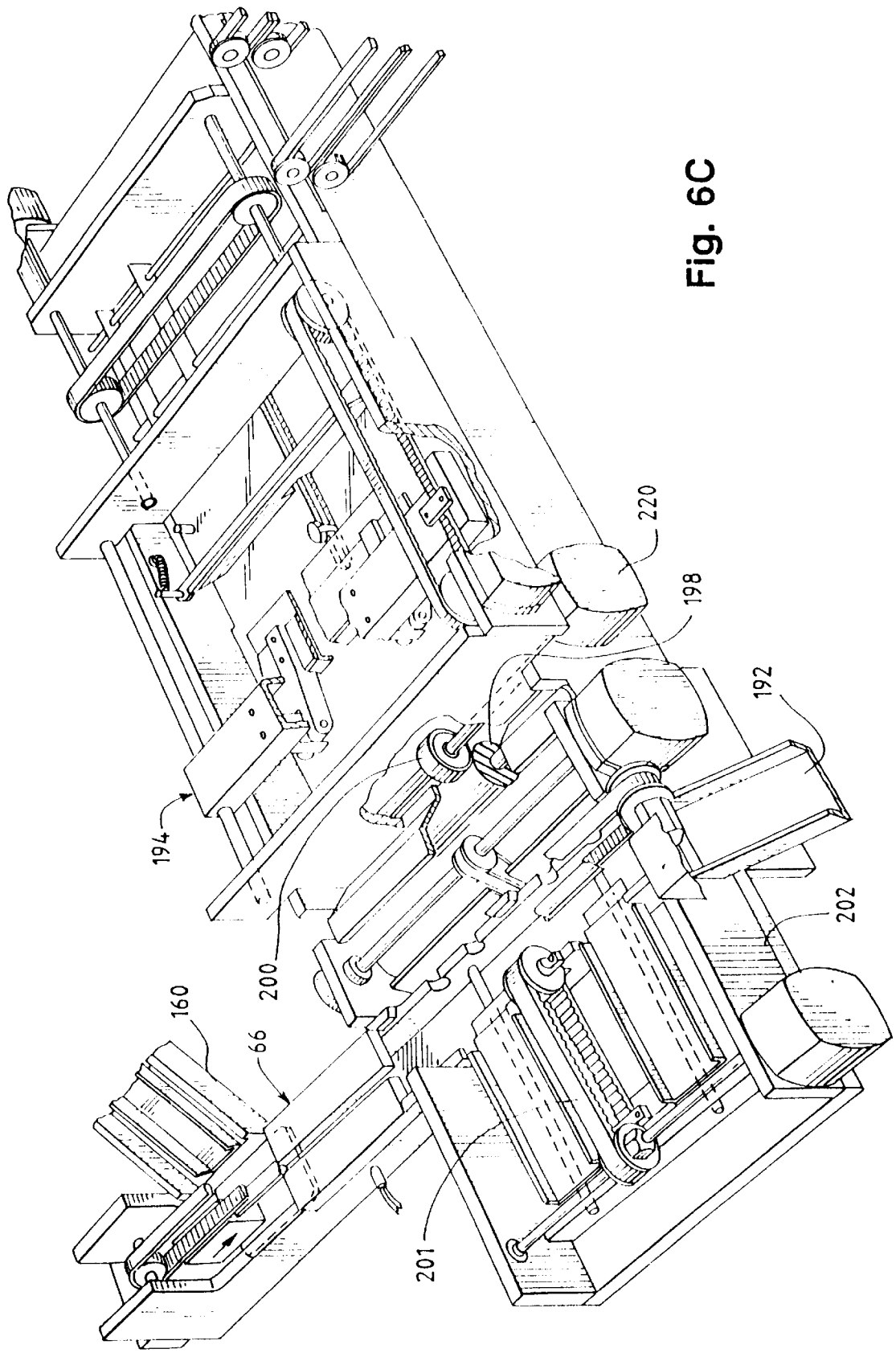
Figure 7A:
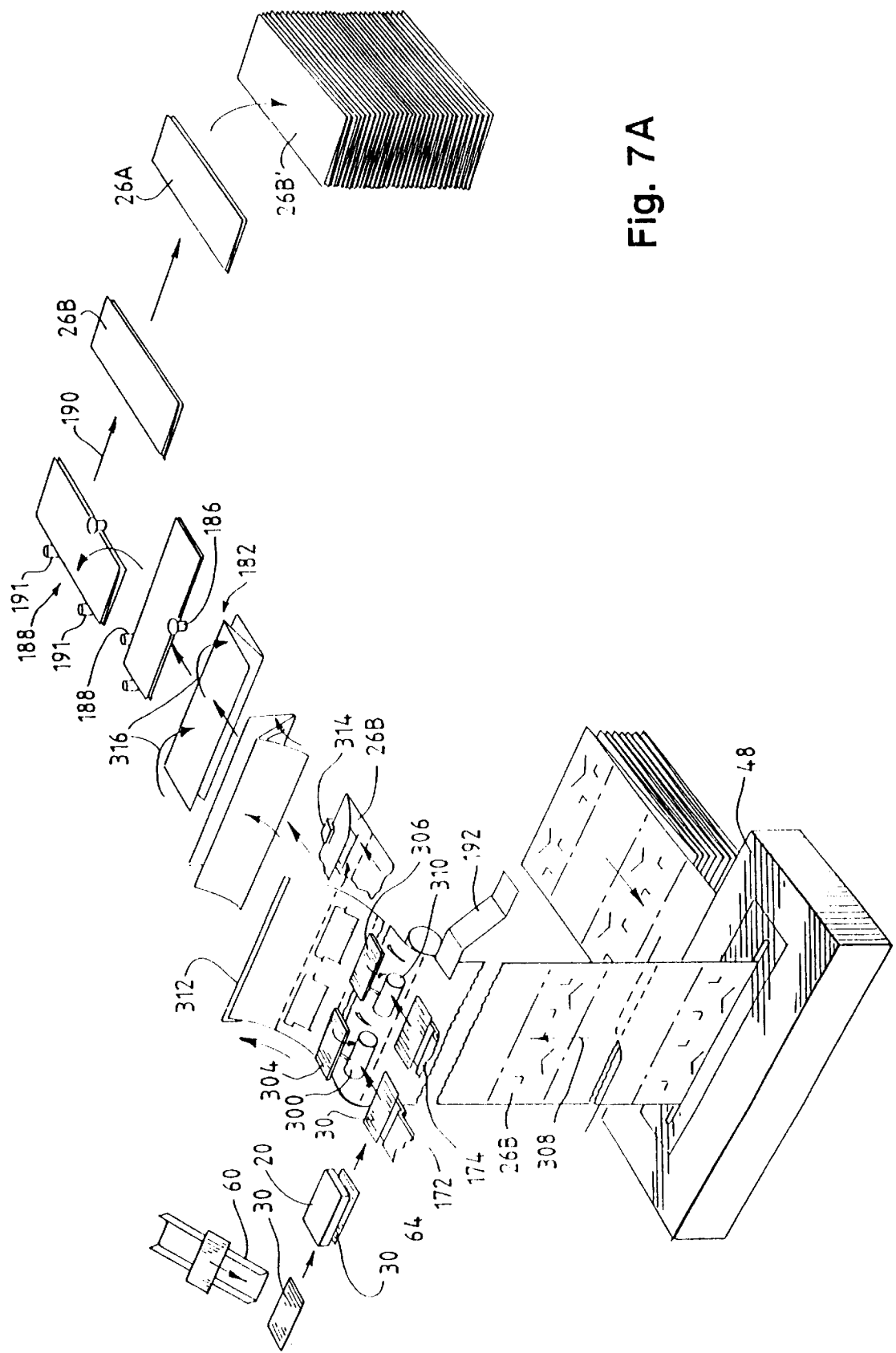
Figure 7B:
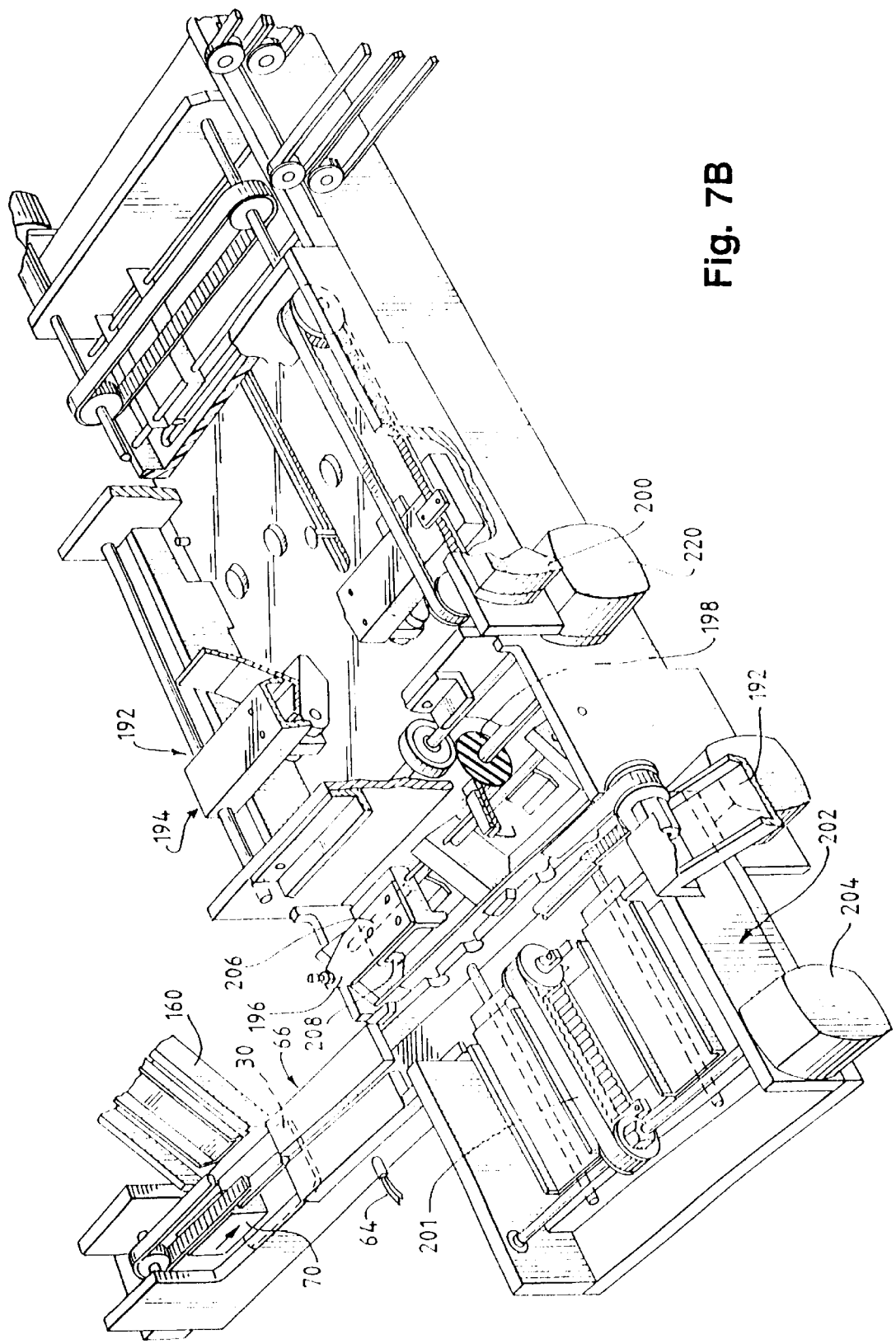
Figures 7C, 7D:
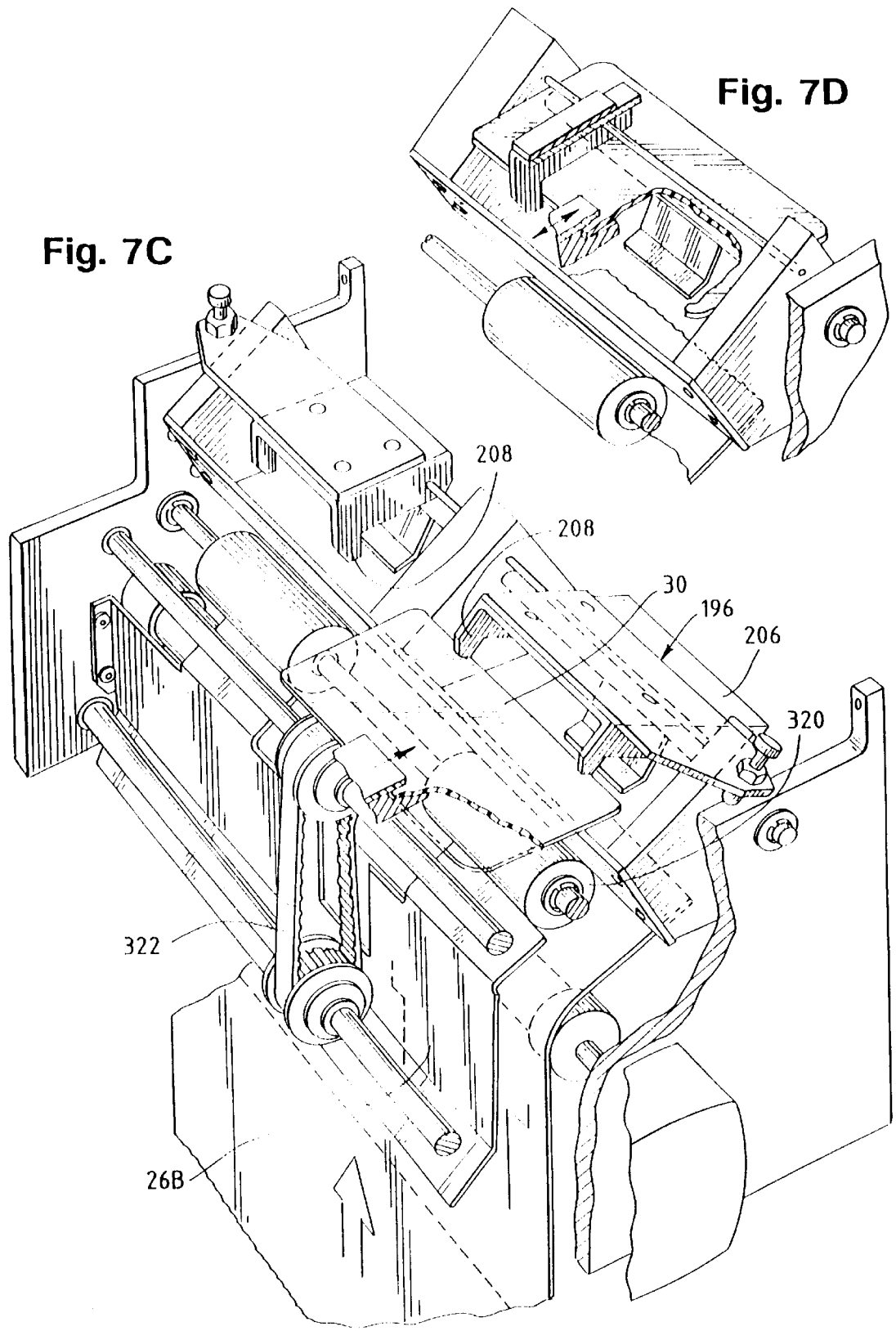
Figures 7E, 7F, 7G:
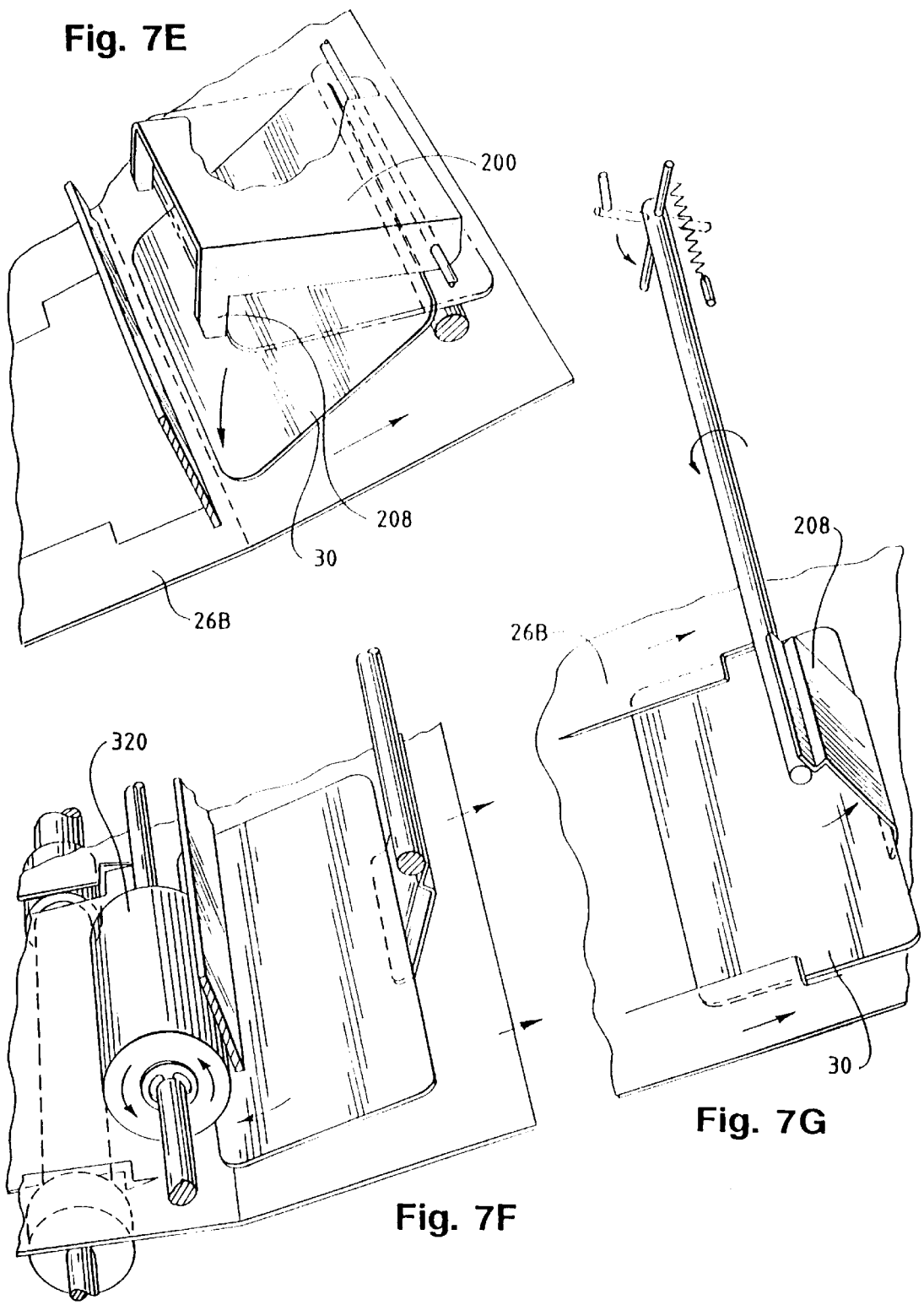

FIG. 5A, B and C are flow charts showing the procedural steps of the card manufacture and insertion process of FIG. 1;

FIG. 6A is a schematic illustration of the operation of the card package production system when using carriers of the type shown in FIG. 3A;

FIG. 6B is a perspective view of the preferred embodiment of the inserter module folder, form rotation and form rejection units of FIG. 4 used for the carrier of FIG. 3A and corresponding to the embodiment illustrated in FIG. 6A;

FIG. 6C is an enlarged perspective view of the preferred embodiment of the portion of the inserter of FIG. 6B which bends the carrier to open the ears of the corner pockets for receipt of a card;

FIG. 6D is a partial perspective view showing how the flap of the carrier of FIG. 3A is bent to engage with the edge of the card during movement of corner pockets away from the inserter;

FIG. 6E is a perspective view of the inserter of FIG. 6D illustrating insertion of the card into the carrier pockets with the flap bent to retain an edge of the card;

FIG. 7A is a schematic illustration of the operation of the card package production system when using carriers of the type shown in FIG. 3B;

FIG. 7B is a perspective view of the preferred embodiment of the inserter module folder, form rotation and form rejection units of FIG. 4 used for the carrier of FIG. 3B and corresponding to the embodiment illustrated in FIG. 7A;

FIG. 7C is a perspective view of the position of the inserter of FIG. 7A at another stop step in the inserting sequence in which a card is held in preparation for engagement with a carrier form of the type shown in FIG. 3B;

FIG. 7D is a perspective view of the position of the inserter of FIG. 7C at a later step in the inserting sequence in which the card has been placed in the position for capture within the pockets of a carrier of the type shown in FIG. 3B;

FIG. 7E is another perspective view of the inserter of FIG. 7D at a later step in the inserting sequence in which the card is in position for capture by the carrier;

FIG. 7F is another perspective view like that of FIG. 7E but with the pocket being opened and about to receive the card; and FIG. 7G is a perspective view of the inserter shown in FIG. 7F at a later step in the inserting sequence in which the card has been slipped into the corner pockets of the carrier of FIG. 3A.

DESCRIPTION OF THE PREFERRED EMBODIMENT

Referring to FIG. 1, the preferred embodiment of the embossed card package production system 10 functions to produce fully verified, embossed and encoded credit cards mounted to verifiably matched carrier forms, or carriers, with the account owner's name and mailing address printed thereon and inserted into window envelopes that are metered with appropriate postage and are ready for mailing.

Figure 2:
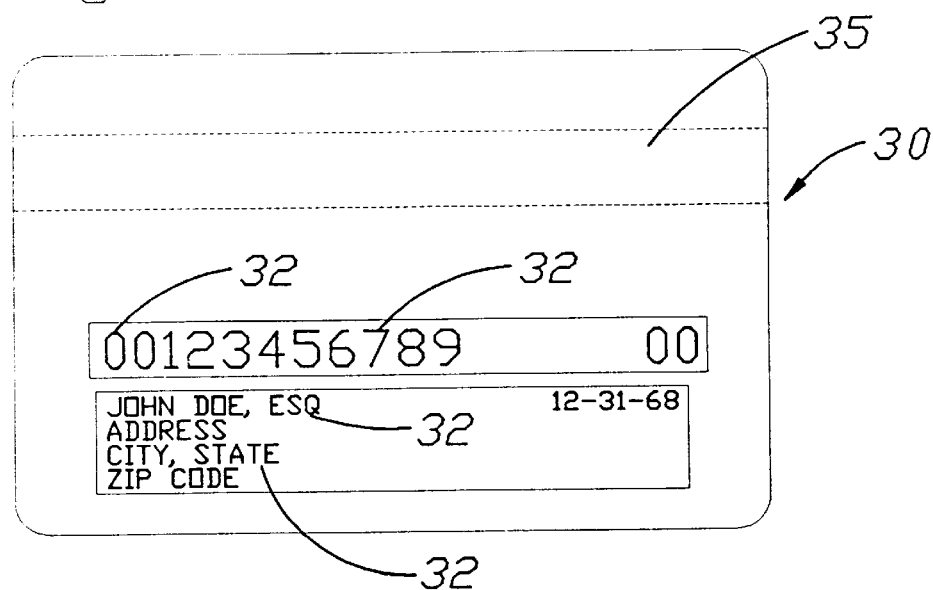
FIG. 2 is an illustration of a card having a magnetic stripe and embossed character.

The system 10 preferably includes a 486 DX computer 12 and an open reel tape drive 14 for controlling the operation of the system. A keyboard 13 is used for manual input of account data and control information into the computer 12. Information inserted into the computer 12 memory is shown at a display screen 16 of the system 10. An embosser section 20 embosses various alphanumeric characters 32 on the face of the card 30, generally the account number and name of the account owner associated with the card, and magnetically encodes like information on a magnetic stripe 35 on the back of the card 30. The embossed and encoded cards 30, FIG. 2, are carried from the embosser section 20 to a card inserter section 24. The inserter section 24 inserts correctly embossed and encoded cards 30 into verifiably matched and correctly printed carrier forms 26. The carrier forms 26 hold one or more embossed cards 30, FIG. 2, which are folded and stuffed into suitable window envelopes (not shown) at an envelope stuffer 34. The stuffed envelopes containing the carrier forms 26 with matching cards 30 are transported to a postage metering machine 18, FIG. 4 (not shown in FIG. 1), to print the appropriate mailing postage on the stuffed envelopes. The materials from which these embossed card packages are produced include blank carrier forms, or carriers, 26 and blank credit cards or like, such as shown in the U.S. patents noted above.

The carrier forms 26 are preferably one of those shown in FIGS. 3A and 3B and a plurality of these interconnected carrier forms 26 are fanfolded like those shown in U.S. Pat. No. 4,034,210 issued Jul. 5, 1977 to Hill et al., and as shown in FIG. 1, but are without marginal pin holes for pin drive feed mechanisms which are not employed in the ECPAP system 10. The printer 48 prints on both types of carrier forms the name and address 35 and bar code 27. The cards 30 with activation labels are mounted to the carrier by means of pockets cut into the plane paper holes 93. For further detailed information about the carrier of FIGS. 3A and 3B, reference should be made to U.S. patent application Ser. No. 08/036,436 of Hill et al. entitled "Card Carrier Forms For Automated Embossed Card Package Production System" filed Mar. 24, 1993, contemporaneously herewith. After having carrier information printed on the end one of a plurality of interconnected, fan folded carriers 26, a burster separates the end one from the others before cards 30 are inserted.

Referring to FIG. 2, the cards 30 have a field for receipt of embossed characters 32 and a magnetic stripe 35 for receipt of magnetically encoded magnetic stripe data relating to the account associated with the card. Common window envelopes which have transparent sections to enable viewing of the name and mailing address printed on the contents of the carrier mailing form are, of course, also provided as well as a full charge, or load, to the postage metering machine.

The system 10 housing contains a slide out drawer for holding the tape driver 14. The blank cards 30 are stacked in a hopper, or chute, 15 and are transported to the card embosser encoder section 20. The cards 30 are embossed with the stored card account information such as the account owner's name, address, card number and expiration date as seen in FIG. 2. The embosser section 20, FIG. 1, also magnetically encodes each card with information identifying the embossed card 30 on the magnetic stripe 35, FIG. 2, of the card. The embossed and encoded cards 30 which are correctly prepared are transported to a card labeler 60, FIG.

4, for automatic placement of removable stick-on activation labels 21 on the card 30. The adhered activation labels preferably are preprinted with a telephone number of the card issuer which the card owner calls upon receipt of the card pack through the mail to request activation of the card for use. The correctly prepared embossed cards 30 with the affixed activation labels are then passed to the card inserter 24 for placement in printed card carrier forms 26. In keeping with one aspect of the invention, labels are only applied to cards determined to be correctly prepared to avoid confusion between correctly and incorrectly prepared cards.

A fan folded stack of blank carrier forms 26 are carried through a forms printer 48 by a forms feeder in the card insertion module 24. The printer 48 prints account information such as the card account owner's name, number and address at a name and address field 35 on the blank carrier forms 26A and 26B. Additionally, one of a plurality of different bar codes 27, such as interleaved two of five code, interleaved three of nine code, Codabar UPC-A&E code, EAN-8 code and EAN-13 code are used to encode the card account information printed on the form 26 such as the account number and name.

The plurality of fan folded carrier forms 26, once printed, are sent to a form burster 36. As noted, the form burster 36 separates the end printed carrier forms 26 from the fan folded plurality of carrier forms 26 to produce individual carrier forms. In addition, in the preferred embodiment, the form burster 36 carries a sensor for reading the code 27 from each carrier form 26 as it is separated from the fan carrier forms 26. For further information relating to the burster, reference should be made to U.S. patent application Ser. No. 08/036,159 of Hill et al. entitled "Card Package Production System With Burster and Carrier Verification Apparatus" filed Mar. 24, 1993, contemporaneously herewith. The separated carrier forms 26 are transported to the card inserter section 24 for receipt of the embossed cards 30. As many as four embossed cards are insertable into a single carrier form 26.

If the information embossed or encoded on the embossed card 30 is not correctly prepared or does not match the associated carrier form 26, the card 30 is sent to one of two reject locations 69 and 81, FIG. 4, without being mounted to a carrier 26 to avoid confusion. Likewise, carrier forms 26 which are not correctly prepared or do not match are rejected and sent to a rejected form location 90, FIG. 4, without having cards mounted to them to avoid confusion. Only correctly prepared carrier forms 26 containing correctly prepared and matching embossed cards 30 are folded and transported to the envelope stuffer 34. Only the envelopes with fully verified carriers are stuffed with the filled card carriers 26 and are transferred to a postage metering machine 18, FIG. 4, to place the appropriate postage on the envelope.

Referring now particularly to FIG. 4, card account data information is stored in a card account data memory 40, preferably a 330 Mbyte, 33 Mhz memory type for the 486 DX computer 12 made by Everex. The card account data for as many as 400,000 accounts are stored in the memory 40 with 870 bytes per account.

The account information preferably includes the name of the account, or owner of the account, the account number, the date of issuance, the date of expiration, the number of cards per account, the credit limit as well as other account information. The card account information stored in the card data memory 40 and the carrier form data stored in the form data memory 44 are selectively obtainable insertable from a number of different data input sources. A modem 22 inputs form and card data information over a telephone line from a remote computer (not shown) to the form data memory 44 and card data memory 40. Alternatively, a hardwire network 21 is used to transfer information from a plurality of computers for receipt at the system 10. Alternatively, a tape reel 14 or the like is employed for inputting card and carrier form data at the hard drive of the ECPAP system 10. This account information is organized in blocks relating to embossments, magnetic stripe encoding and carrier printing. At least some of the information of each block, such as the account number, must correspond or match some of the information of the other blocks.

Based on this account data and control information from manual inputs on the keyboard 13, FIG. 1, the system 10 produces the fully verified embossed card package comprising verified correct credit cards attached to verified correct carrier forms verified to match the attached cards within envelopes bearing postage and ready for mailing to the account owner at the name and address printed on the carrier. As noted, the verification is of the utmost importance to insure that only correctly embossed and correctly encoded cards are attached to matching carrier forms which bear the correct name and address of the account owner of the attached cards. Accordingly, one separate data verification is performed on the forms 26 while three separate data verifications are performed on the cards in addition to matching verification between the carriers and matching cards.

Referring still to FIG. 4, the operation of the 10 is under control of a microprocessor based computer 12 which communicates with the various other functional blocks as indicated by broken line connections therebetween. Card flow between the functional blocks is indicated with solid line connection while carrier flow is indicated by solid bold line connections. The microprocessor 12 is preferably a model A80486DX-3301 or equivalent microprocessor made by Intel Corporation operating at thirty-three MHz, while the program memory 42 and thus data memory is contained in a single or multiple sectored hard drive having a storage capacity of 330 MBytes and preferably comprises a model LXT340A made by Maxtor Corp. An algorithm of the program stored in the program memory 42 pursuant to which the microprocessor 12 operates to control the remaining electromechanical elements of the system 10 is illustrated in FIGS. 5A, 5B, 5C, 6 and 7 and by the listing of the preferred program for implementing the algorithm of FIG. 5A, 5B and 5C, attached hereto as Exhibit A.

Beginning with the flow of carriers 26, under control of the microprocessor 12, blank carrier forms 26 from a supply of fan folded forms 26 are then passed one at a time through a forms printer 48. A carrier form data memory 44 associated with the microprocessor 12 stores information for printing on the blank carrier forms 26. The forms printer 48 then prints on each form stored carrier form information taken from the form carrier data memory 44. This information is selected by the microprocessor 12 from the form carrier data memory 44 and relates to an associated account from the card data memory 40 including the name and mailing address of the account holder and also including other information such as the number of cards to be attached to the carrier form, the dates of issuance and expiration and the credit limit. In addition to the carrier data, the forms printer 48 under control of the microprocessor 12 also prints the bar code 27 and preselected graphics in color, if desired, and other written information, such as the terms of the agreement, which have been preselected for all or a batch of carriers stored in carrier graphics and carrier printing sections of the carrier form data memory 44. Alternatively, preprinted carrier forms 27 with the preprinted carrier account data on the forms are send directly to the form bar code reader 38 and are used for receipt of embossed cards 30 in the system 10.

The carrier account information which is unique to each carrier 26 is also preferably printed in a machine readable format such as a standard bar code 27. In keeping with one of the aspects of the invention, multiple types of bar codes are decodable by bar code reader 38 for enhanced versatility. After the indicated carrier account data has been printed on a carrier 26, such as shown in FIGS. 3A and 3B, the printed carrier is passed via a path 50, to a form bar code reader 38 which photoelectronically senses the bar code associated with the printed account carrier information from each carrier 26. obtaining one aspect of the carrier form bar code reader 38 preferably decodes the following bar codes: interleaved two of five code, interleaved three of nine code, Codabar UPC-A&E code, EAN-8 code and EAN-13 code. The preferred apparatus for sensing and decoding is shown and described in the aforementioned U.S. patent application Ser. No. 08/036,159 of Hill et al. entitled "Card Package Production System With Burster and Carrier Verification Apparatus" filed Mar. 24, 1993, contemporaneously herewith. The read carrier information is passed via a suitable two way communication path 52 to the microprocessor 12 which compares it to the stored carrier information sent to the forms printer 48 via a communication path 54 to determine if there is a match. If the carrier account information read from the carrier 26 is the same as the carrier data obtained from the form data memory 44, then there will be a match and the correct printing of the carrier 26 is verified. In that event, and if there is a match with card information on a card 30 presented for attachment to the carrier 26, the printed forms continue through the form burster 36, the forms feeder-card inserter 24, the form folder 86, the form rotation block 88 to a card package outlet 55 to a form transporter 92 to move it to the envelope stuffer 34, then to the inserter 24 where they are mated with one or more verified and matching cards.

If, on the other hand, the carrier account information read from a carrier 26 does not match the carrier information stored in the carrier form data memory 44, then achieving another objective of the invention, the carrier advantageously is sent to a carrier form rejection area 90 to prevent the incorrect form from being stuffed into an envelope. The carrier 26 passes through the form burster 24 to the forms feeder-card inserter, or inserter, 24, while the card inserter is inhibited from mounting a card. The mismatched or incorrect carrier passes through the inserter 24 without receiving a card. It then passes through the form folder 86 and at the form reject rotation unit 88 it is pushed along path 87 to the form reject location 90. While other bar code readers could be utilized, preferably the form bar code reader 38 is preferably made by Opto Technology as part number QTR while preferably the decoding is performed by a forty pin IC made by Hewlett Packard under part number HBCR-1800. Reference should be made to U.S. patent application Ser. No. 08/036,439 of Hill et al. entitled "Card Package Production System With Modular Carrier Folding Apparatus for Multiple Forms" filed Mar. 24, 1993, contemporaneously herewith, for further information relating to the preferred form of the apparatus for rejecting the incorrect carriers.

While the carrier forms 26 pass through the forms printer 48 and to the inserter 24, the cards 30 make a similar journey from a stack of cards 30 through a blank cards feeder 58, a card graphics module 62, a card embosser/encoder/infill unit 20, an on line jitter tester 82, an embossed card mag stripe reader 57, an embossed card transporter, a card mag stripe reader 64, an embossed character reader 70 and a labeler to the card inserter 24.

The blank cards feeder 58 passes blank cards one at a time to a card graphics module 62 which inputs graphic lettering and designs selectively in color on the blank card surface. The card embosser 20 is preferably of the general type shown in U.S. Pat. No. 4,969,760 issued Nov. 13, 1990 to LaManna et al., or the like. The selected card graphics and card printing information is stored in a card graphics and card printing data section of the program memory 42 and relates to information that applies to all cards or a batch of cards and is not unique to each card, as distinguished from the card account data.

The card embosser 20 embosses the card account embossed information into each card in accordance with continued inputs sent via a communication path 68 which are determined by the microprocessor 12 from the card account embossed data section of the card data memory 40. The embossed card 30 is then sent to the card magnetic stripe encoder of the embosser/encoder unit 20 which encodes the magnetic stripe 35, FIG. 2, on the card 30 with magnetic stripe card information received on the communication path 68 from the microprocessor 12 which, in turn, it obtains from a magnetic stripe card encoding data section of the card data memory 40.

An embossed card magnetic stripe reader 57 reads and decodes information encoded on the magnetic stripe 35, FIG. 2, of the card 30 and compares it with the card account embossed information sent from the card data memory and read by the embossed character reader 70, FIG. 4. In addition, the read encoded information is compared to the encoded account information stored in card data memory 40 used to encode the card. If the encoded information on the magnetic stripe 35, FIG. 3, does not match stored card account information, does not match the embossed information read from the card or the embossed information read from the card does not match the stored embossed account data,then the embossed and encoded card 30 is sent to an embosser card reject area 69. Since the card is incorrectly encoded, it is advantageously prevented from being inserted into a carrier form 26 and stuffed into an envelope to achieve one aspect of the objective of the invention. If the card is correctly encoded, based on the reading by the embosser card M/S reader, the embossed and encoded cards 30 are then moved via the embossed/encoded card transporter 66 to the card magnetic stripe, or M/S reader 64, and the card embossed character reader 70 which respectively receives what is read by each via paths 72 and 74 and makes comparison to account data stored in the card data memory for each and also compares what is read by each to each other. The embossed character reader 70 is preferably of the type shown in U.S. Pat. No. B1 4,194,685 of Hill et al. entitled "Verifying Insertion System Apparatus and Method of Operation" issued Mar. 25, 1980, reissue certificate issued Feb. 19, 1985.

While other devices could be used successfully, preferably the embossed character reader 70 is made by Dynetics Engineering Corporation and is shown in U.S. Pat. No. 4,215,813, while the magnetic stripe reader 64 is preferably made by Brush Industries under part number 901-529-0.

Coupled with the 486 DX computer 12 is a manually operated card jitter tester and analyzer 80 quality check tool built by Q-Card Corp. of Owings Mills, Maryland. A card is manually run through the jitter tester 80 and the computer 12 analyzes the encoding at seventy-five bits per inch of the card for track one and two hundred ten bits per inch for tracks two and three. The card jitter tester and analyzer 80 graphically displays a JT1A report on the display screen 16, FIG. 1, or on a print out indicating if the tested card has been properly encoded. Alternatively, an on line jitter tester 82 is placed for receipt of cards exiting the card embosser/encoder 20. Prior to carrying the embossed and encoded cards 30 to the card labeler 60 by the transporter 66, the on line card jitter tester and analyzer 82 reads the cards to verify proper encoding. Preferably, the jitter tester and analyzer 80 is like one made by Q-Card Company of Owing Mills, Maryland and the on line jitter tester 82 is the same as jitter tester 80 but with a computer interface and automatic card transporter provided.

The microprocessor 12 compares each reading of the embossed information on the card 30 by the photoptical embossed character reader 70 and the magnetic stripe reader 64 to the account data information stored in the appropriate section of the data memory 40 and to each other. Advantageously, the information decoded from the magnetic stripe 35, FIG. 2, of the card 30 by the magnetic stripe reader 64 is compared with the embossed card character information read by the embossed character reader 70 to determine if there is a match. If there is a match of information, the card 30 is internally verified to be correct, and is passed to the inserter 24. If the coded information from the magnetic stripe reader 64 does not match the embossed character information on the card read by the embossed character reader 70 do not match each other, then the microprocessor 12 identifies the card as being incorrectly embossed or encoded and the card is rejected before insertion into a carrier.

After checking the embossed cards 30 for correctness and automatically rejecting the identified incorrect cards, the card transporter 66, under the control of the microprocessor 12, enables the card labeler 60 to label only those. The card labeler 60 automatically applies removable informational labels, such as stick-on card activation labels 21, FIGS. 3A and 3B, to only the correct cards 30. The computer 12 through means of card labeler 60 or, alternatively, the card labeler itself, accumulates information concerning the total number of informational labels applied to the cards 30 and the total number of correct cards. The passing of the correct cards 30 to the labeler is selectively performed either manually or automatically in a single card production apparatus 10, while the labeling is produced only automatically and only on verified correct cards. In this way, correct cards with labels are readily distinguished from rejected cards without labels.

The inserter 24, under control of reports from the microprocessor 12 via a communication path 76 causes the internally verified card 30 to be mounted to a matching carrier 26. Advantageously, the microprocessor via communication path 52 compares the coded carrier information read from the form bar code reader 38 with the coded card information read from the magnetic stripe reader 64 and the embossed information read by the embossed character reader 70 to determine if there is a match and thereby eliminates the need for synchronization between card and carrier production to achieve a match without verification. Advantageously, the card inserter 24 rejects the cards 30 which do not match the carrier information decoded from the carrier 26 before insertion into a carrier. The nonmatching cards are sent to an inserter card reject area 81 and the empty carrier 26 is separately sent to a carrier form reject area 90. Cards 30 having information which does not match the carrier information or the stored account information are prevented from being inserted into the corresponding carrier at the card inserter 24. The embossed cards 30 which have card information that do match the decoded carrier information are mounted to the matching carrier 26 at the card inserter 24.

One or more cards 30 are selectively insertable into a single matching carrier form 26. The automatic card mounting apparatus or card inserter 24 is located at an insertion station at which cards 30 are mounted to carrier forms 26 including those shown in FIGS. 3A and 3B. The embossed card package production system 10 routes cards 30 to a plurality of different carrier mailing forms 26. Referring to FIGS. 3A and 3B two types of carrier forms 26A and 26B employed in the system 10, FIG. 1, are shown holding embossed cards 30. The first type of form 26A, FIG. 3A, is flexible planar body 93 having a pair of spaced parallel ear shaped slots, or corner pockets, 28 for receipt of the sides 31 of a card 30 and one of either the top or the bottom of the card. The form 26A has a bottom flap, or lip, 33 for receipt of the other of the top or bottom or the card 30. The corner pockets 28 and the lip 33 are cut from the flexible planar body 93. The card 30 is held between the pockets 28 and the lip 33 at a location spaced from the periphery of the body 93. The corner pockets 28 hold the card 30 against movement in three of four possible rectilinear directions. The lip 33 engages with an edge of the card 30 and is intermediate to the corners of the card to hold the card 30 against movement in the fourth possible rectilinear direction.

A second type of carrier form 26B seen in FIG. 3B has a flexible planar body 93 with a pair of parallel spaced side slot sections 29 and a fold 89 to hold the card 30 within the side slots. The mailing form 26B has a pair of rectilinear slots 39 cut in the body 93 to form a pair of opposed corner pockets for receipt of opposed corners 41 of the card 30. The rectilinear slots 39 have a pair of parallel spaced slot sections 29 and a cross slot section 43 transversely extending between the pair of parallel spaced slot sections 29. In the form of FIG. 3A, the corner pockets open away from the leading end section and the address and toward the bar code field 27 while in the carrier of FIG. 3B, the address is located on the lagging end section while the pockets face toward the bar coding and away from the leading edge. Reference should be made to U.S. patent application Ser. No. 08/036, 436 of Hill et al. entitled "Card Carrier Forms For Automated Embossed Card Package Production System" filed Mar. 24, 1993, contemporaneously herewith, for further details about each of these different types of carriers.

In the system 10 a card feeder or transporter 66 feeds cards 30 to the insertion station at which a card inserter 24 is located. The card inserter module 24 includes a forms feeder adapted to feed the different types of mailing carrier forms 26A and 26B from the fan of folded carriers to an insertion station. A first type of card insertion apparatus 24 is releasably mounted at the insertion station to insert cards 30 into one type of form carrier 26A. The card inserter 24 automatically mounts embossed cards 30 to the first type of carrier forms 26A. To insert cards 30 into a different or second type of carrier 26B in the ECPAP system 10, the first type of inserter is removed from the insertion station and mounted in its place is a second type of card insertion apparatus for inserting cards into the second type of carrier form 26B. The embossed cards 30 are automatically mounted to the second type of carrier mailing form 26B by using the second type of insertion apparatus.

After all the cards 30 have been attached to a matching carrier form 26, the inserter 24 passes the filled carrier form via path 84 to a form folder 86. The form folder 86 folds the loaded carrier 26 along two perforation lines 89, FIG. 3, to divide the carrier into three equal areas. As with the inserters, two different types of folders are alternatively employed for folding different types of carriers. The folded carrier forms 26 are rotated by an arm at a form rotation station 88 for insertion into mailing envelopes. Before being rotated, the form of FIG. 3A is flipped over after folding while the form of FIG. 3B does not and therefore different folders are used when there are different carrier forms. Empty carrier forms 26 which do not match with a corresponding card or are otherwise improperly prepared are sent via a transportation path 87 to a form reject area 90 to avoid placement into mailing envelopes. The preferred embodiment of the form folder 86, form rotation unit 88, form reject unit 90 and form transporter to envelope stuffer 92 are shown in U.S. patent application Ser. No. 08/036,439 of Hill et al. entitled "Card Package Production System With Modular Carrier Folding Apparatus For Multiple Forms" filed Mar. 24, 1993, contemporaneously herewith, and reference should be made thereto for details of how the different carriers of FIGS. 3A and 3B are folded different to point them both to the envelope stuffer in the correct orientation.

Folded carriers 26 with correctly matched embossed cards 30 are carried along a form transporter 92 to the envelope stuffer 34. The envelope stuffer 18 preferably used is a Pitney Bowes Spectrum Model F400. The envelope stuffer 34 places the filled and folded carrier form 26 into a window envelope from a supply of window envelopes. The stuffed envelopes are then sealed and passed to a postage metering machine (not shown) which applies correct postage to the envelope. The postage metering machine used is preferably one made by Pitney Bowes such as Paragon Mail Processor Model Nos. USS4–USS9, Eagle Model E660 or E670, or a Model 5300 or 5636.

Also preferably performed in the embossed card package production apparatus 10 is a method of mounting cards to a plurality of different mailing forms, comprising the steps of (a) automatically mounting cards to a first type of mailing form with an automatic card mounting apparatus having an insertion station at which cards are mounted to forms, a card feeder for feeding cards to the insertion station and a forms feeder adapted to feed different types of mailing forms to the insertion station, (b) releasably mounting a first type of insertion apparatus at the insertion station to insert cards into a first type of carrier, (c) automatically mounting cards to the first type of carrier forms with the first type of insertion apparatus, (d) removing the first type of inserter from insertion station and mounting in its place a second type of insertion apparatus for inserting cards into a second type of carrier form and (e) automatically mounting cards to the second type of mailing forms by using the second type of insertion apparatus. For details of the methods of operation, reference should be made to U.S. patent application Ser. No. 08/036,657 of Hill et al. entitled "Automatic Verified Embossed Card Package Production Methods" filed Mar. 24, 1993, contemporaneously herewith.

Also, performed in the embossed card package production apparatus 10 is an improved verification system, comprising means for determining when a card has been incorrectly prepared and means for preventing an incorrectly prepared card from being inserted into a carrier.

Referring now to FIG. 5A, the computer 12 retrieves customer account information in step 100 including the name of the customer, the account number, the date of issuance, the date of expiration as well as other information. In step 102 the account information is transferred to the embosser while in step 108 the form printer receives the customer mailing information. In step 104 the blank card is embossed and the magnetic stripe encoded with the account information while in step 110 the form is printed with the customer mailing information.

In step 106 the card is read back and verified with the computer file while in step 112 the form is separated from the stock and read at the bursting station. In step 114 the computer file, the embossed card information read from the card, the encoded information read from the card, and the printed information read from the carrier form are all compared together to determine if there is a match. In step 116 a determination is made as to whether all the information is correct.

Referring now also to FIG. 5B, if all the information is not correct, the error is processed in step 118. In step 120 the counter verifies if the embossing and encoding are correct. If an error is detected, in step 122 the counter will cause rejection of the card and will then in step 124 cause a new card to be embossed and encoded. In step 126, after the new card is prepared, the counter returns to step 114 to compare the new card to determine if the new card has been properly prepared.

If in step 121 the card is verified to be prepared correctly, in step 128 the form will reread and in step 130 a comparison will be made to verify if the form and computer file match. If the form matches the file, the form and card are then processed in step 120 detailed in FIG. 5C.

If the form is correct, the form is ejected in step 132, a new form is printed in step 134, and the new form is read in step 136. In step 138 the new form is compared to the data file. If the file matches the form, a decision is made to process the card and form. If a discrepancy still occurs, the microprocessor based computer will stop the operation in step 140 and operator intervention is required.

Referring now to FIG. 5C, if the embossed encoded card, the printed carrier form and the information in the computer file match and a decision has been made to process in step 120, in step 142 the computer 12 causes the cards to be inserted into the carrier form and then in step 144 fold the carrier forms are folded closed for insertion into envelopes. The forms are then turned ninety degrees in step 146 so that the forms are in proper alignment for insertion into an envelope by an envelope stuffer.

In step 148 the computer 12 checks if the envelope stuffer is ready for receipt of a form. If not ready, the computer 12 pauses in step 156 to allow the operator readies the stuffer in step 158. After it is determined in step 148 that the envelope stuffer is ready, the stuffed carrier forms are sent to the envelope stuffer in step 150.

The microprocessor based computer 12 selects the next customer account record in step 152 and returns to the start process 100, FIG. 5A, in step 154.

Referring now to FIG. 6A, a preferred embodiment of the portion of the card package production system 10 following the embossed/encoded card transfer 66 from the card embosser 20 is schematically illustrated with the card inserter function 24, as well as the form folder function 86, performed by an inserter apparatus 24A and a folder apparatus 86A especially adapted to insert cards into and fold carriers of the type shown in FIG. 3A.

The cards 30 come down a slide 160, are transported past the mag stripe reader 64 and embossed character reader 20 to the second of two card loading stations 162 and 164 at the inserter 24A, if the card is to be loaded into the second of two card mounting locations 166 and 168. If not, the card 30 is moved only to the first loading station 162 to be mounted into card mounting location 166.

A fan folded plurality of interconnected carrier forms 26A and moved to the burster 36 after being printed with carrier information by the forms printer 48. The bar code 27 printed on the carrier is read during the bursting operation. After the cards 30 are verified and the carrier 26A has been verified, the end carrier form 26A is forced to conform to the cylindrical surface of a roller 170 which causes the ears of corner pockets 31 to open and pusher members 172 and 174 to push the cards into the corner pockets. The carrier form continues to roll away from the inserter with the cards in the pockets and the lip 33 on the card then prints up and over the edge of the card 30 to hold it within the pockets 31, as best seen in FIG. 6E. The form is then pushed against a pivotally mounted stop member 176 until the leading end section 178 and middle card carrying section 180 buckle along fold line 89 away from the folding path 182. A pusher arm 184 then pushes against the middle section 180 adjacent the lagging fold line 89 until the carrier 30 is completely folded as shown. A pushing member 186 then pushes the folded carrier against a pivot pin 188 to rotate the folder form at the form rotation station 88. The folded form is then moved along a path 190 by pusher 191 toward an envelope stuffer 34 (rotation) or to an output stack of loaded carriers 26A' to the front reject location 90 (not shown).

Still referring to FIG. 6A, if the card 30 is not prepared correctly or does not match the carrier, then the rejected cards 301 are moved past the insertion stations 162 and 164 and down a chute 192 to prevent if from being loaded into a carrier 26A.

Referring to FIG. 6B, similar action is taken with a carrier which is incorrectly prepared or does not match a card. In that event, no card 30 is loaded prior to passing the carrier 26A through the folder 86A and to the form rotation module 88. However, instead of the pushers 191 pushing the empty carrier along path 190 as shown in FIG. 6A, the pusher 191 only pushes the empty carrier 26A into the path 194 of the pusher 186 which then pushes it away from the path 190 to the form reject location 90 (not shown) in the direction of arrow 193.

Referring now to FIGS. 6C, D and E, the preferred embodiment of the inserter 26A module and folder 86A module is shown in which a pushing apparatus 202 for pushing the folded carrier is to a load position. The card 30 is moved by a conveyor belt of the card transporter 66 to the carrier loading positions when they are pushed into the pockets of the carriers 26A held below a roller 198 and a roller 200.

Referring to FIGS. 6D and E, it is seen how the ears 210 of the pockets 28 open to receive the card 30 as the carrier is turned below rollers 198 and 200, FIGS. 6B and 6C. In FIG. 6E, the flap 33 is shown resiliently flowing up and over the edge of the card 30 as the adjacent portion of the carrier 26A is bent passing the roller 198. The roller 200 is driven by a motor 214 controlled by the computer 12.

Referring now to FIG. 7A, a preferred embodiment of the portion of the card package production system 10 following the embossed/encoded card transfer 66 from the card embosser 20 in which the card inserter function 24 as well as the form folder function 86 are performed by an inserter apparatus 24B and a folder apparatus 86B which are especially adapted to insert cards into the carrier of the type shown in FIG. 3B. As seen from a comparison of FIGS. 6A and 7A, the remainder of the system 10 remains the same and the inserter 24A and folder 86B are directly substitutable for the member 26A and folder 86A since they both receive cards and carriers in the same way and in the same location and output loaded carriers to an envelope stuffer in the same orientation, direction and location. The modules containing different inserters and folders are of the same size and adapted to releasably fit with the other elements of the system to enable them to be interchanged so that the multiple forms of different types can be processed in the one system.

Because the carrier form 26A operates differently and because the address 35 is located on the end panel separate the one on which the address is located on the carrier form 26A, the carrier form 26B is folded differently and is flipped over on its side before being passed to the form rotation module and the envelope stuffer 34.

The feeding of the card 30 and the carrier 26B to the inserter 24B and the reject of incorrect cards 30 and incorrect carriers 26B is performed the same way as with the inserter 24A and fold 86A as shown in FIGS. 6A, 6B and 6C.

Presuming that neither the card nor the carrier are rejected, the cards 30 are held by a card holding mechanism 196 where they are held until the carrier 26B moves by in the direction of arrow 308. The pockets are opened by rollers 300 and 310. The loaded carrier are then pushed up a guide wall 312 to a stop member at the top of the guide wall. In this position, the leading fold line is aligned with a folding gap at the base of the wall 312 and continued pushing causes it to buckle at the leading fold line and pass through the gap fold line first.

The folded edge of the carrier 26B is then engaged by a stop member 314. Another pushing member (not shown) then pushes the lagging edge of the carrier form along the folding path 182 until it tips over the stop member 314 as shown by arrow 316. The address in the lagging panel now faces upward, and the carrier 26B is turned and moved to the envelope stuffer as previously described with reference to FIG. 7A, etc.

Referring now to FIG. 7B, the cards 30 are moved into engagement with a card holding assembly 196 after they are moved there by a card conveyor 202 which drive the cards toward the card holding assembly 196 by means of a pulley 201 powered by a motor 204 under control of the computer 12. The card holding apparatus 196 has a hinge plate 206 with a pair of legs 208 upon which the cards are supported as best seen in FIG. 7E. As seen in FIGS. 7G and 7F, the carrier travels adjacent a roller 320 which opens the pocket of the carrier 26B. The card is first moved to the position shown in FIG. 7C. Once moved past the legs 208, the plate 206 pivots to drop the card 30 into the carrier as shown in FIGS. 7E and 7G. In FIG. 7C the cards are moved into loading position adjacent the card holding apparatus 196 by the pushing member, associated with the conveyor belt 322, FIG. 7C.

While a detailed description of the preferred embodiment of the invention has been given, it should be appreciated that many variations can be made thereto without departing form the scope of the invention as set forth in the appended claims.

APPENDIX A

DYN-6, Hill et al.
U.S. Patent Application
"Embossed Card Package System
With Modular Inserters For
Multiple Forms and Card
Verification Apparatus"
filed March 24, 1993
Serial No. 08/036,664
and
DYN-6D, Hill et al.
U.S. Patent Application
filed November 15, 1994
Serial No. 08/340,268

```
                            Veripro
'
'Embosser Inserter control program.
'Dynetics Engineering Corp.
'(C) Copyright 1993-1999
'01-21-93 FJK
'
'---------- Motor control port ----------
'
motorporta = &H300
motorportb = &H301
motorportc = &H302
motorportr = &H303: motormode = &H80     '8255 mode 0 (out-out-out)
'
'Motor bit mask (off=1 on=0)
'
'   -port A-
'
motorsoff = &HFF          'master off
                          '
  mcardf = &HFE           'picker forward
  mcardr = &HFD           'picker reverse
minsertf = &HFB           'insert forward
minsertr = &HF7           'insert reverse
   mfeed = &HEF           'feed form
   mform = &HDF           'form to fold station
  mflipf = &HBF           'flip forward
  mflipr = &H7F           'flip reverse
                          '
  mcards = &H3            'picker stop
minserts = &HC            'insert stop
  mfeeds = &H10           'feed stop
  mforms = &H20           'form stop
  mflips = &HC0           'flip stop
'
'   -port B-
'
   mspin = &HFE           'spin form
 mejectf = &HFD           'output forward
 mejectr = &HFB           'output reverse
  mburst = &HF7           'burst start
   mxfer = &HEF           'transfer form to stuffer
                          '
  mspins = &H1            'spin stop
 mejects = &H6            'output stop
 mbursts = &H8            'burst stop
  mxfers = &H10           'transfer stop
                          '

Page 1
```

```
                        Veripro
   feedbrk = &HBF           'feed break
  burstbrk = &H7F           'burst break
  '
  '---------- Sensor data port ------------
  '
  snsporta = &H304
  snsportb = &H305
  snsportc = &H306
  snsportr = &H307: snsmode = &H9B           '8255 mode 0 (in-in-in
)
  '
  'Sensor bit mask
  '
  '  -port B-
  '
   snscardl = &H1           'card at left pocket
   snscardr = &H2           'card at right pocket
   snsinsert = &H4          'inserted (match)
   snscardp = &H8           'card present
  snspicker = &H10          'picker home
    snsfold = &H20          'folde bar home
    snsform = &H40          'form present
    snsspin = &H80          'spiner home
  '
  '  -port C-
  '
  snsoutput = &H1           'output home
  snsreject = &H2           'reject stop
   snsburst = &H4           'burst home
    snsexit = &H8           'ready to xfer
  snsflipdn = &H10          'flip complete
   snsoutdn = &H20          'form exit
  snsrotate = &H40          'form rotated
  '
  '---------- Data port ECR/BCODE ---------
  '
  dataporta = &H308
  dataportb = &H309                          'ecr bits 0-1-2-3
  dataportc = &H30A
  dataportr = &H30B: datamode = &H9A         '8255 mode 0 (in-in-in
-out)
  '
  '-----------------------------------------
  'setup digital i/o board
  '
  OUT motorportr, motormode                  '8255 setup (motor)
  OUT motorporta, motorsoff
  OUT motorportb, motorsoff
```

Page 2

```
                            Veripro
OUT motorportc, motorsoff
OUT snsportr, snsmode                   '8255 setup (sensor)
OUT dataportr, datamode                 '8255 setup (dtat)
OUT dataportc, &HFF
'
'-------------------------
DIM t(500)
DIM tprn(500)
DIM SHARED lcard(12) AS STRING * 240
DIM SHARED lform(66) AS STRING * 80
'
ctpline = 0
formwasdone = 0
'
SCREEN 0
WIDTH 80, 43
COLOR 7, 1
CLS
mbossrecord = 1
'
'CALL ccwclear
GOSUB getfig
GOSUB rdlast
GOSUB formatload
pathname$ = figa$: GOSUB getdatafile
pathname$ = figi$: GOSUB linelocload
IF etxtfile$ = "-" THEN
        GOSUB tztfileclear
ELSE
        GOSUB tztfileload
END IF
IF ptxtfile$ = "-" THEN
        GOSUB txtfileclear
ELSE
        GOSUB txtfileload
END IF
'
dev$ = figba$ + ",rs,cs0,ds0,cd0"       'embosser port
OPEN dev$ FOR RANDOM AS #3
'
OPEN figca$ FOR OUTPUT AS #4
'
dsp = 0: GOSUB df
dsp = 0: GOSUB ef
dsp = 0: GOSUB pf
dsp = 0: GOSUB ms
dsp = 0: GOSUB cmset
dsp = 1: GOSUB df Page 3
```

```
                                  Veripro
        dsp = 1: GOSUB ef
        dsp = 1: GOSUB pf
        dsp = 1: GOSUB ms
        GOSUB msshowrec
        activew = 4
        '
        '------------------------
selcmd:
        dsp = 2: GOSUB cmset
        dsp = 3: GOSUB cmset
selcmdlp:
        opx$ = INKEY$
        IF opx$ = CHR$(27) GOTO mfini
        IF opx$ = CHR$(9) THEN activew = activew + 1
        IF LEN(opx$) = 2 AND MID$(opx$, 2, 1) = CHR$(15) THEN activew
= activew - 1
        IF LEN(opx$) = 2 AND MID$(opx$, 2, 1) = CHR$(80) THEN
                stepsel = stepsel + 1
                IF stepsel > 8 THEN stepsel = 1
                dsp = 3: GOSUB cmset
        END IF
        IF LEN(opx$) = 2 AND MID$(opx$, 2, 1) = CHR$(72) THEN
                stepsel = stepsel - 1
                IF stepsel < 1 THEN stepsel = 8
                dsp = 3: GOSUB cmset
        END IF
        IF opx$ = "0" THEN stepsel = 0: dsp = 3: GOSUB cmset
        IF opx$ = "1" THEN stepsel = 1: dsp = 3: GOSUB cmset
        IF opx$ = "2" THEN stepsel = 2: dsp = 3: GOSUB cmset
        IF opx$ = "3" THEN stepsel = 3: dsp = 3: GOSUB cmset
        IF opx$ = "4" THEN stepsel = 4: dsp = 3: GOSUB cmset
        IF opx$ = "5" THEN stepsel = 5: dsp = 3: GOSUB cmset
        IF opx$ = "6" THEN stepsel = 6: dsp = 3: GOSUB cmset
        IF opx$ = "7" THEN stepsel = 7: dsp = 3: GOSUB cmset
        IF opx$ = "8" THEN stepsel = 8: dsp = 3: GOSUB cmset
        IF opx$ = "9" THEN stepsel = 9
        '
        IF opx$ = CHR$(13) AND stepsel = 1 THEN
                LOCATE mswy + 9, mswx + 12: PRINT SPACE$(19);
                LOCATE 35, 50: PRINT SPACE$(19);
                LOCATE 36, 50: PRINT SPACE$(15);
                mbosscmd = 1
                CALL ccwembosser
                LOCATE 35, 50: PRINT "Embosser status ="; mbossstatus;
                LOCATE 36, 50: PRINT mbosserr$;
        END IF
        '
        IF opx$ = CHR$(13) AND stepsel = 2 THEN
                                  Page 4
```

```
                              Veripro
             LOCATE mswy + 9, mswx + 12: PRINT SPACE$(19);
             LOCATE 35, 50: PRINT SPACE$(19);
             LOCATE 36, 50: PRINT SPACE$(15);
buttontwo:   amtcmd = 1: CALL ccwprinter
             IF autolpt = 1 GOTO buttontwo
             IF autolpt = 2 THEN autolpt = 0
             LOCATE 35, 50: PRINT "Printer status ="; amtstatus;
             LOCATE 36, 50: PRINT amterr$;
      END IF
      '
      IF opx$ = CHR$(13) AND stepsel = 3 THEN
             LOCATE mswy + 9, mswx + 12: PRINT SPACE$(19);
             LOCATE mswy + 10, mswx + 12: PRINT SPACE$(19);
             LOCATE 36, 50: PRINT SPACE$(15);
rdtest:      cardcmd = 1
             CALL ccwct
             LOCATE 35, 50: PRINT "Card status ="; cardstatus;
             LOCATE 36, 50: PRINT crderr$;
             IF cardstatus = 1 GOTO rdtest
             IF cardstatus = 2 THEN GOTO rdtest
      END IF
      '
      IF opx$ = CHR$(13) AND stepsel = 4 THEN
             LOCATE mswy + 8, mswx + 12: PRINT SPACE$(19);
             LOCATE 36, 50: PRINT SPACE$(15);
bstest:      burstcmd = 1
             CALL ccwburst
             LOCATE 35, 50: PRINT "Burst status ="; burststatus;
             LOCATE 36, 50: PRINT bursterr$;
             IF burststatus = 1 GOTO bstest
             'IF burststatus = 2 THEN GOTO bstest
      END IF
      '
      IF opx$ = CHR$(13) AND stepsel = 5 THEN
             LOCATE 36, 50: PRINT SPACE$(15);
matchtst:    matchcmd = 1
             CALL ccwmatch
             LOCATE 35, 50: PRINT "Match status ="; matchstatus;
             LOCATE 36, 50: PRINT matcherr$
             IF matchstatus = 1 GOTO matchtst
      END IF
      '
      IF opx$ = CHR$(13) AND stepsel = 6 THEN
             LOCATE 36, 50: PRINT SPACE$(15);
             procescmd = 1
ppcmtst:     CALL ccwproces
             LOCATE 35, 50: PRINT "Proces status ="; ppstatus;
             LOCATE 36, 50: PRINT proceserr$
                              Page 5
```

```
                              Veripro
              IF ppstatus = 1 GOTO ppcmtst
      END IF
      '
      IF opx$ = CHR$(13) AND stepsel = 7 THEN
              LOCATE 36, 50: PRINT SPACE$(15);
              LOCATE 35, 50: PRINT "Stand by .....        ";
              CALL ccwclear
              LOCATE 35, 50: PRINT SPACE$(15);
      END IF
      '
      IF opx$ = CHR$(13) AND stepsel = 8 THEN
      '
coneemboss:
              LOCATE 35, 50: PRINT SPACE$(19);
              LOCATE 36, 50: PRINT SPACE$(19);
              CALL ccwembosser
              IF mbossstatus = 0 GOTO coneprint
              LOCATE 35, 50: PRINT "Embosser status ="; mbossstatus;
              LOCATE 36, 50: PRINT mbosserr$;
              GOTO conedone
              '
coneprint:
              LOCATE 35, 50: PRINT SPACE$(19);
              LOCATE 36, 50: PRINT SPACE$(19);
conelplop:    CALL ccwprinter
              IF autolpt = 1 GOTO conelplop
              IF autolpt = 2 THEN
                      autolpt = 0
                      GOTO coneburst
              END IF
              LOCATE 35, 50: PRINT "Printer status ="; amtstatus;
              LOCATE 36, 50: PRINT amterr$;
              GOTO conedone
              '
coneburst:
              LOCATE 35, 50: PRINT SPACE$(19);
              LOCATE 36, 50: PRINT SPACE$(19);
coneblop:     burstcmd = 1: CALL ccwburst
              LOCATE 35, 50: PRINT "Burst status ="; burststatus;
              LOCATE 36, 50: PRINT bursterr$;
              IF burststatus = 1 GOTO coneblop
              IF burststatus = 0 GOTO conecard
              GOTO conedone
              '
conecard:
              LOCATE 35, 50: PRINT SPACE$(19);
              LOCATE 36, 50: PRINT SPACE$(19);
coneclop:     cardcmd = 1: CALL ccwct
```

```
                                      Veripro
                  LOCATE 35, 50: PRINT "Card status ="; cardstatus;
                  LOCATE 36, 50: PRINT crderr$;
                  IF cardstatus = 1 GOTO coneclop
                  IF cardstatus = 2 GOTO coneclop
                  IF cardstatus = 4 GOTO coneclop
                  IF cardstatus = 0 THEN GOTO conematch
                  GOTO conedone
                  '
conematch:
                  LOCATE 35, 50: PRINT SPACE$(19);
                  LOCATE 36, 50: PRINT SPACE$(19);
conemlop:         matchcmd = 1: CALL ccwmatch
                  LOCATE 35, 50: PRINT "Match status ="; matchstatus;
                  LOCATE 36, 50: PRINT matcherr$
                  IF matchstatus = 1 GOTO conemlop
                  IF matchstatus = 0 GOTO coneprocess
                  GOTO conedone
                  '
coneprocess:
                  LOCATE 35, 50: PRINT SPACE$(19);
                  LOCATE 36, 50: PRINT SPACE$(19);
coneplop:         procescmd = 1: CALL ccwproces
                  LOCATE 35, 50: PRINT "Proces status ="; ppstatus;
                  LOCATE 36, 50: PRINT proceserr$
                  IF ppstatus > 0 GOTO coneplop
                  IF ppstatus = 0 GOTO conecomplete
                  GOTO conedone
                  '
conecomplete:     LOCATE 35, 50: PRINT SPACE$(19);
                  LOCATE 36, 50: PRINT SPACE$(19);
                  LOCATE 35, 50: PRINT "Cycle complete.;"
                  '
conedone:         END IF
                  '
         IF opx$ = CHR$(13) AND stepsel = 9 THEN
                  '
auto:             autostate = 0: autoemb = 0: autolpt = 0
                  remoteexit = 0: pageup = 0
auto1:
                  LOCATE 35, 50: PRINT SPACE$(19);
                  LOCATE 36, 50: PRINT SPACE$(19);
                  CALL ccwembosser
                  IF mbossstatus = 0 GOTO autoe1
                  LOCATE 35, 50: PRINT "Embosser status ="; mbossstatus;
                  LOCATE 36, 50: PRINT mbosserr$;
                  GOTO autoexit
autoe1:           IF autostate = 1 GOTO auto61
auto2:
```

```
                                    Veripro
                    LOCATE 35, 50: PRINT SPACE$(19);
                    LOCATE 36, 50: PRINT SPACE$(19);
autolp2:            CALL ccwprinter
                    IF autostate = 0 AND autolpt = 1 GOTO autolp2
                    IF amtstatus = 0 GOTO autoe2
                    LOCATE 35, 50: PRINT "Printer status ="; amtstatus;
                    LOCATE 36, 50: PRINT amterr$;
                    GOTO autoexit
autoe2:             IF autostate = 1 GOTO auto61
auto3:
                    LOCATE 35, 50: PRINT SPACE$(19);
                    LOCATE 36, 50: PRINT SPACE$(19);
auto31:             burstcmd = 1: CALL ccwburst
                    LOCATE 35, 50: PRINT "Burst status ="; burststatus;
                    LOCATE 36, 50: PRINT bursterr$;
                    IF remoteexit = 0 THEN
                            IF INP(snsportc) AND snsexit THEN
                                    remoteexit = 0
                            ELSE
                                    remoteexit = 1
                            END IF
                    END IF
                    IF burststatus = 1 GOTO auto31
                    IF burststatus = 0 GOTO autoe3
                    GOTO autoexit
autoe3:             IF autostate = 1 GOTO auto61
                    IF autostate = 2 GOTO auto71
auto4:
                    LOCATE 35, 50: PRINT SPACE$(19);
                    LOCATE 36, 50: PRINT SPACE$(19);
auto41:             cardcmd = 1: CALL ccwct
                    LOCATE 35, 50: PRINT "Card status ="; cardstatus;
                    LOCATE 36, 50: PRINT crderr$;
                    IF cardstatus = 1 GOTO auto41
                    IF cardstatus = 2 GOTO auto41
                    IF cardstatus = 4 GOTO auto41
                    IF cardstatus = 0 THEN GOTO auto5
                    GOTO autoexit
auto5:
                    LOCATE 35, 50: PRINT SPACE$(19);
                    LOCATE 36, 50: PRINT SPACE$(19);
auto51:             matchcmd = 1: CALL ccwmatch
                    LOCATE 35, 50: PRINT "Match status ="; matchstatus;
                    LOCATE 36, 50: PRINT matcherr$
                    IF matchstatus = 1 GOTO auto51
                    IF matchstatus = 0 GOTO autoe5
                    GOTO autoexit
autoe5:
```

Page 8

```
                           Veripro
auto6:
               autostate = 1
               LOCATE 35, 50: PRINT SPACE$(19);
               LOCATE 36, 50: PRINT SPACE$(19);
auto61:        procescmd = 1: CALL ccwproces
               LOCATE 35, 50: PRINT "Proces status ="; ppstatus;
               LOCATE 36, 50: PRINT procserr$
               IF ppstatus < 0 GOTO autoexit
               IF ppstatus = 0 GOTO auto7
               'IF ppstatus > 6 GOTO auto61
               IF ppstatus = 1 AND autoemb = 0 GOTO auto1
               IF autolpt = 0 GOTO auto2
               IF autolpt = 1 GOTO auto2
               'IF autolpt = 2 GOTO auto3
               GOTO auto61
auto7:
               autostate = 2
               IF pageup = 1 GOTO auto3
auto71:
               autostate = 0
               GOTO auto4

END IF
               '
               '-----
        IF activew = 4 THEN
               GOTO selcmdlp
        ELSE
               dsp = 0: GOSUB cmset
               dsp = 1: GOSUB cmset
               GOTO selnext
        END IF
        '
        '------------------------
seldf:
        dsp = 2: GOSUB df
        dfpick = 1: GOSUB changedf
seldflp:
        opx$ = INKEY$
        IF opx$ = CHR$(27) GOTO mfini
        IF opx$ = CHR$(13) AND dfpick = 1 THEN
               pathname$ = figa$
               GOSUB filewin
               datafile$ = inam$
               LOCATE wy + 2, wx + 14: COLOR 1, 7
               PRINT " "; datafile$;
               PRINT SPACE$(13 - LEN(datafile$));
               COLOR 7, 1
```

```
                                Veripro
                GOSUB getdatafile
                GOSUB msshowrec
                dsp = 1: GOSUB ms
        END IF
        IF opx$ = CHR$(13) AND dfpick = 2 THEN
                GOSUB formatwin
                dformat$ = aam$
                LOCATE wy + 3, wx + 14: COLOR 1, 7
                PRINT " "; dformat$;
                PRINT SPACE$(13 - LEN(dformat$));
                COLOR 7, 1
                GOSUB formatload
                size = (LOF(1) - t(1)) / t(2)
                size = FIX(size)
                GOSUB msshowrec
                dsp = 1: GOSUB ms
        END IF
        IF opx$ = CHR$(9) THEN activew = activew + 1
        IF LEN(opx$) = 2 AND MID$(opx$, 2, 1) = CHR$(15) THEN activew
= activew - 1
        IF LEN(opx$) = 2 AND MID$(opx$, 2, 1) = CHR$(80) THEN
                dfpick = dfpick + 1
                GOSUB changedf
        END IF
        IF LEN(opx$) = 2 AND MID$(opx$, 2, 1) = CHR$(72) THEN
                dfpick = dfpick - 1
                GOSUB changedf
        END IF
        IF activew = 1 THEN
                GOTO seldflp
        ELSE
                dsp = 0: GOSUB df
                dsp = 1: GOSUB df
                GOTO selnext
        END IF
        '
changedf:
        IF dfpick > 2 THEN dfpick = 1
        IF dfpick < 1 THEN dfpick = 2
        IF dfpick = 1 THEN
                LOCATE wy + 2, wx + 14: COLOR 1, 7
                PRINT " "; datafile$;
                PRINT SPACE$(13 - LEN(datafile$));
                LOCATE wy + 3, wx + 14: COLOR 7, 1
                PRINT " "; dformat$;
                PRINT SPACE$(13 - LEN(dformat$));
        END IF
        IF dfpick = 2 THEN Page 10
```

```
                            Veripro
            LOCATE wy + 2, wx + 14: COLOR 7, 1
            PRINT " "; datafile$;
            PRINT SPACE$(13 - LEN(datafile$));
            LOCATE wy + 3, wx + 14: COLOR 1, 7
            PRINT " "; dformat$;
            PRINT SPACE$(13 - LEN(dformat$));
            COLOR 7, 1
        END IF
        RETURN
        '------------------------
selef:
        dsp = 2: GOSUB ef
        efpick = 1: GOSUB changeef
seleflp:
        opx$ = INKEY$
        IF opx$ = CHR$(27) GOTO mfini
        IF opx$ = "-" THEN
            etxtfile$ = "-"
            LOCATE wy + 2, wx + 14: COLOR 1, 7
            PRINT SPACE$(13);
            GOSUB tztfileclear
        END IF
        IF opx$ = CHR$(13) AND efpick = 1 THEN
            pathname$ = figh$
            GOSUB filewin
            etxtfile$ = inam$
            GOSUB tztfileload
            LOCATE wy + 2, wx + 14: COLOR 1, 7
            PRINT " "; etxtfile$;
            PRINT SPACE$(13 - LEN(etxtfile$));
            COLOR 7, 1
        END IF
        IF opx$ = CHR$(13) AND efpick = 2 THEN
            pathname$ = figi$
            GOSUB filewin
            eformat$ = inam$
            GOSUB linelocload
            LOCATE wy + 3, wx + 14: COLOR 1, 7
            PRINT " "; eformat$;
            PRINT SPACE$(13 - LEN(eformat$));
            COLOR 7, 1
        END IF
        IF opx$ = CHR$(9) THEN activew = activew + 1
        IF LEN(opx$) = 2 AND MID$(opx$, 2, 1) = CHR$(15) THEN activew = activew - 1
        IF LEN(opx$) = 2 AND MID$(opx$, 2, 1) = CHR$(80) THEN
            efpick = efpick + 1
            GOSUB changeef
```

Page 11

Veripro

```
            END IF
            IF LEN(opx$) = 2 AND MID$(opx$, 2, 1) = CHR$(72) THEN
                    efpick = efpick - 1
                    GOSUB changeef
            END IF
            IF activew = 2 THEN
                    GOTO seleflp
            ELSE
                    dsp = 0: GOSUB ef
                    dsp = 1: GOSUB ef
                    GOTO selnext
            END IF
            '
changeef:
            IF efpick > 2 THEN efpick = 1
            IF efpick < 1 THEN efpick = 2
            IF efpick = 1 THEN
                    LOCATE wy + 2, wx + 14: COLOR 1, 7
                    IF etxtfile$ = "-" THEN
                            PRINT SPACE$(14);
                    ELSE
                            PRINT " "; etxtfile$;
                            PRINT SPACE$(13 - LEN(etxtfile$));
                    END IF
                    LOCATE wy + 3, wx + 14: COLOR 7, 1
                    PRINT " "; eformat$;
                    PRINT SPACE$(13 - LEN(eformat$));
            END IF
            IF efpick = 2 THEN
                    LOCATE wy + 2, wx + 14: COLOR 7, 1
                    IF etxtfile$ = "-" THEN
                            PRINT SPACE$(14);
                    ELSE
                            PRINT " "; etxtfile$;
                            PRINT SPACE$(13 - LEN(etxtfile$));
                    END IF
                    LOCATE wy + 3, wx + 14: COLOR 1, 7
                    PRINT " "; eformat$;
                    PRINT SPACE$(13 - LEN(eformat$));
                    COLOR 7, 1
            END IF
            RETURN
            '------------------------
selpf:
            dsp = 2: GOSUB pf
            pfpick = 1: GOSUB changepf
selpflp:
            opx$ = INKEY$
```

Page 12

```
                              Veripro
        IF opx$ = CHR$(27) GOTO mfini
        IF opx$ = "-" THEN
                ptxtfile$ = "-"
                LOCATE wy + 2, wx + 14: COLOR 1, 7
                PRINT SPACE$(13);
                GOSUB txtfileclear
        END IF
        IF opx$ = CHR$(13) AND pfpick = 1 THEN
                pathname$ = figg$
                GOSUB filewin
                ptxtfile$ = inam$
                GOSUB txtfileload
                LOCATE wy + 2, wx + 14: COLOR 1, 7
                PRINT " "; ptxtfile$;
                PRINT SPACE$(13 - LEN(ptxtfile$));
                COLOR 7, 1
        END IF
        IF opx$ = CHR$(9) THEN activew = activew + 1
        IF LEN(opx$) = 2 AND MID$(opx$, 2, 1) = CHR$(15) THEN activew
= activew - 1
        IF LEN(opx$) = 2 AND MID$(opx$, 2, 1) = CHR$(80) THEN
                pfpick = pfpick + 1
                GOSUB changepf
        END IF
        IF LEN(opx$) = 2 AND MID$(opx$, 2, 1) = CHR$(72) THEN
                pfpick = pfpick - 1
                GOSUB changepf
        END IF
        IF activew = 3 THEN
                GOTO selpflp
        ELSE
                dsp = 0: GOSUB pf
                dsp = 1: GOSUB pf
                GOTO selnext
        END IF
        '
changepf:
        IF pfpick > 2 THEN pfpick = 1
        IF pfpick < 1 THEN pfpick = 2
        IF pfpick = 1 THEN
                LOCATE wy + 2, wx + 14: COLOR 1, 7
                IF ptxtfile$ = "-" THEN
                        PRINT SPACE$(14);
                ELSE
                        PRINT " "; ptxtfile$;
                        PRINT SPACE$(13 - LEN(ptxtfile$));
                END IF
                LOCATE wy + 3, wx + 14: COLOR 7, 1
                              Page 13
```

```
                            Veripro
              PRINT " "; pformat$;
              PRINT SPACE$(13 - LEN(pformat$));
        END IF
        IF pfpick = 2 THEN
              LOCATE wy + 2, wx + 14: COLOR 7, 1
              IF ptxtfile$ = "-" THEN
                      PRINT SPACE$(14);
              ELSE
                      PRINT " "; ptxtfile$;
                      PRINT SPACE$(13 - LEN(ptxtfile$));
              END IF
              LOCATE wy + 3, wx + 14: COLOR 1, 7
              PRINT " "; pformat$;
              PRINT SPACE$(13 - LEN(pformat$));
              COLOR 7, 1
        END IF
        RETURN
        '------------------------ selnext:
        IF activew > 4 THEN activew = 1
        IF activew < 1 THEN activew = 4
        IF activew = 1 GOTO seldf
        IF activew = 2 GOTO selef
        IF activew = 3 GOTO selpf
        IF activew = 4 GOTO selcmd
        '
mfini:
        GOSUB svlast
        CLOSE
        END
        '------------------------
        '----- subs --------------
        '------------------------
        '
df:
        wy = 3: wx = 6: WW = 30: WH = 5
        IF dsp = 0 THEN
              COLOR 7, 1: GOSUB frame
              LOCATE wy, wx + 1: PRINT " Data File ";
              LOCATE wy + 2, wx + 1: PRINT "  File Name :
   ";
              LOCATE wy + 3, wx + 1: PRINT "     Format :
   ";
        ELSEIF dsp = 1 THEN
              COLOR 7, 1
              LOCATE wy + 2, wx + 15: PRINT datafile$;
              LOCATE wy + 3, wx + 15: PRINT dformat$;
```

Page 14

```
                        Veripro
        ELSEIF dsp = 2 THEN
                COLOR 1, 7
                LOCATE wy, wx + 1: PRINT " Data File ";
                COLOR 7, 1
        END IF
        RETURN
        '------------------------
ef:
        wy = 9: wx = 6: WW = 30: WH = 5
        IF dsp = 0 THEN
                COLOR 7, 1: GOSUB frame
                LOCATE wy, wx + 1: PRINT " Embosser ";
                LOCATE wy + 2, wx + 1: PRINT " Text File :
";
                LOCATE wy + 3, wx + 1: PRINT "   Line Set :
";
        ELSEIF dsp = 1 THEN
                COLOR 7, 1
                LOCATE wy + 2, wx + 15
                IF etxtfile$ = "-" THEN
                        PRINT SPACE$(13);
                ELSE
                        PRINT etxtfile$;
                END IF
                LOCATE wy + 3, wx + 15: PRINT eformat$;
        ELSEIF dsp = 2 THEN
                COLOR 1, 7
                LOCATE wy, wx + 1: PRINT " Embosser ";
                COLOR 7, 1
        END IF
        RETURN
        '------------------------
pf:
        wy = 15: wx = 6: WW = 30: WH = 5
        IF dsp = 0 THEN
                COLOR 7, 1: GOSUB frame
                LOCATE wy, wx + 1: PRINT " Printer ";
                LOCATE wy + 2, wx + 1: PRINT " Text File :
";
                LOCATE wy + 3, wx + 1: PRINT "   Bar Code :
";
        ELSEIF dsp = 1 THEN
                COLOR 7, 1
                LOCATE wy + 2, wx + 15
                IF ptxtfile$ = "-" THEN
                        PRINT SPACE$(13);
                ELSE
                        PRINT ptxtfile$;
```

```
                            Veripro
                END IF
                LOCATE wy + 3, wx + 15: PRINT pformat$;
        ELSEIF dsp = 2 THEN
                COLOR 1, 7
                LOCATE wy, wx + 1: PRINT " Printer ";
                COLOR 7, 1
        END IF
        RETURN
        '------------------------
ms:
        wysave = wy: wxsave = wx
        COLOR 7, 1: wy = 3: wx = 44: WW = 33: WH = 13
        mswy = wy: mswx = wx
        IF dsp = 0 THEN
                GOSUB frame
                LOCATE wy, wx + 1: PRINT " Match Status ";
                LOCATE wy + 2, wx + 2: PRINT "         Record # ";
                LOCATE wy + 3, wx + 2: PRINT "   Total Records   ";
                LOCATE wy + 7, wx + 2: PRINT "Account # ";
                LOCATE wy + 8, wx + 2: PRINT "    Form = ";
                LOCATE wy + 9, wx + 2: PRINT "     ECR = ";
                LOCATE wy + 10, wx + 2: PRINT "     MAG = ";
                LOCATE wy + 5, wx + 2: PRINT STRING$(29, 196);
        ELSE
                COLOR 7, 1
                LOCATE wy + 2, wx + 18: PRINT SPACE$(7);
                LOCATE wy + 2, wx + 18: PRINT crn;
                LOCATE wy + 3, wx + 18: PRINT SPACE$(7);
                LOCATE wy + 3, wx + 18: PRINT size;
        END IF
        wy = wysave: wx = wxsave
        RETURN
        '------------------------
cmset:
        wy = 21: wx = 6: WW = 30: WH = 11
        IF dsp = 0 THEN
                COLOR 7, 1: GOSUB frame
                LOCATE wy, wx + 1: PRINT " Step Commands ";
                LOCATE wy + 2, wx + 1: PRINT "    1 - Emboss card
";
                LOCATE wy + 3, wx + 1: PRINT "    2 - Print form
";
                LOCATE wy + 4, wx + 1: PRINT "    3 - Read card
";
                LOCATE wy + 5, wx + 1: PRINT "    4 - Read form
";
                LOCATE wy + 6, wx + 1: PRINT "    5 - Insert card
";
```

Page 16

```
                              Veripro
              LOCATE wy + 7, wx + 1: PRINT "    6 - Process form
";
              LOCATE wy + 8, wx + 1: PRINT "    7 - Clear inserter
";
              LOCATE wy + 9, wx + 1: PRINT "    8 - Cycle one record
";
        ELSEIF dsp = 2 THEN
              COLOR 1, 7
              LOCATE wy, wx + 1: PRINT " Step Commands ";
              COLOR 7, 1
        ELSEIF dsp = 3 THEN
              IF stepsel = 1 THEN COLOR 1, 7 ELSE COLOR 7, 1
              LOCATE wy + 2, wx + 4: PRINT " 1 - Emboss card        ";
              IF stepsel = 2 THEN COLOR 1, 7 ELSE COLOR 7, 1
              LOCATE wy + 3, wx + 4: PRINT " 2 - Print form         ";
              IF stepsel = 3 THEN COLOR 1, 7 ELSE COLOR 7, 1
              LOCATE wy + 4, wx + 4: PRINT " 3 - Read card          ";
              IF stepsel = 4 THEN COLOR 1, 7 ELSE COLOR 7, 1
              LOCATE wy + 5, wx + 4: PRINT " 4 - Read form          ";
              IF stepsel = 5 THEN COLOR 1, 7 ELSE COLOR 7, 1
              LOCATE wy + 6, wx + 4: PRINT " 5 - Insert card        ";
              IF stepsel = 6 THEN COLOR 1, 7 ELSE COLOR 7, 1
              LOCATE wy + 7, wx + 4: PRINT " 6 - Process form       ";
              IF stepsel = 7 THEN COLOR 1, 7 ELSE COLOR 7, 1
              LOCATE wy + 8, wx + 4: PRINT " 7 - Clear inserter     ";
              IF stepsel = 8 THEN COLOR 1, 7 ELSE COLOR 7, 1
              LOCATE wy + 9, wx + 4: PRINT " 8 - Cycle one record ";
              COLOR 7, 1
        END IF
        RETURN
        '------------------------
filewin:
        wysave = wy: wxsave = wx
        wy = 17: wx = 42: WH = 12: WW = 37
        GOSUB frame
        CALL pkfile COLOR 7, 1
        FOR rp = 1 TO WH
              LOCATE (wy - 1) + rp, wx: PRINT SPACE$(WW)
        NEXT rp
        wy = wysave: wx = wxsave
        RETURN
        '------------------------
formatwin:
        wysave = wy: wxsave = wx
        wy = 17: wx = 53: WH = 12: WW = 17
        GOSUB frame
                              Page 17
```

```
                         Veripro
        CALL pkformat

COLOR 7, 1
        FOR rp = 1 TO WH
                LOCATE (wy - 1) + rp, wx: PRINT SPACE$(WW)
        NEXT rp
        wy = wysave: wx = wxsave
        RETURN
        '------------------------
frame:
        LOCATE wy, wx
        PRINT CHR$(218);
        NRP = WW - 2: GOSUB frameln
        PRINT CHR$(191);
        '
        LOCATE wy + (WH - 1), wx
        PRINT CHR$(192);
        NRP = WW - 2: GOSUB frameln
        PRINT CHR$(217);
        '
        FOR rp = 1 TO WH - 2
                LOCATE wy + rp, wx
                PRINT CHR$(179);
                PRINT SPACE$(WW - 2);
                PRINT CHR$(179);
        NEXT rp
        '
        RETURN
        '
frameln:
        FOR rp = 1 TO NRP
                PRINT CHR$(196);
        NEXT rp
        RETURN
        '------------------------
        '
svlast:
        OPEN "---ccw.end" FOR OUTPUT AS #9
        PRINT #9, datafile$
        PRINT #9, dformat$
        PRINT #9, etxtfile$
        PRINT #9, eformat$
        PRINT #9, ptxtfile$
        PRINT #9, pformat$
        PRINT #9, crn
        CLOSE #9
        RETURN
        '------------------------
```

Page 18

Veripro

```
rdlast:
        OPEN "---ccw.end" FOR INPUT AS #9
        LINE INPUT #9, datafile$
        LINE INPUT #9, dformat$
        LINE INPUT #9, etxtfile$
        LINE INPUT #9, eformat$
        LINE INPUT #9, ptxtfile$
        LINE INPUT #9, pformat$
        INPUT #9, crn
        CLOSE #9
        RETURN
        '------------------------
        '
getfig:
        OPEN "---ccw.cfg" FOR INPUT AS #9
        LINE INPUT #9, figa$     'directory data
        LINE INPUT #9, figba$    'embosser 1 port
        LINE INPUT #9, figbb$    'embosser 2 port
        LINE INPUT #9, figbc$    'embosser 3 port
        LINE INPUT #9, figbd$    'embosser 4 port
        LINE INPUT #9, figca$    'forms printer port
        LINE INPUT #9, figcb$    'forms printer port
        LINE INPUT #9, figd$     'system printer port
        LINE INPUT #9, fige$     'screen type
        LINE INPUT #9, figf$     'card reader port/type
        LINE INPUT #9, figg$     'directory merge print
        LINE INPUT #9, figh$     'directory merge emboss
        LINE INPUT #9, figi$     'directory card formats
        CLOSE #9
        RETURN
        '------------------------
        '
formatload:
fmload:
        '
        OPEN "NFORMAT.dyn" FOR INPUT AS #9
fml1:   'load embosser format
        INPUT #9, TNT
        '
         FOR rp = 1 TO (TNT * 4) + 4
          INPUT #9, t(rp)
         NEXT rp
        '
        INPUT #9, FID
        bam$ = INPUT$(FID, #9)
        IF bam$ = dformat$ AND t(4) = 2 THEN GOTO fml2
        GOTO fml1
```

Veripro

```
fml2:
        CLOSE #9
        OPEN "NFORMAT.dyn" FOR INPUT AS #9
fml3:   'load printer format
        INPUT #9, TNT
        '
         FOR rp = 1 TO (TNT * 4) + 4
           INPUT #9, tprn(rp)
         NEXT rp
        '
        INPUT #9, FID
        bam$ = INPUT$(FID, #9)
        IF bam$ = dformat$ AND tprn(4) = 1 THEN GOTO fml4
        GOTO fml3
fml4:
        CLOSE #9
        RETURN
        '-------------------------
        '
getdatafile:
        CLOSE #1
        nam$ = pathname$ + "\" + datafile$
        OPEN nam$ FOR RANDOM AS #1 LEN = t(2)
        size = (LOF(1) - t(1)) / t(2)
        size = FIX(size)
        ern = size
        FIELD #1, t(2) AS abcd$
        crn = 1
        RETURN
        '
msshowrec:
        GET #1, crn
        a$ = abcd$
        LOCATE mswy + 2, mswx + 18: PRINT SPACE$(9)
        LOCATE mswy + 2, mswx + 18: PRINT crn;
        filtercardacc$ = MID$(a$, t(5), (t(6) - t(5)) + 1)
        matchcardacc$ = ""
        FOR rp = 1 TO LEN(filtercardacc$)
        IF MID$(filtercardacc$, rp, 1) <> " " THEN
                matchcardacc$ = matchcardacc$ + MID$(filtercardacc$, r
p, 1)
        END IF
        NEXT rp
        LOCATE mswy + 7, mswx + 12: PRINT matchcardacc$;
        RETURN
        '-------------------------
linelocload:
        cardformat$ = pathname$ + "\" + eformat$
```

```
                                        Veripro
        OPEN cardformat$ FOR INPUT AS #6
        LINE INPUT #6, lineloc$
        CLOSE #6
        newlineloc = 1
        RETURN
        '--------------------------
tztfileclear:
        FOR rp = 1 TO 12
                lcard(rp) = SPACE$(240)
        NEXT rp
        RETURN
        '
tztfileload:
        embosstzt$ = figh$ + "\" + etxtfile$
        OPEN embosstzt$ FOR INPUT AS #6
        FOR rp = 1 TO 12
                IF rp < 10 THEN
                        lcard(rp) = INPUT$(30, #6)
                ELSE
                        lcard(rp) = INPUT$(240, #6)
                END IF
        NEXT rp
        CLOSE #6
        RETURN
        '--------------------------
txtfileclear:
        FOR rp = 1 TO 66
                lform(rp) = SPACE$(80)
        NEXT rp
        RETURN
        '
txtfileload:
        pmbosstxt$ = figg$ + "\" + ptxtfile$
        OPEN pmbosstxt$ FOR INPUT AS #6
        FOR rp = 1 TO 66
                lform(rp) = INPUT$(80, #6)
        NEXT rp
        CLOSE #6
        RETURN
        '--------------------------
        '
autoexit:
        autostate = 0
        STOP SUB ccwburst
SHARED motorporta, motorportb, motorportc, motorportr, motormode, moto
rsoff
```

Page 21

```
                            Veripro
SHARED mcardf, mcardr, minsertf, minsertr, mfeed, mform, mflipf, mflip
r
SHARED mcards, minserts, mfeeds, mforms, mflips, mspin, mejectf, mejec
tr
SHARED mburst, mxfer, mspins, mejects, mbursts, mxfers, feedbrk, burst
brk
SHARED snsporta, snsportb, snsportc, snsportr, snsmode, snscardl, snsc
ardr
SHARED snsinsert, snscardp, snspicker, snsfold, snsform, snsspin, snso
utput
SHARED snsreject, snsburst, snsexit, snsflipdn, snsoutdn, snsrotate
SHARED dataporta, dataportb, dataportc, dataportr, datamode, formwasdo
ne
SHARED autostate, brstpline, burstcmd, burststatus, mswy, mswx, burste
rr$
SHARED autoemb, autolpt, ppsftime, ppstate '
          DIM bcdata(100)
          '
          'ccw-brst.bas
          'form burst/bcread controller
          '
          'enter with    burstcmd = 0 get status
          '                         1 burst and read form
          '                         2 home burster
          '                         3 clear burst station
          '
          'return with burststatus = 0 ready
          '                          1 bursting
          '                          2 data ready
          '                          3 error
          '                          4 form not ready
          '
          '     bcdataf$ = ascii account number printed (foward)
          '     bcdatar$ = ascii account number printed (reverse)
          '     bursterr$ = ascii error message
          '
          '------------------------
          '
          IF burstcmd = 0 GOTO getbstat
          IF burstcmd = 1 THEN
                  IF brstpline = 0 GOTO readform
                  IF brstpline = 1 GOTO cbs1
                  IF brstpline = 2 GOTO cbs2
                  IF brstpline = 3 GOTO cbs3
          END IF
          IF burstcmd = 2 THEN
```

```
                              Veripro
                IF brstpline = 0 GOTO bursthome
                IF brstpline = 6 GOTO cbs6
                IF brstpline = 7 GOTO cbs7
        END IF
        IF burstcmd = 3 GOTO burstclr
        EXIT SUB
        '
        '------------------------
        '---------- get status ---
        '------------------------
getbstat:
        IF pstate = 1 THEN EXIT SUB
        IF errorstat = 1 THEN
                burststatus = 3
                EXIT SUB
        END IF
        IF errorstat = 0 THEN
                IF datastat = 0 THEN
                        burststatus = 0
                        EXIT SUB
                ELSE
                        burststatus = 2
                        EXIT SUB
                END IF
        END IF
        EXIT SUB
        '
        '------------------------
        '---------- read form ----
        '------------------------
readform:
        '
        '
cbs1:   pstate = 1: datastat = 0
        brstpline = 1: burststatus = 1
        timeout = TIMER + 4
        '
        GOSUB burstfw                                   'start burst
        '
cbs12:
        IF INP(snsportc) AND snsburst THEN
                GOTO cbs2
        ELSE
                IF TIMER > timeout THEN
                        GOSUB burststop
                        pstate = 0
                        burststatus = 3
                        errorstat = 1
```

```
                                Veripro
                    bursterr$ = "Burst timeout"
                    EXIT SUB                                 'error exit
                END IF
            END IF
            GOTO cbs12
            '
    cbs2:   'wait for burst home
            brstpline = 2
            IF INP(snsportc) AND snsburst THEN
                    IF TIMER > timeout THEN
                            GOSUB burststop
                            pstate = 0
                            burststatus = 3
                            errorstat = 1
                            bursterr$ = "Burst timeout"
                            EXIT SUB                         'error exit
                    ELSE
                            GOTO cbs2
                    END IF
            END IF
            '
            GOSUB burststop
            GOSUB fbackup
            brstpline = 3: burststatus = 1
            '
    cbs3:   'get bar code data from HPCR-1800
            '
            bursterr$ = ""
            LOCATE 38, 10: PRINT SPACE$(25);
            LOCATE 39, 10: PRINT SPACE$(25);
            GOSUB bcadjust
            IF MID$(bcaccount$, 1, 1) = "0" THEN bcodd = 3 ELSE bcodd = 2
            bcmatch$ = MID$(bcaccount$, bcodd, LEN(bcaccount$) - (bcodd +
    1))
            'LOCATE 38, 10: PRINT LEN(bcaccount$)
            GOSUB bcadjust
            'LOCATE 39, 10: PRINT bcaccount$
            '
            LOCATE mswy + 8, mswx + 12: PRINT bcmatch$;
            '
            burststatus = 0: pstate = 0: brstpline = 0
            autolpt = 3
            EXIT SUB                                         'exit (done)
            '
            '------------------------
            '----- home burster -------
            '------------------------
    bursthome:
```

```
                                    Veripro
            pstate = 1: datastat = 0
            brstpline = 6: burststatus = 1
            '
            brrtimeout = TIMER + 3
            GOSUB burstfw
            '
cbs6:       'look for burst home
            IF INP(snsportc) AND snsburst THEN
                    IF TIMER > timeout THEN
                            GOSUB burststop
                            pstate = 0
                            burststatus = 3
                            errorstat = 1
                            bursterr$ = "Burst timeout"
                            EXIT SUB                        'error exit
                    ELSE
                            EXIT SUB                        'running exi
t
                    END IF
            END IF
            GOSUB burststop
            burststatus = 0: pstate = 0: brstpline = 0
            EXIT SUB                                        'exit (done)
            '
            '-------------------------
            '-- clear burst station --
            '-------------------------
burstclr:
            pstate = 1: datastat = 0
            brstpline = 7: burststatus = 1
            starttime = TIMER: timeout = starttime + 3
            GOSUB bsfeed
            bcls = TIMER + .3
bclstall:   IF TIMER < bcls GOTO bclstall
            '
cbs7:       'wait for form present to clear
            IF INP(snspordb) AND snsform THEN
                    GOSUB bsfeeds
                    pstate = 0
                    burststatus = 0
                    EXIT SUB
            ELSE
                    IF TIMER > timeout THEN
                            GOSUB bsfeeds
                            pstate = 0
                            burststatus = 3
                            errorstat = 1
                            bursterr$ = "Burst timeout"
                        Page 25
```

```
                        Veripro
              EXIT SUB                          'error exit
        END IF
    END IF
    '
    '--------------------------
    '----- subs --------------
    '--------------------------
    '
bcadjust:
    bctimeout = TIMER + .2: bcaccount$ = ""
dspbc:
    OUT dataportc, &HF6                         'set datardy low
dwrlop:
    IF INP(dataportc) AND &H10 THEN             'look for strobe low
        IF TIMER > bctimeout THEN
            bcaccount$ = "No Bar Code Data"
            RETURN
        END IF
        GOTO dwrlop
    END IF
    '
    bcbite = INP(dataporta)
    OUT dataportc, &HFF                         'set datardy high
    '
    bcbite = bcbite AND &HF
    bcaccount$ = bcaccount$ + RTRIM$(LTRIM$(STR$(bcbite)))
    bcchr = bcchr + 1
    IF bcbite = 13 THEN RETURN
    GOTO dspbc
    '------------------------
    '
burststop:
    motordb = INP(motorportb)
    motordb = motordb OR mbursts
    motordb = motordb AND burstbrk
    OUT motorportb, motordb
    stalltm = TIMER + .3
bsstall: IF TIMER < stalltm GOTO bsstall
    motordb = INP(motorportb)
    motordb = motordb OR &H80
    OUT motorportb, motordb
    RETURN
    '
burstfw:
    motordb = INP(motorportb)
    motordb = motordb OR mbursts
    motordb = motordb AND mburst
    OUT motorportb, motordb
```

Veripro
```
            RETURN
            '
            '
bsfeed:
            mototdb = INP(motorporta)
            motordb = motordb OR mfeeds
            motordb = motordb AND mfeed
            OUT motorporta, motordb
            RETURN
            '
bsfeeds:
            mototdb = INP(motorporta)
            motordb = motordb OR mfeeds
            OUT motorporta, motordb
            RETURN
            '
            '-----------------------------
fbackup:    'burst is done so backup form into printer
            IF formwasdone <> 1 THEN RETURN
            formwasdone = 2
            '
            FOR rp = 1 TO 21
                    PRINT #4, CHR$(27) + "A" + CHR$(20);
                    'PRINT #4, CHR$(27) + "2";
                    PRINT #4, CHR$(27) + "]";
            NEXT rp
            'FOR rp = 1 TO 180
            '        PRINT #4, CHR$(27) + CHR$(106) + CHR$(1);
            'NEXT rp
            '
            'PRINT #4, CHR$(27) + "A" + CHR$(10);
            PRINT #4, CHR$(27) + "2";
            '
            backstall = TIMER + 1.5
            DO WHILE TIMER < backstall: LOOP
            'send ff to set new top of form
            PRINT #4, CHR$(12);
            '
            RETURN
'------
END SUB SUB ccwclear
SHARED motorporta, motorportb, motorportc, motorportr, motormode, moto
rsoff
SHARED mcardf, mcardr, minsertf, minsertr, mfeed, mform, mflipf, mflip
r
SHARED mcards, minserts, mfeeds, mforms, mflips, mspin, mejectf, mejec
```

```
                              Veripro
tr
SHARED mburst, mxfer, mspins, mejects, mbursts, mxfers, feedbrk, burst
brk
SHARED snsporta, snsportb, snsportc, snsportr, snsmode, snscardl, snsc
ardr
SHARED snsinsert, snscardp, snspicker, snsfold, snsform, snsspin, snso
utput
SHARED snsreject, snsburst, snsexit, snsflipdn, snsoutdn, snsrotate
SHARED dataporta, dataportb, dataportc, dataportr, datamode
SHARED formwasdone, autoemb, autolpt, autostate
        '
        '-------------------------
100     'clear and reset inserter
        '
        dbdb = INP(dataportc)              'reset hbcr1800
        dbdb = dbdb OR &01
        OUT dataportc, dbdb
        bcrstime = TIMER + .1
        DO WHILE TIMER < bcrstime: LOOP
        dbdb = INP(dataportc)
        dbdb = dbdb AND &HFE
        OUT dataportc, dbdb
        '
        spinerhome = 0
        mcmd = minsertr: mport = motorporta: mgo = 1: GOSUB mctrl
        dlay = .5: GOSUB stall
200
        statusb = INP(snsportb)
        statusc = INP(snsportc)
        GOSUB snsdsp
        '
        'insert home
        '
        IF snsinsert AND statusb THEN
                mcmd = minserts: mport = motorporta: mgo = 0: GOSUB mc
trl
        ELSE
                mcmd = minsertr: mport = motorporta: mgo = 1: GOSUB mc
trl
        END IF
        '
        'flip home
        '
        IF snsfold AND statusb THEN
                mcmd = mflipr: mport = motorporta: mgo = 1: GOSUB mctr
l
        ELSE
```

Page 28

```
                    Veripro
        mcmd = mflips: mport = motorporta: mgo = 0: GOSUB mctr
l
    END IF
    '
    'burst home
    '
    IF snsburst AND statusc THEN
        mcmd = mburst: mport = motorportb: mgo = 1: GOSUB mctr
l
    ELSE
        mcmd = mbursts: mport = motorportb: mgo = 0: GOSUB mct
rl
    END IF
    '
    'output home
    '
    IF snsoutput AND statusc THEN
        mcmd = mejectr: mport = motorportb: mgo = 1: GOSUB mct
rl
    ELSE
        mcmd = mejects: mport = motorportb: mgo = 0: GOSUB mct
rl
    END IF
    '
    'picker home
    '
    IF snsinsertb AND statusb THEN
    IF snspicker AND statusb THEN
        mcmd = mcardr: mport = motorporta: mgo = 1: GOSUB mctr
l
    ELSE
        mcmd = mcards: mport = motorporta: mgo = 0: GOSUB mctr
l
    END IF
    END IF
    '
    'spinner home
    '
    IF snsoutput AND statusc THEN GOTO spinernot
    IF spinerhome = 1 GOTO spinernot
    IF snsspin AND statusb THEN
        mcmd = mspin: mport = motorportb: mgo = 1: GOSUB mctrl
    ELSE
        mcmd = mspins: mport = motorportb: mgo = 0: GOSUB mctr
l
        spinerhome = 1
    END IF
spinernot:
```

Page 29

```
                            Veripro
'
'test for init exit
'
teststat = statusb AND &H34
IF teststat <> &H4 GOTO 200
teststat = statusc AND &H7
IF teststat <> &H2 GOTO 200
IF spinerhome <> 1 GOTO 200
'
'test card track clear
'
cltksw = 0
teststat = INP(snsportb) AND &HB
IF teststat = &HB THEN GOTO 250
mcmd = mcardf: mport = motorporta: mgo = 1: GOSUB mctrl
cltksw = 1
250
        '
        'test for form and clear it
        '
        IF INP(snsportb) AND snsform THEN
                mcmd = mfeed: mport = motorporta: mgo = 1: GOSUB mctrl
                dlay = .5: GOSUB stall
                mcmd = mfeeds: mport = motorporta: mgo = 0: GOSUB mctrl
        END IF
        IF INP(snsportb) AND snsform THEN GOTO resetdone
        '
        'form present clear it
        '
        mcmd = mfeed: mport = motorporta: mgo = 1: GOSUB mctrl
        mcmd = mform: mport = motorporta: mgo = 1: GOSUB mctrl
        dlay = 3.5: GOSUB stall
        IF cltksw = 1 THEN
                mcmd = mcards: mport = motorporta: mgo = 0: GOSUB mctrl
                mcmd = mcardr: mport = motorporta: mgo = 1: GOSUB mctrl
                cltksw = 2
        END IF
        mcmd = mflipf: mport = motorporta: mgo = 1: GOSUB mctrl
        mcmd = mfeeds: mport = motorporta: mgo = 0: GOSUB mctrl
        mcmd = mforms: mport = motorporta: mgo = 0: GOSUB mctrl
        timeout = TIMER + 2
flipback:
        IF INP(snsportc) AND snsflipdn THEN
                IF TIMER > timeout GOTO flipfail
                GOTO flipback
```

Page 30

```
                            Veripro
        ELSE
flipfail:
                mcmd = mflips: mport = motorporta: mgo = 0: GOSUB mctrl
                mcmd = mflipr: mport = motorporta: mgo = 1: GOSUB mctrl
        END IF
        '
tlop1:  IF snspicker AND INP(snsportb) THEN
                GOTO tlop11
        ELSE
                mcmd = mcards: mport = motorporta: mgo = 0: GOSUB mctrl
                cltksw = 0
        END IF
tlop11: IF INP(snsportb) AND snsfold THEN
                GOTO tlop1
        ELSE
        mcmd = mflips: mport = motorporta: mgo = 0: GOSUB mctrl
        END IF
        IF cltksw > 0 GOTO tlop1
        '
        GOSUB spincycle
        'GOSUB ejectcycle
        GOSUB rejectcycle
        GOSUB spincycle
resetdone:
        IF cltksw = 1 THEN
                dlay = 2: GOSUB stall
                mcmd = mcards: mport = motorporta: mgo = 0: GOSUB mctrl
                mcmd = mcardr: mport = motorporta: mgo = 1: GOSUB mctrl
tlop2:          IF snspicker AND INP(snsportb) THEN
                GOTO tlop2
                ELSE
                mcmd = mcards: mport = motorporta: mgo = 0: GOSUB mctrl
                cltksw = 0
                END IF
        END IF '-----------------------------------------
        OUT motorporta, motorsoff
        OUT motorportb, motorsoff
        OUT motorportc, motorsoff
        '-----------------------------------------
        BEEP    'inserter ready
                            Page 31
```

```
                          Veripro
        '
        '
        GOTO ccwclfini
        '----------------------------------------
        '------------- sub programs -------------
        '----------------------------------------
        '----------------------------------------
stall:  'real time delay loop. enter with dlay=xxxx.xx seconds
        '
        dlayval = TIMER
stalloop:
        IF TIMER < dlayval + dlay GOTO stalloop
        RETURN
        '----------------------------------------
snsdsp: 'sensor display
        RETURN
        snsdsp$ = "": off$ = " Off ": on$ = " On  "
        snsdb = INP(snsportb)
        IF snsdb AND snscardl THEN snsdsp$ = snsdsp$ + off$ ELSE snsds
p$ = snsdsp$ + on$
        IF snsdb AND snscardr THEN snsdsp$ = snsdsp$ + off$ ELSE snsds
p$ = snsdsp$ + on$
        IF snsdb AND snsinsert THEN snsdsp$ = snsdsp$ + off$ ELSE snsd
sp$ = snsdsp$ + on$
        IF snsdb AND snscardp THEN snsdsp$ = snsdsp$ + off$ ELSE snsds
p$ = snsdsp$ + on$
        IF snsdb AND snspicker THEN snsdsp$ = snsdsp$ + off$ ELSE snsd
sp$ = snsdsp$ + on$
        IF snsdb AND snsfold THEN snsdsp$ = snsdsp$ + off$ ELSE snsdsp
$ = snsdsp$ + on$
        IF snsdb AND snsform THEN snsdsp$ = snsdsp$ + off$ ELSE snsdsp
$ = snsdsp$ + on$
        IF snsdb AND snsspin THEN snsdsp$ = snsdsp$ + off$ ELSE snsdsp
$ = snsdsp$ + on$
        snsdb = INP(snsportc)
        IF snsdb AND snsoutput THEN snsdsp$ = snsdsp$ + off$ ELSE snsd
sp$ = snsdsp$ + on$
        IF snsdb AND snsreject THEN snsdsp$ = snsdsp$ + off$ ELSE snsd
sp$ = snsdsp$ + on$
        IF snsdb AND snsburst THEN snsdsp$ = snsdsp$ + off$ ELSE snsds
p$ = snsdsp$ + on$
        '
        LOCATE 5, 7
        FOR rp = 1 TO 11
        IF MID$(snsdsp$, (rp * 5) - 4, 5) = off$ THEN COLOR 7, 4 ELSE
COLOR 7, 2
        PRINT MID$(snsdsp$, (rp * 5) - 4, 5); : COLOR 7, 0: PRINT SPAC
E$(1);
```

Page 32

```
                              Veripro
        NEXT rp
        '
        RETURN
        '----------------------------------------
mctrl:  'motor control loop.
        'enter with mcmd=[command var name]
        '            mport=motorportx (x=a,b,c)
        '              go=x (x=0/stop x=1/go)
        '
        mword = INP(mport)
        IF mgo = 1 THEN
                nword = mword AND mcmd
        ELSE
                nword = mword OR mcmd
        END IF
        OUT mport, nword
        RETURN
        '----------------------------------------
        'spincycle or one rev of the spinner
spincycle:
        mcmd = mspin: mport = motorportb: mgo = 1: GOSUB mctrl
spinl1:
        IF snsspin AND INP(snsportb) THEN
                GOTO spinl1
        ELSE
                mcmd = mspins: mport = motorportb: mgo = 0: GOSUB mctr
l
                spinerhome = 1
        END IF
        RETURN
        '----------------------------------------
        'reject cycle. move output to reject pos then home
rejectcycle:
        mcmd = mejectf: mport = motorportb: mgo = 1: GOSUB mctrl
rejl1:
        IF snsreject AND INP(snsportc) THEN
                GOTO rejl1
        ELSE
                mcmd = mejects: mport = motorportb: mgo = 0: GOSUB mct
rl
        END IF
        mcmd = mejectr: mport = motorportb: mgo = 1: GOSUB mctrl
rejl2:
        IF snsoutput AND INP(snsportc) THEN
                GOTO rejl2
        ELSE
                mcmd = mejects: mport = motorportb: mgo = 0: GOSUB mct
rl Page 33
```

```
                          Veripro
        END IF
        RETURN
        '----------------------------------------
        'eject cycle. move to output then home
ejectcycle:
        mcmd = mejectf: mport = motorportb: mgo = 1: GOSUB mctrl
        timeout = TIMER + 2
eejl1:
        IF snsoutdn AND INP(snsportc) THEN
                IF TIMER > timeout GOTO eefail
                GOTO eejl1
        ELSE
eefail:         mcmd = mxfer: mport = motorportb: mgo = 1: GOSUB mctrl
                dlay = .4: GOSUB stall
                mcmd = mejects: mport = motorportb: mgo = 0: GOSUB mct
rl
        END IF
        mcmd = mejectr: mport = motorportb: mgo = 1: GOSUB mctrl
eejl2:
        IF snsoutput AND INP(snsportc) THEN
                GOTO eejl2
        ELSE
                mcmd = mejects: mport = motorportb: mgo = 0: GOSUB mct
rl
        END IF
eejl3:
        IF snsexit AND INP(snsportc) THEN GOTO eejl3
eejl4:
        IF snsexit AND INP(snsportc) THEN
                dlay = .5: GOSUB stall
                mcmd = mxfers: mport = motorportb: mgo = 0: GOSUB mctr
l
                GOTO eeend
        ELSE
                GOTO eejl4
        END IF
eeend:
        RETURN
        '----------------------------------------
canmsg:
        LOCATE 6, 7: PRINT "Card   Card   Inst. Card   Pick   Fold   Form
Spin  OutP  Rej.  Burst";
        LOCATE 7, 7: PRINT "Left   Right        Ready  Home   Home   Ready
Home           Home";
        RETURN
        '----------------------------------------
ccwclfini:
        formwasdone = 0: autoemb = 0: autolpt = 0
                          Page 34
```

Veripro
```
END SUB

SUB ccwct
SHARED motorporta, motorportb, motorportc, motorportr, motormode, moto
rsoff
SHARED mcardf, mcardr, minsertf, minsertr, mfeed, mform, mflipf, mflip
r
SHARED mcards, minserts, mfeeds, mforms, mflips, mspin, mejectf, mejec
tr
SHARED mburst, mxfer, mspins, mejects, mbursts, mxfers, feedbrk, burst
brk
SHARED snsporta, snsportb, snsportc, snsportr, snsmode, snscardl, snsc
ardr
SHARED snsinsert, snscardp, snspicker, snsfold, snsform, snsspin, snso
utput
SHARED snsreject, snsburst, snsexit, snsflipdn, snsoutdn, snsrotate
SHARED dataporta, dataportb, dataportc, dataportr, datamode
SHARED ctpline, cardcmd, cardstatus, cdtimeout
SHARED ecrbite, mswy, mswx, autostate
SHARED crderr$, account$, ecrchr$ ,
        DIM adj(100)
        DIM rawecr(8192)
        DIM bittimes(600)
        DIM magbits(400)
        DIM aba(40)
        '
        'ccw-ct.bas
        'card track controller
        '
        'enter with   cardcmd = 0 get status
        '                       1 read card
        '                       2 home card track
        '                       3 clear card track
        '
        'return with cardstatus = 0 ready
        '                         1 reading card
        '                         2 data ready
        '                         3 error
        '                         4 card not ready
        '                         5 data ready & done
        '
        '       ecrdata$ = ascii account number embossed
        '       magdata$ = ascii account number encoded
        '       carderr$ = ascii error message
        '
        '-----------------------
```

Page 35

```
                         Veripro
        '
        IF cardcmd = 0 GOTO getstat
        IF cardcmd = 1 THEN
                IF ctpline = 0 GOTO readcard
                IF ctpline = 1 GOTO cs1
                IF ctpline = 2 GOTO cs2
                IF ctpline = 3 GOTO cs3
                IF ctpline = 4 GOTO cs4
                IF ctpline = 5 GOTO cs5
        END IF
        IF cardcmd = 2 THEN
                IF ctpline = 0 GOTO trackhome
                IF ctpline = 6 GOTO cs6
                IF ctpline = 7 GOTO cs7
        END IF
        IF cardcmd = 3 GOTO trackclr
        EXIT SUB
        '
        '------------------------
        '---------- get status ---
        '------------------------
getstat:
        IF pstate = 1 THEN EXIT SUB
        IF errorstat = 1 THEN
                cardstatus = 3
                EXIT SUB
        END IF
        IF errorstat = 0 THEN
                IF datastat = 0 THEN
                        cardstatus = 0
                        EXIT SUB
                ELSE
                        cardstatus = 2
                        EXIT SUB
                END IF
        END IF
        EXIT SUB
        '
        '------------------------
        '---------- read card ----
        '------------------------
readcard:
        pstate = 1: datastat = 0
        ctpline = 1: cardstatus = 1
        cdtimeout = TIMER + 3
        '
cs1:    'look for picker home
        IF INP(snsportb) AND &H10 THEN
```

```
                           Veripro
            GOSUB pickrev                          'picker not ho
me
            IF TIMER > cdtimeout THEN
                    GOSUB pickstop
                    pstate = 0
                    cardstatus = 3
                    errorstat = 1
                    crderr$ = "Picker timeout. (CS1)"
                    ctpline = 0
                    EXIT SUB                       'error exit
            ELSE
                    EXIT SUB                       'running exi
t
            END IF
        END IF
        '
        GOSUB pickstop
        '
        'test for card track full
        IF INP(snsportb) AND &H1 GOTO cs2          'good to go
        pstate = 0
        cardstatus = 3
        errorstat = 1
        crderr$ = "Card track full. (CS1)"
        ctpline = 0
        EXIT SUB                                   'error exit
        '
cs2:    'wait for card present
        ctpline = 2
        IF INP(snsportb) AND &H8 THEN
                crderr$ = "Waiting for card."
                cardstatus = 4
                EXIT SUB                           'running exi
t
        END IF
        '
        GOSUB pickfw
        ctpline = 3: cardstatus = 1
        cdtimeout = TIMER + 3
        '
cs3:    'look for card under ecr head
        gethead = INP(dataportb)
        gethead = gethead AND &HF
        IF gethead > 0 THEN
                IF TIMER > cdtimeout THEN
                        GOSUB pickstop
                        pstate = 0
                        cardstatus = 3
                           Page 37
```

```
                              Veripro
                    errorstat = 1
                    crderr$ = "Picker timeout. (CS3)"
                    ctpline = 0
                    EXIT SUB                            'error exit
              ELSE
                    cardstatus = 1
                    EXIT SUB                            'wati exit
              END IF
         END IF
cs31:
         '
         ctpline = 4: cardstatus = 1: ecrbite = 1
         'cs4: --- collect raw ecr -------------------------
         'DO WHILE ecrbite < 4096                                '
         'rawecr(ecrbite) = INP(dataportb)                       '
         'ecrbite = ecrbite + 1                                  '
         'LOOP                                                   '
cs43:    'IF TIMER > cdtimeout GOTO cs42                         '
         'IF INP(snsportb) AND &H1 GOTO cs43 ELSE GOTO cs41      '
         '--------------------------------------------------
cs4:     'collect raw ecr ---------------------------------
         rawecr(ecrbite) = INP(dataportb)                        '
         ecrbite = ecrbite + 1                                   '
         IF TIMER > cdtimeout GOTO cs42                          '
         IF INP(snsportb) AND &H1 GOTO cs4 ELSE GOTO cs41        '
         '--------------------------------------------------
         '
cs42:    GOSUB pickstop
         pstate = 0
         cardstatus = 3
         errorstat = 1
         crderr$ = "Picker timeout. (CS4)"
         ctpline = 0
         EXIT SUB                            'error exit
         '
cs41:
         GOSUB pickrev
         GOSUB ecradjust
         'GOSUB magadjust
         '
         datastat = 1
         ctpline = 5: cardstatus = 2
         cdtimeout = TIMER + 3
cs5:
         IF INP(snsportb) AND &H10 THEN
                   IF TIMER > cdtimeout THEN
                            GOSUB pickstop
                            pstate = 0
```

Page 38

```
                            Veripro
                    cardstatus = 3
                    errorstat = 1
                    crderr$ = "Picker timeout (CS5)"
                    ctpline = 0
                    EXIT SUB                            'error exit
            ELSE
                    EXIT SUB                            'running exit
            END IF
    END IF
    GOSUB pickstop
    cardstatus = 0: pstate = 0: ctpline = 0
    EXIT SUB                                            'exit (done)
    '
    '------------------------
    '----- home picker -------
    '------------------------
trackhome:
    pstate = 1: datastat = 0
    ctpline = 6: cardstatus = 1
    cdtimeout = TIMER + 3
    GOSUB pickrev
cs6:    'look for picker home
    IF INP(snsportb) AND &H10 THEN
            IF TIMER > cdtimeout THEN
                    GOSUB pickstop
                    pstate = 0
                    cardstatus = 3
                    errorstat = 1
                    crderr$ = "Picker timeout"
                    EXIT SUB                            'error exit
            ELSE
                    EXIT SUB                            'running exit
            END IF
    END IF
    GOSUB pickstop
    cardstatus = 0: pstate = 0: ctpline = 0
    EXIT SUB                                            'exit (done)
    '
    '------------------------
    '----- clear card track --
    '------------------------
trackclr:
    pstate = 1: datastat = 0
    ctpline = 7: cardstatus = 1
    cdtimeout = TIMER + 3
    GOSUB pickfw
```

Page 39

```
                                        Veripro
cs7:    'move picker to end of card track
        IF TIMER > cdtimeout THEN
                cardcmd = 2
                GOTO trackhome                                  'exit from trackhome
        ELSE
                EXIT SUB                                        'running exit
        END IF
        '
        '------------------------
        '----- subs --------------
        '------------------------
        '
pickstop:
        motordb = INP(motorporta)
        motordb = motordb OR mcards
        OUT motorporta, motordb
        RETURN
        '
pickfw:
        motordb = INP(motorporta)
        motordb = motordb OR mcards
        motordb = motordb AND mcardf
        OUT motorporta, motordb
        RETURN
pickrev:
        motordb = INP(motorporta)
        motordb = motordb OR mcards
        motordb = motordb AND mcardr
        OUT motorporta, motordb
        RETURN
        '
        '
        '----------------------------------------
ecradjust:
        '
        ecrpointer = 0
        account$ = ""
ecralop:                                                        'skip to first byte
        chrdig = 0: dspcount = 1
        ecrpointer = ecrpointer + 1
        headdat = rawecr(ecrpointer) AND &HF
        IF headdat = 0 GOTO ecralop
ecrblop:                                                        'load adjust array
        chrdig = chrdig + 1
```

Page 40

```
                            Veripro
        IF chrdig > 90 GOTO ecrfini                  'k was 90 at 1
/2s
        adj(chrdig) = rawecr(ecrpointer)
        ecrpointer = ecrpointer + 1
        headdat = rawecr(ecrpointer) AND &HF
        IF headdat > 0 GOTO ecrblop
        '
        GOSUB adjme                                  'adjust raw in
  adj
        account$ = ecrchr$ + account$
        '
        GOTO ecralop
ecrfini:
        LOCATE 38, 50: PRINT "ECR samples ="; ecrbite;
        LOCATE mswy + 9, mswx + 12: PRINT account$;
        '
        'OPEN "ecrmag.raw" FOR OUTPUT AS #6
        'FOR rp = 1 TO 8192
        '        PRINT #6, rawecr(rp)
        'NEXT rp
        'CLOSE #6
        '
        RETURN
        '-----
adjme:
        w1 = 0: w2 = 0: w3 = 0
        w2loc = INT(chrdig / 2) - 3
        w1loc = INT(chrdig - 9)
        '
        FOR rp = 1 TO 8                              'was 8
                w3 = w3 OR adj(rp + 4)
        NEXT rp
        w3 = w3 AND &HF
        '
        FOR rp = 1 TO 6                              'was 6
                w2 = w2 OR adj(rp + w2loc)
        NEXT rp
        w2 = w2 AND &HF
        '
        FOR rp = 1 TO 8                              'was 8
                w1 = w1 OR adj(rp + (w1loc - 4))
        NEXT rp
        w1 = w1 AND &HF
        '
adjadj:
        ecrchr$ = "x"
        IF w3 = &H4 AND w2 = &HF AND w1 = &H7 THEN ecrchr$ = "4"
        IF w3 + &H4 AND w2 = &H4 AND w1 = &H7 THEN ecrchr$ = "4"
                            Page 41
```

```
                              Veripro
        IF w3 = &H7 AND w2 = &H5 AND w1 = &HD THEN ecrchr$ = "2"
        IF w3 = &HC AND w2 = &H4 AND w1 = &HF THEN ecrchr$ = "6"
        IF w3 = &HD AND w2 = &H5 AND w1 = &H7 THEN ecrchr$ = "5"
        IF w3 = &HF AND w2 = &H1 AND w1 = &H1 THEN ecrchr$ = "7"
        IF w3 = &HF AND w2 = &H1 AND w1 = &HF THEN ecrchr$ = "0"
        IF w3 = &HF AND w2 = &H5 AND w1 = &H1 THEN ecrchr$ = "3"
        IF w3 = &HE AND w2 = &H5 AND w1 = &H1 THEN ecrchr$ = "3"
        IF w3 = &HF AND w2 = &H5 AND w1 = &H7 THEN ecrchr$ = "9"
        IF w3 = &HF AND w2 = &H5 AND w1 = &HF THEN ecrchr$ = "8"
        IF w3 = &HB AND w2 = &H5 AND w1 = &HB THEN ecrchr$ = "8"
        IF w3 = &HF AND w2 = &HF AND w1 = &HF THEN ecrchr$ = "1"
        '
adjfini:
        RETURN
        '-----------------------------------
magadjust:
        magbone = 1: bitnum = 1
magain:
        IF rawecr(magbone) AND &H80 THEN
                GOTO mup
        ELSE
                GOTO mdown
        END IF
        '--------------------
mup:
        bitsize = 1
        DO WHILE rawecr(magbone) AND &H80
                magbone = magbone + 1
                bitsize = bitsize + 1
                IF bitsize > 20 GOTO mloopb
        LOOP
        GOTO mloopa
mdown:
        bitsize = 1
        DO UNTIL rawecr(magbone) AND &H80
                magbone = magbone + 1
                bitsize = bitsize + 1
                IF bitsize > 20 GOTO mloopb
        LOOP
        GOTO mloopa
        '
mloopa:
        bittimes(bitnum) = bitsize
        bitnum = bitnum + 1
        GOTO magain
        '--------------------
mloopb:
        IF bitnum = 1 GOTO magnd
```

Page 42

```
                            Veripro
        bitnum = bitnum - 2
        '
        'find first one bit
        DO UNTIL bittimes(bitnum - 1) < bittimes(bitnum) - 4
                bitnum = bitnum - 1
                IF bitnum < 1 GOTO magerr
        LOOP
        '
        bitnum = bitnum - 1      'first onebit
        '
        magbits(1) = 1
        mbit = 2
onebits:
        IF bittimes(bitnum - 2) < bittimes(bitnum - 1) + 3 THEN
                magbits(mbit) = 1
                mbit = mbit + 1
                bitnum = bitnum - 2
                IF bitnum < 4 GOTO gotbits
        ELSE
                magbits(mbit) = 0
                mbit = mbit + 1
                bitnum = bitnum - 2
                IF bitnum < 4 GOTO gotbits
                GOTO zerobits
        END IF
        GOTO onebits
zerobits:
        IF bittimes(bitnum - 1) > bittimes(bitnum) - 5 THEN
                magbits(mbit) = 0
                mbit = mbit + 1
                bitnum = bitnum - 1
                IF bitnum < 4 GOTO gotbits
        ELSE
                magbits(mbit) = 1
                mbit = mbit + 1
                bitnum = bitnum - 1
                IF bitnum < 4 GOTO gotbits
                GOTO onebits
        END IF
        GOTO zerobits
        '
gotbits:
        FOR rp = 1 TO 40: aba(rp) = 0: NEXT rp
        mchr = 1: mchrbit = 1: mtit = 1
magasci:
        SELECT CASE mchrbit
                CASE IS = 1
                        IF magbits(mtit) = 1 THEN Page 43
```

```
                        Veripro
                            aba(mchr) = aba(mchr) OR &H1
                    END IF
            CASE IS = 2
                    IF magbits(mtit) = 1 THEN
                            aba(mchr) = aba(mchr) OR &H2
                    END IF
            CASE IS = 3
                    IF magbits(mtit) = 1 THEN
                            aba(mchr) = aba(mchr) OR &H4
                    END IF
            CASE IS = 4
                    IF magbits(mtit) = 1 THEN
                            aba(mchr) = aba(mchr) OR &H8
                    END IF
            CASE IS = 5
                    IF magbits(mtit) = 1 THEN
                            aba(mchr) = aba(mchr) OR &H10
                    END IF
        END SELECT
        mchrbit = mchrbit + 1
        mtit = mtit + 1
        IF mchrbit > 5 THEN
                mchrbit = 1
                IF aba(mchr - 1) = &H1F GOTO magaba
                mchr = mchr + 1
        END IF
        IF mchr > 40 GOTO magaba
        GOTO magasci
        '
magaba:
        rp = 0: magacc$ = ""
        DO UNTIL rp = mchr
        SELECT CASE aba(rp)
                CASE IS = &H1
                        magacc$ = magacc$ + "1"
                CASE IS = &H2
                        magacc$ = magacc$ + "2"
                CASE IS = &H13
                        magacc$ = magacc$ + "3"
                CASE IS = &H4
                        magacc$ = magacc$ + "4"
                CASE IS = &H15
                        magacc$ = magacc$ + "5"
                CASE IS = &H16
                        magacc$ = magacc$ + "6"
                CASE IS = &H7
                        magacc$ = magacc$ + "7"
                CASE IS = &H8
```

Veripro

```
                            magacc$ = magacc$ + "8"
            CASE IS = &H19
                            magacc$ = magacc$ + "9"
            CASE IS = &H10
                            magacc$ = magacc$ + "0"
            CASE IS = &HB
                            magacc$ = magacc$ + ";"
            CASE IS = &HD
                            magacc$ = magacc$ + "="
            CASE IS = &H1F
                            magacc$ = magacc$ + "?"
        END SELECT
        rp = rp + 1
        LOOP
        'magacc$ = magacc$ + HEX$(aba(mchr))
        fieldsep = INSTR(magacc$, "=")
        IF fieldsep = 0 THEN fieldsep = 19
        magmatch$ = MID$(magacc$, 2, fieldsep - 2)
        LOCATE mswy + 10, mswx + 12: PRINT magmatch$;
        'PRINT MID$(magacc$, 2, 19);
        LOCATE 40, 25: PRINT magacc$;
        '
magfini:
        RETURN
magerr:
        LOCATE mswy + 10, mswx + 12: PRINT "ERROR";
        GOTO magfini
magnd:
        LOCATE mswy + 10, mswx + 12: PRINT "No data";
        GOTO magfini
        '----------------------------------------
END SUB SUB ccwembosser
SHARED motorporta, motorportb, motorportc, motorportr, motormode, motorsoff
SHARED mcardf, mcardr, minsertf, minsertr, mfeed, mform, mflipf, mflipr
SHARED mcards, minserts, mfeeds, mforms, mflips, mspin, mejectf, mejectr
SHARED mburst, mxfer, mspins, mejects, mbursts, mxfers, feedbrk, burstbrk
SHARED snsporta, snsportb, snsportc, snsportr, snsmode, snscardl, snscardr
SHARED snsinsert, snscardp, snspicker, snsfold, snsform, snsspin, snsoutput
SHARED snsreject, snsburst, snsexit, snsflipdn, snsoutdn, snsrotate
SHARED dataporta, dataportb, dataportc, dataportr, datamode, formwasdo
```

Veripro

```
ne
SHARED ppstatus, procescmd, proceserr$, pppline, psfftime
SHARED eformat$           'embosser line location format
SHARED t()                'format aray
SHARED mswy, mswx, mbosscmd, mbossstatus, crn, ern, newlineloc, autoem
b, autostate
SHARED lineloc$, mbosserr$, abcd$ '
        '
        '-------- NBS advantage embosser --------
        '
        '
        LOCATE mswy + 7, mswx + 12: PRINT SPACE$(19);
fimabegin:
        IF autoemb = 1 THEN EXIT SUB
        IF INP(snsportb) AND snscardp THEN
                GOTO embgo
          ELSE
                mbosserr$ = "Card waiting."
                EXIT SUB
        END IF
embgo:
        IF crn > ern THEN
                mbossstatus = -1
                mbosserr$ = "End of file."
                EXIT SUB
        END IF
        mbossstatus = 1: autoemb = 1
        IF newlineloc = 1 THEN GOSUB fimaffselect
        newlineloc = 0
        '
fimaloop:
        GET #1, crn
        IF EOF(1) = -1 THEN GOTO fimafini
        a$ = abcd$
        LOCATE mswy + 2, mswx + 18: PRINT SPACE$(9)
        LOCATE mswy + 2, mswx + 18: PRINT crn;
        filtercardacc$ = MID$(a$, t(5), (t(6) - t(5)) + 1)
        matchcardacc$ = ""
        FOR rp = 1 TO LEN(filtercardacc$)
        IF MID$(filtercardacc$, rp, 1) <> " " THEN
                matchcardacc$ = matchcardacc$ + MID$(filtercardacc$, r
p, 1)
        END IF
        NEXT rp
        LOCATE mswy + 7, mswx + 12: PRINT matchcardacc$;
        'LOCATE 37, 1: PRINT a$;
```

Page 46

Veripro

```
        FOR rp = 5 TO (t(3) * 4) + 1 STEP 4
        IF t(rp + 2) = 0 THEN
MID$(lcard(t(rp + 3) + 9), 1) = MID$(a$, t(rp), (t(rp + 1) - t(rp)) +
1)
        ELSE
MID$(lcard(t(rp + 2)), t(rp + 3)) = MID$(a$, t(rp), (t(rp + 1) - t(rp
)) + 1)
        END IF
        NEXT rp
'
'
fimaselect:
        PRINT #3, CHR$(4); "31"; CHR$(5);
fimaswait:
        GOSUB fimaintr
        IF LOC(3) = 0 THEN GOTO fimaswait
        GOSUB incoming
        IF MID$(responce$, 1, 1) = CHR$(6) THEN GOTO fimadata
        GOTO fimaselect
'
fimadata:
        magrow = 0
        currentcrn$ = LTRIM$(RTRIM$(STR$(crn)))
        crnout$ = STRING$(6 - LEN(currentcrn$), 48) + currentcrn$
        PRINT #3, CHR$(1); "31"; CHR$(2); "T]09N]"; crnout$; CHR$(13);
        FOR rp = 1 TO 12
        IF LEN(RTRIM$(MID$(lcard(rp), 1, 240))) > 0 THEN
                        IF rp > 9 AND magrow = 0 THEN
                                PRINT #3, "[";
                                magrow = 1
                        END IF
                        IF rp = 10 THEN PRINT #3, "%";
                        IF rp = 11 THEN PRINT #3, ";";
                        IF rp = 12 THEN PRINT #3, "_;";
                IF rp < 10 THEN
                        PRINT #3, RTRIM$(MID$(lcard(rp), 1, 240));
                ELSE
                        magxmit$ = ""
                        magfix$ = RTRIM$(MID$(lcard(rp), 1, 240))
                        FOR mmfix = 1 TO LEN(magfix$)
                                IF MID$(magfix$, mmfix, 1) <> " " THEN
                                        magxmit$ = magxmit$ + MID$(mag
fix$, mmfix, 1)
                                END IF
                        NEXT mmfix
                        PRINT #3, magxmit$;
                END IF
```

Page 47

Veripro

```
                        IF rp < 10 THEN PRINT #3, CHR$(13);
                        IF rp > 9 THEN PRINT #3, "?";
                END IF
                NEXT rp
                PRINT #3, CHR$(3);
                '
fimadwait:
                GOSUB fimaintr
                IF LOC(3) = 0 THEN GOTO fimadwait
                GOSUB incoming
                IF MID$(responce$, 1, 1) = CHR$(6) THEN GOTO fimafini
                '
                'add options hear for no repeat xmition on error
                IF MID$(responce$, 2, (LEN(responce$) - 2)) = "FORMNULL" THEN
                        GOSUB fimaffselect
                END IF
                '
                GOTO fimaselect
                '
fimafini:
                mbossstatus = 0
                mbosserr$ = "Card ready"
                EXIT SUB
                '
                '
                '---------------------Fima subs
incoming:
                Start = TIMER
                DO WHILE TIMER < Start + .5: LOOP
                responce$ = INPUT$(LOC(3), #3)
                '
                LOCATE 35, 50: PRINT SPACE$(32);
                LOCATE 35, 50
                FOR rp = 1 TO LEN(responce$)
                        '
                        IF MID$(responce$, rp, 1) = CHR$(3) THEN PRINT "<ETX>";
                        IF MID$(responce$, rp, 1) = CHR$(4) THEN PRINT "<EOT>";
                        IF MID$(responce$, rp, 1) = CHR$(5) THEN PRINT "<ENQ>";
                        IF MID$(responce$, rp, 1) = CHR$(6) THEN PRINT "<ACK>";
                        IF MID$(responce$, rp, 1) = CHR$(13) THEN PRINT "<CR>";
                        IF MID$(responce$, rp, 1) = CHR$(10) THEN PRINT "<LF>";
                        '
```

Page 48

```
                            Veripro
              IF ASC(MID$(responce$, rp, 1)) > 31 THEN
                      PRINT MID$(responce$, rp, 1);
              END IF
       NEXT rp
       RETURN
       '
       '-------------------------------Send Card Format
fimaffselect:
       PRINT #3, CHR$(4); "31"; CHR$(5);
fimaffwait:
       GOSUB fimaintr
       IF LOC(3) = 0 THEN GOTO fimaffwait
       GOSUB incoming
       IF MID$(responce$, 1, 1) = CHR$(6) THEN GOTO sendformat
       GOTO fimaffselect
sendformat:
       PRINT #3, CHR$(1); "31"; CHR$(2); "F]"; lineloc$; CHR$(3);
formatwait:
       GOSUB fimaintr
       IF LOC(3) = 0 THEN GOTO formatwait
       GOSUB incoming
       IF MID$(responce$, 1, 1) = CHR$(6) THEN RETURN
       '
       GOTO sendformat
       '
fimaintr:
       opp$ = INKEY$
       IF UCASE$(opp$) = "S" THEN
              fimastop = 1
              GOTO fimafini
       END IF
       RETURN
       '
       '
       '
END SUB SUB ccwmatch
SHARED motorporta, motorportb, motorportc, motorportr, motormode, moto
rsoff
SHARED mcardf, mcardr, minsertf, minsertr, mfeed, mform, mflipf, mflip
r
SHARED mcards, minserts, mfeeds, mforms, mflips, mspin, mejectf, mejec
tr
SHARED mburst, mxfer, mspins, mejects, mbursts, mxfers, feedbrk, burst
brk
SHARED snsporta, snsportb, snsportc, snsportr, snsmode, snscardl, snsc
ardr
```

```
                              Veripro
SHARED snsinsert, snscardp, snspicker, snsfold, snsform, snsspin, snso
utput
SHARED snsreject, snsburst, snsexit, snsflipdn, snsoutdn, snsrotate
SHARED dataporta, dataportb, dataportc, dataportr, datamode, autoemb,
autostate
SHARED mswy, mswx, matchcmd, matchstatus, mtchpline, matcherr$
SHARED psfftime
        '
        'ccw-match.bas
        'match data strings and insert controller
        '
        'enter with    matchcmd = 0 get status
        '                         1 match and insert
        '                         2 match but do not insert
        '                         3 force insert
        '
        'return with matchstatus = 0 ready
        '                          1 match insert ok
        '                          2 match only ok
        '                          3 match error
        '                          4 insert jam
        '
        '       ???????$ = ascii account number - disk file
        '       ???????$ = ascii account number - printed
        '       ???????$ = ascii account number - embosser
        '       ???????$ = ascii account number - encoded
        '       matcherr$ = match error message
        '
        '------------------------
        '
        IF matchcmd = 0 GOTO getmstat
        IF matchcmd = 1 THEN
                IF mtchpline = 0 GOTO matchit
        END IF
        IF matchcmd = 2 THEN
                IF mtchpline = 0 GOTO iputit
        END IF
        EXIT SUB
        '
        '------------------------
        '---------- get status ---
        '------------------------
getmstat:
        IF mpstate = 1 THEN EXIT SUB
        IF merrorstat = 1 THEN
                matchstatus = 3
                EXIT SUB
```

Veripro

```
            END IF
            IF merrorstat = 0 THEN
                    matchstatus = 0
                    EXIT SUB
            END IF
            EXIT SUB
            '
            '------------------------
            '---- match and insert ---
            '------------------------
matchit:
            'match data fields hear
            '
            matchstatus = 1
            timeout = TIMER + 2
putcard:
            IF INP(snsportb) AND snsinsert THEN
                    GOSUB insfw
            ELSE
                    GOSUB insstop
                    matchstatus = 3
                    mtchpline = 0
                    mtcherr$ = "Insert sensor"
                    EXIT SUB
            END IF
iput1:
            IF INP(snsportb) AND snsinsert THEN
                    IF TIMER < timeout THEN
                            GOTO iput1
                    ELSE
                            GOSUB insstop
                            matchstatus = 3
                            mtchpline = 0
                            mtcherr$ = "Inserter jam"
                            EXIT SUB
                    END IF
            END IF
iput2:
            IF INP(snsportb) AND snsinsert THEN
                    GOTO iputit
            ELSE
                    IF TIMER < timeout THEN
                            GOTO iput2
                    ELSE
                            GOSUB insstop
                            matchstatus = 3
                            mtchpline = 0
                            mtcherr$ = "Inserter jam"
```

Page 51

```
                        Veripro
                GOTO iput2
            END IF
        END IF
        '
iputit: GOSUB insrv
        '
iput3:
        IF INP(snsportb) AND snsinsert THEN
                IF TIMER < timeout THEN
                        GOTO iput3
                ELSE
                        GOSUB insstop
                        matchstatus = 3
                        mtchpline = 0
                        mtcherr$ = "Inserter jam"
                        EXIT SUB
                END IF
        END IF
iput4:
        IF INP(snsportb) AND snsinsert THEN
                GOTO putdone
        ELSE
                IF TIMER < timeout THEN
                        GOTO iput4
                ELSE
                        GOSUB insstop
                        matchstatus = 3
                        mtchpline = 0
                        mtcherr$ = "Inserter jam"
                        EXIT SUB
                END IF
        END IF
putdone:
        GOSUB insstop
        matchstatus = 0
        mtchpline = 0
        autoemb = 0
        GOTO insfini
        '
        '------------
        '--- subs ---
insfw:
        motordb = INP(motorporta)
        motordb = motordb OR minserts
        motordb = motordb AND minsertf
        OUT motorporta, motordb
        RETURN
insrv:
```

Page 52

```
                              Veripro
        motordb = INP(motorporta)
        motordb = motordb OR minserts
        motordb = motordb AND minsertr
        OUT motorporta, motordb
        RETURN
insstop:
        motordb = INP(motorporta)
        motordb = motordb OR minserts
        OUT motorporta, motordb
        RETURN
        '
        '-----------------------------
insfini:
END SUB SUB ccwprinter
SHARED motorporta, motorportb, motorportc, motorportr, motormode, motorsoff
SHARED mcardf, mcardr, minsertf, minsertr, mfeed, mform, mflipf, mflipr
SHARED mcards, minserts, mfeeds, mforms, mflips, mspin, mejectf, mejectr
SHARED mburst, mxfer, mspins, mejects, mbursts, mxfers, feedbrk, burstbrk
SHARED snsporta, snsportb, snsportc, snsportr, snsmode, snscardl, snscardr
SHARED snsinsert, snscardp, snspicker, snsfold, snsform, snsspin, snsoutput
SHARED snsreject, snsburst, snsexit, snsflipdn, snsoutdn, snsrotate
SHARED amtbc$                   'printer bar code type
SHARED tprn()                   'format aray
SHARED bcemu$, bcsetup$, bccmd$, bcend$
SHARED mswy, mswx, amtcmd, amtstatus, crn, ern, formwasdone, autolpt
SHARED amterr$, abcd$, figca$
SHARED psfftime, autostate, pageup, remoteexit '
        IF MID$(UCASE$(figca$), 1, 4) = "LPT1" THEN lptport = &H3BC
        IF MID$(UCASE$(figca$), 1, 4) = "LPT2" THEN lptport = &H378
        '
        '----------- AMT-535 printer driver ---------
        '----- (mode = epsion lq2550 bc option) -----
        '
        bcemu$ = CHR$(27) + CHR$(27) + "E" + CHR$(14)
        bcsetup$ = CHR$(27) + "[0;4;0;1;3;3;5;2}"
        bccmd$ = CHR$(27) + "[4t"
        bcend$ = CHR$(27) + "[0t"
        '
```

Page 53

```
                            Veripro
amtbegin:
        IF autolpt = 0 GOTO amttest2
        IF autolpt = 1 GOTO toburst
        IF autolpt > 1 THEN EXIT SUB '
amttest2:
        lpttest = INP(lptport + 1)
        IF lpttest AND &H8 THEN
                GOTO amttest3
        ELSE
                amtstatus = -1
                amterr$ = "Printer fault."
                EXIT SUB
        END IF
amttest3:
        lpttest = INP(lptport + 1)
        IF lpttest AND &H20 THEN
                amtstatus = -1
                amterr$ = "Out of papper."
                EXIT SUB
        END IF
amttest4:
        IF crn > ern THEN
                amtstatus = -1
                amterr$ = "End of file."
                EXIT SUB
        END IF
amttest5:
        IF INP(snsportb) AND snsfeed THEN
                amtstatus = -1
                amterr$ = "Check burst station."
                EXIT SUB
        END IF
amttest6:
        IF formwasdone > 0 THEN
                amtstatus = -1
                amterr$ = "Check module for form."
                EXIT SUB
        END IF
amttest7:
        IF INP(snsportc) AND snsburst THEN
                amtstatus = -1
                amterr$ = "Check burst home."
                EXIT SUB
        END IF
        '--------------------
        '---- good to go ----
```

Page 54

```
                          Veripro
        '------------------
        amtstatus = 1
amtloop:
        GET #1, crn
        IF EOF(1) = -1 THEN GOTO amtfini
        amt$ = abcd$
        vpos = 1: cpf = 1
        LOCATE mswy + 2, mswx + 18: PRINT SPACE$(9)
        LOCATE mswy + 2, mswx + 18: PRINT crn;
        filterformacc$ = MID$(a$, tprn(5), (tprn(6) - tprn(5)) + 1)
        matchformacc$ = ""
        FOR rp = 1 TO LEN(filterformacc$)
        IF MID$(filterformacc$, rp, 1) <> " " THEN
                matchformacc$ = matchformacc$ + MID$(filterformacc$, r
p, 1)
        END IF
        NEXT rp
        LOCATE mswy + 7, mswx + 12: PRINT matchformacc$;
        '
        '--- the driver ---
        '
         FOR rp = 5 TO (tprn(3) * 4) + 1 STEP 4
            IF vpos = 1 THEN GOTO donsda
        '
        MID$(lform(tprn(rp + 2)), tprn(rp + 3)) = MID$(amt$, tprn(rp)
, (tprn(rp + 1) - tprn(rp)) + 1)
        '
donsda:    IF vpos = 0 THEN GOTO 1223
           vpos = 0
           acnt$ = MID$(amt$, tprn(rp), (tprn(rp + 1) - tprn(rp)) +
1)
           crntemp = crn
           '
1221       IF crn + 1 > ern GOTO 1222
           '
           GET #1, crn + 1
           IF EOF(1) = -1 THEN GOTO 1222
           nacnt$ = MID$(abcd$, tprn(rp), (tprn(rp + 1) - tprn(rp))
+ 1)
           IF acnt$ <> nacnt$ THEN GOTO 1222
           cpf = cpf + 1
           crn = crn + 1
           IF crn < ern GOTO 1221
           IF cpf < 4 GOTO 1221
           '
1222       cpf$ = STR$(cpf)
           cpf$ = MID$(cpf$, 2, 1)
           bcdata$ = cpf$ + acnt$
```

Veripro

```
            bcprint$ = ""
            FOR bcrp = 1 TO LEN(bcdata$)
                IF MID$(bcdata$, bcrp, 1) <> " " THEN bcprint$ = bcpri
nt$ + MID$(bcdata$, bcrp, 1)
            NEXT bcrp
            MID$(lform(tprn(rp + 2) + 1), tprn(rp + 3) - 1) = bccmd$
+ bcprint$ + bcend$
1223    NEXT rp
        '
        lastrow = 63: GOSUB printmem
        '
amtfini:
        autolpt = 1
        amtstatus = 0
        amterr$ = "Form ready"
        formwasdone = 1
        EXIT SUB
        '
toburst:
        IF INP(snsportb) AND snsform THEN EXIT SUB
        GOSUB tkuptst
        pageup = 1: autolpt = 2
        EXIT SUB
        '
        '----------------------------
        '-------- subs --------------
        '----------------------------
        '
        'Print form from memory
        '
printmem:
sendit:
        PRINT #4, bcemu$ + bcsetup$;
        FOR rp = 1 TO lastrow
                PRINT #4, RTRIM$(MID$(lform(rp), 1, 80))
        NEXT rp
        RETURN
        '
        '--------------------
        'test sub for moving form up 24 lines and down 34 lines
        '
tkuptst:
        'tab head to right of center
        PRINT #4, CHR$(27) + CHR$(68) + CHR$(34) + CHR$(0);
        PRINT #4, CHR$(9) + ".";
        '
        'move form up n lines to sensor
        GOSUB ssfeedon
```

```
                            Veripro
        FOR uprp = 1 TO 50
                PRINT #4,
        NEXT uprp
        '
        'change line spaceing to 1/60
        PRINT #4, CHR$(27) + CHR$(65) + CHR$(1);
tkupll:
        'wait for form to hit feed sensor
        IF INP(snsportb) AND snsform THEN GOTO tkupll
tkupyy:
        'move form till feed hole at feed sensor
                IF remoteexit = 0 THEN
                        IF INP(snsportc) AND snsexit THEN
                                remoteexit = 0
                        ELSE
                                remoteexit = 1
                        END IF
                END IF
        IF INP(snsportb) AND snsform THEN
                GOTO tkupstop
        ELSE
                GOSUB ssfeedon
                FOR tkstalls = 1 TO 200
                        IF INP(snsportb) AND snsform THEN GOTO tkupstop
                NEXT tkstalls
                PRINT #4,
                FOR tkstall = 1 TO 600
                        IF INP(snsportb) AND snsform THEN GOTO tkupstop
                NEXT tkstall
                GOSUB ssfeedoff
                FOR tkstalls = 1 TO 200
                        IF INP(snsportb) AND snsform THEN GOTO tkupstop
                NEXT tkstalls
                GOTO tkupyy
        END IF
        '
tkupstop: 'stop the form - ready for burst
        GOSUB ssfbreak
        GOSUB ssfeedoff
        PRINT #4, CHR$(27) + "2";
        RETURN
        '--------------------
ssfeedon:
        motordb = INP(motorporta)
        motordb = motordb OR mfeeds Page 57
```

Veripro

```
        motordb = motordb AND mfeed
        OUT motorporta, motordb
        RETURN
        '
ssfeedoff:
        motordb = INP(motorporta)
        motordb = motordb OR mfeeds
        OUT motorporta, motordb
        RETURN
        '
ssfbreak:
        motordb = INP(motorportb)
        motordb = motordb AND feedbrk
        OUT motorportb, motordb
        '
        fbreakon = TIMER + .3
        DO WHILE TIMER < fbreakon: LOOP
        '
        motordb = INP(motorportb)
        motordb = motordb OR &H40
        OUT motorportb, motordb
        '
        RETURN
        '
        '-----------------------------Get Bar Code type
        '
        IF is$ = " Interleaved 2 of 5 " THEN bcp1$ = "0"
        IF is$ = " Code 3 of 9        " THEN bcp1$ = "4"
        IF is$ = " Codabar            " THEN bcp1$ = "9"
        bcemu$ = CHR$(27) + CHR$(27) + "E" + CHR$(14)
        bcsetup$ = CHR$(27) + "[" + bcp1$ + ";4;0;1;3;2;4;2}"
        bccmd$ = CHR$(27) + "[4t"
        bcend$ = CHR$(27) + "[0t"
        '
'------
END SUB SUB ccwproces
SHARED motorporta, motorportb, motorportc, motorportr, motormode, motorsoff
SHARED mcardf, mcardr, minsertf, minsertr, mfeed, mform, mflipf, mflipr
SHARED mcards, minserts, mfeeds, mforms, mflips, mspin, mejectf, mejectr
SHARED mburst, mxfer, mspins, mejects, mbursts, mxfers, feedbrk, burstbrk
SHARED snsporta, snsportb, snsportc, snsportr, snsmode, snscardl, snscardr
```

Page 58

```
                            Veripro
SHARED snsinsert, snscardp, snspicker, snsfold, snsform, snsspin, snso
utput
SHARED snsreject, snsburst, snsexit, snsflipdn, snsoutdn, snsrotate
SHARED dataporta, dataportb, dataportc, dataportr, datamode, formwasdo
ne
SHARED mswy, mswx, ppstatus, procescmd, proceserr$, pppline, psfftime
SHARED autoemb, autolpt, autostate, remotexdone '
        'ccw-proces.bas
        'proces card and form controller
        '
        'enter with    procescmd = 0 get status
        '                          1 start proces
        '                          2 stop proces
        '
        'return with   ppstatus = 0 ready
        '                         1 feed & form running
        '                         2 flip running
        '                         3 spin running
        '                         4 output running
        '                         5 error
        '         proceserr$ = proces error message
        '
        '------------------------
        '
        IF procescmd = 0 GOTO getppstat
        IF procescmd = 1 THEN
                IF pppline = 0 GOTO procesit
                IF pppline = 1 GOTO pploop1
                IF pppline = 4 GOTO pploop4
                IF pppline = 5 GOTO pploop5
                IF pppline = 6 GOTO pploop6
                IF pppline = 7 GOTO pploop7
                IF pppline = 8 GOTO pploop8
        END IF
        IF procescmd = 2 THEN
                IF procespline = 0 GOTO pppanic
        END IF
        EXIT SUB
        '
        '------------------------
        '---------- get status ---
        '------------------------
getppstat:
        EXIT SUB
        '
```

Page 59

```
                              Veripro
          '--------------------------
          '-- process card and form --
          '--------------------------
procesit:
          ppstatus = 1: pppline = 1
pploop1:                                              'check p2
          IF INP(snsportb) AND snscardl THEN
                  GOTO pploop2
          ELSE
                  ppstatus = -5
                  proceserr$ = "Insert fail (right)"
                  GOTO pperror
          END IF
pploop2:                                              'check p1
          IF INP(snsportb) AND snscardr THEN
                  GOTO pploop3
          ELSE
                  ppstatus = -5
                  proceserr$ = "Insert fail (left)"
                  GOTO pperror
          END IF
          '--------------------
pploop3:
          psfftime = TIMER + 3.2
          GOSUB ppfandfon                             'start feed &
form
          ppstatus = 1: pppline = 4
pploop4:
          IF TIMER < psfftime THEN
                  EXIT SUB                    'exit loop running
          END IF
          GOSUB ppfandfoff                            'stop feed & f
orm
          '--------------------
          autolpt = 0
          formwasdone = 0
          ppstatus = 2: pppline = 5
          psfftime = TIMER + 6
          GOSUB ppflipfw                              'start flip fo
rward
pploop5:
pploopa5:
          IF INP(snsportc) AND snsflipdn THEN
                  IF TIMER > psfftime THEN
                          GOSUB ppflipstop
                          ppstatus = -5
                          proceserr$ = "Flip fail"
                          GOTO pperror
                                Page 60
```

Veripro

```
            ELSE
                    EXIT SUB                     'exit loop runing
                    'GOTO pploopa5
            END IF
        END IF
'
        GOSUB ppfliprev                                  'start flip ba
ck
        psfftime = TIMER + 6
pploopb5:
        IF INP(snsportb) AND snsfold THEN
        GOSUB ppfliprev                                  'start flip ba
ck
                IF TIMER > psfftime THEN
                        GOSUB ppflipstop
                        ppstatus = -6
                        procserr$ = "Flip fail"
                        GOTO pperror
                ELSE
                        'exit loop runing
                        GOTO pploopb5
                END IF
        END IF
        GOSUB ppflipstop                                 'stop flipper
'
'--------------------
        ppstatus = 3: pppline = 6
        psfftime = TIMER + 3
        GOSUB ppspinon                                   'start spiner
pploop6:
pploopa6:
        IF INP(snsportb) AND snsspin THEN
                IF TIMER > psfftime THEN
                        ppstatus = -7
                        procserr$ = "Spin fail"
                        GOTO pperror
                ELSE
                        EXIT SUB                     'exit loop runing
                        GOTO pploopa6
                END IF
        END IF
        GOSUB ppspinoff                                  'stop spiner
        IF INP(snsportc) AND snsrotate THEN              'rotate done
                ppstatus = -8
                procserr$ = "Rotate fail"
                GOTO pperror
        END IF
'
```

Page 61

```
                            Veripro
        '--------------------
        ppstatus = 4: pppline = 7
        psfftime = TIMER + 3
        GOSUB ppoutfw                           'start output
forward
pploop7:
pploopa7:
        IF INP(snsportc) AND snsoutdn THEN
                IF TIMER > psfftime THEN
                        '
                        GOSUB ppoutrev          'start output
 rev
                        ostpo = TIMER + 1
                        DO WHILE TIMER < ostpo: LOOP
                        '
                        GOSUB ppoutstop
                        ppstatus = -9
                        proceserr$ = "Output fail"
                        GOTO pperror
                ELSE
                        EXIT SUB                'exit loop runing
                        'GOTO pploopa7
                END IF
        END IF
        '----------pitty
        '
        ptit = TIMER + 1
        pittney = INP(motorportb)
        pittney = pittney AND &HDF              'set request l
ow
        OUT motorportb, pittney
        '
pitloop:
        IF INP(snsportc) AND &H80 THEN
                IF TIMER > ptit THEN
                        pittney = INP(motorportb)
                        pittney = pittney OR &H20    'set request h
igh
                        OUT motorportb, pittney
                        ppstatus = -10
                        proceserr$ = "Stuffer request fail"
                        GOSUB ppoutrev              'start output
rev
                        GOTO pperror
                ELSE
                        GOTO pitloop
                END IF
        END IF
```

Page 62

```
                            Veripro
        pittney = INP(motorportb)
        pittney = pittney OR &H20                   'set request h
igh
        OUT motorportb, pittney
        '
        '----------pitty
        GOSUB ppxferon                              'start xfer
        outfuge = TIMER + .4
        DO WHILE outfuge > TIMER: LOOP
        '
        GOSUB ppoutrev                              'start output
rev
        psfftime = TIMER + 3
pploopb7:
        IF INP(snsportc) AND snsoutput THEN
                IF TIMER > psfftime THEN
                        GOSUB ppoutstop
                        ppstatus = -11
                        proceserr$ = "Output fail"
                        GOTO pperror
                ELSE
                        'exit loop runing
                        GOTO pploopb7
                END IF
        END IF
        GOSUB ppoutstop                             'stop output
        '
        '-------------------
        '
        '
        '------------------
        ppstatus = 5: pppline = 8
        psfftime = TIMER + 8
pploop8:
pploopa8:
        IF remoteexit = 1 THEN
                remoteexit = 0
                GOTO remotexdone
        END IF
        IF INP(snsportc) AND snsexit THEN
                IF TIMER > psfftime THEN
                        GOSUB ppxferoff
                        ppstatus = -11
                        proceserr$ = "Xfer fail"
                        GOTO pperror
                ELSE
                        EXIT SUB                    'exit loop runing
                        'GOTO pploopa8
                            Page 63
```

```
                                            Veripro
                END IF
        END IF
remotexdone:
        psfftime = TIMER + 8
pploopb8:
        IF INP(snsportc) AND snsexit THEN
                pitfuge = TIMER + .5
                DO WHILE pitfuge > TIMER
                LOOP
                'GOSUB ppxferoff
                GOTO pploop9
        ELSE
                IF TIMER > psfftime THEN
                        GOSUB ppxferoff
                        ppstatus = -12
                        procerr$ = "Stuffer fail"
                        GOTO pperror
                END IF
        END IF
        GOTO pploopb8
        '
        '--------------------
pploop9:
        ppstatus = 0
        pppline = 0
        procerr$ = ""
        EXIT SUB
        '
        '----------------
        '-- error exit --
        '----------------
pperror:
        GOSUB pppanic
        pppline = 0
        EXIT SUB
        '-------------------------------
pppanic:
        GOSUB ppfandfoff
        GOSUB ppflipstop
        GOSUB ppspinoff
        GOSUB ppoutstop
        GOSUB ppxferoff
        ppstate = 0
        EXIT SUB
        '-------------------------------
        '-------- subs -----------------
        '-------------------------------
ppfandfon:

Page 64
```

```
                                        Veripro
        motordb = INP(motorporta)
        motordb = motordb OR mfeeds
        motordb = motordb OR mforms
        motordb = motordb AND mfeed
        motordb = motordb AND mform
        OUT motorporta, motordb
        RETURN
        '
ppfandfoff:
        motordb = INP(motorporta)
        motordb = motordb OR mfeeds
        motordb = motordb OR mforms
        OUT motorporta, motordb
        RETURN
        '
ppflipfw:
        motordb = INP(motorporta)
        motordb = motordb OR mflips
        motordb = motordb AND mflipf
        OUT motorporta, motordb
        RETURN
        '
ppfliprev:
        motordb = INP(motorporta)
        motordb = motordb OR mflips
        motordb = motordb AND mflipr
        OUT motorporta, motordb
        RETURN
        '
ppflipstop:
        motordb = INP(motorporta)
        motordb = motordb OR mflips
        OUT motorporta, motordb
        RETURN
        '
ppspinon:
        motordb = INP(motorportb)
        motordb = motordb OR mspins
        motordb = motordb AND mspin
        OUT motorportb, motordb
        RETURN
        '
ppspinoff:
        motordb = INP(motorportb)
        motordb = motordb OR mspins
        OUT motorportb, motordb
        RETURN
        '
```

Page 65

```
                              Veripro
ppoutfw:
        motordb = INP(motorportb)
        motordb = motordb OR mejects
        motordb = motordb AND mejectf
        OUT motorportb, motordb
        RETURN
        '
ppoutrev:
        motordb = INP(motorportb)
        motordb = motordb OR mejects
        motordb = motordb AND mejectr
        OUT motorportb, motordb
        RETURN
        '
ppoutstop:
        motordb = INP(motorportb)
        motordb = motordb OR mejects
        OUT motorportb, motordb
        RETURN
        '
ppxferon:
        motordb = INP(motorportb)
        motordb = motordb OR mxfers
        motordb = motordb AND mxfer
        OUT motorportb, motordb
        RETURN
        '
ppxferoff:
        motordb = INP(motorportb)
        motordb = motordb OR mxfers
        OUT motorportb, motordb
        RETURN
        '
        '----------------------------
ppfini:
END SUB SUB pkfile
SHARED pathname$, inam$
        '
        DIM fxnam$(250)
        wfg = 7: wbg = 1
        '
        pnam$ = pathname$
        fdisplay = 10
        GOSUB delfil
        '
        pathnam$ = pnam$ + "\" + inam$ Page 66
```

Veripro

```
                GOTO fini
                '
                '---------------------------------------- Pick a file
delfil:
                wy = 14: wx = 42: WH = 21: WW = 38
                ddd = wy + 4: DDP = 0: flnam = ddd
                '
pick:           fxn = 1
                '
                pass$ = "dir " + pnam$ + "\*.* | sort > dirfile"
                SHELL pass$
                '
                OPEN "dirfile" FOR INPUT AS #10
                '
                LINE INPUT #10, temp$
                LINE INPUT #10, temp$
                LINE INPUT #10, temp$
                LINE INPUT #10, temp$    '# files and space used
                LINE INPUT #10, temp$    'disk drive label
                LINE INPUT #10, temp$    'sub-directory first dot
                LINE INPUT #10, temp$    'sub-directory second dot
                LINE INPUT #10, temp$    'subdir .
                LINE INPUT #10, temp$    'subdir ..
                '
delfa:          LINE INPUT #10, temp$
                fxnam$(fxn) = LEFT$(temp$, 31)
                fxn = fxn + 1
                IF EOF(10) = -1 THEN GOTO delfb ELSE GOTO delfa
                '
delfb:          CLOSE #10
                KILL "dirfile"
                fxntot = fxn - 1
                '
                fxn = 1: GOSUB ddlst
                dline = 1: GOSUB dpon
                '
delfc:          xx$ = INKEY$
                IF xx$ = CHR$(27) THEN GOTO delfz
                IF LEN(xx$) = 2 AND MID$(xx$, 2, 1) = CHR$(72) THEN GOSUB dpoi
nt
                IF LEN(xx$) = 2 AND MID$(xx$, 2, 1) = CHR$(72) THEN GOTO delfc
                IF LEN(xx$) = 2 AND MID$(xx$, 2, 1) = CHR$(80) THEN GOSUB dpoi
nt
                IF LEN(xx$) = 2 AND MID$(xx$, 2, 1) = CHR$(80) THEN GOTO delfc
                IF xx$ = CHR$(13) AND MID$(xxxnam$, 1, 1) <> "." THEN GOTO del
xxx
                IF LEN(xx$) <> 0 THEN SOUND 1000, 1: SOUND 500, 1
                GOTO delfc
```

Page 67

```
                              Veripro
        '
delfz:  inam$ = ""
        RETURN
        '
ddlst:  COLOR wfg, wbg
        IF fxntot > fdisplay THEN fxtmp = fxn + (fdisplay - 1) ELSE fx
tmp = fxntot
        FOR DFG = fxn TO fxtmp
         LOCATE ddd, wx + 2: PRINT " " + fxnam$(DFG) + " ";
         ddd = ddd + 1
        NEXT DFG
        ddd = wy + 4
        RETURN
        '
dpoint: IF MID$(xx$, 2, 1) = CHR$(80) AND dline = fxntot THEN GOTO dpo
er
        IF MID$(xx$, 2, 1) = CHR$(72) AND dline < 2 THEN GOTO dpoer
        IF MID$(xx$, 2, 1) = CHR$(80) THEN
                GOSUB dpoff
                dline = dline + 1: flnam = flnam + 1
                IF flnam > ddd + (fdisplay - 1) THEN
                        flnam = flnam - 1: fxn = fxn + 1
                        GOSUB ddlst
                END IF
                GOSUB dpon
        END IF
        IF MID$(xx$, 2, 1) = CHR$(72) THEN
                GOSUB dpoff
                dline = dline - 1: flnam = flnam - 1
                IF flnam < ddd THEN
                        flnam = flnam + 1: fxn = fxn - 1
                        GOSUB ddlst
                END IF
                GOSUB dpon
        END IF
        RETURN
        '
dpon:   LOCATE flnam, wx + 2: COLOR wbg, wfg: PRINT " "; : PRINT fxnam
$(dline); : PRINT " ";
        xxxnam$ = RTRIM$(LEFT$(fxnam$(dline), 8)) + "."
        xxxnam$ = xxxnam$ + RTRIM$(MID$(fxnam$(dline), 10, 3))
        COLOR wfg, wgb
        RETURN
        '
dpoff:  LOCATE flnam, wx + 2: COLOR wfg, wbg: PRINT " "; : PRINT fxnam
$(dline); : PRINT " ";
        RETURN
        '
```

```
                                        Veripro
dpoer:  SOUND 1000, 1: SOUND 500, 1
        RETURN
        '
delxxx:
        inam$ = xxxnam$
        RETURN
        '
        '--------------------------------------------------------------
        '
fini:
END SUB SUB pkformat
SHARED t(), aam$
        '
        'Pick a format
        '
        DIM fxnam$(250)
        '
        GOSUB pkfmt
        GOTO sfini
        '
pkfmt:
        wfg = 7: wbg = 1
        wy = 14: wx = 53: WH = 21: WW = 18
        ddd = wy + 4: ddx = wy + 4: DDP = 0
        flnam = ddd: fxn = 1
        '
        OPEN "NFORMAT.dyn" FOR INPUT AS #2
        '
pklst:  INPUT #2, TNT
        FOR rp = 1 TO (TNT * 4) + 4
                INPUT #2, t(rp)
        NEXT rp
        INPUT #2, FID
        bam$ = INPUT$(FID, #2)
        '
        IF t(4) = 2 THEN
                fxnam$(fxn) = bam$
                fxn = fxn + 1
        END IF
        '
        IF EOF(2) = -1 THEN GOTO pelfb
        GOTO pklst
        '
pelfb:  CLOSE #2
        fxntot = fxn - 1
```

```
                            Veripro
        '
        fxn = 1: GOSUB pdlst
        dline = 1: GOSUB ppon
        '
pelfc:  xx$ = INKEY$
        IF xx$ = CHR$(27) THEN GOTO pelfz
        IF LEN(xx$) = 2 AND MID$(xx$, 2, 1) = CHR$(72) THEN GOSUB ppoi
nt
        IF LEN(xx$) = 2 AND MID$(xx$, 2, 1) = CHR$(72) THEN GOTO pelfc
        IF LEN(xx$) = 2 AND MID$(xx$, 2, 1) = CHR$(80) THEN GOSUB ppoi
nt
        IF LEN(xx$) = 2 AND MID$(xx$, 2, 1) = CHR$(80) THEN GOTO pelfc
        IF xx$ = CHR$(13) THEN GOTO pelxxx
        IF LEN(xx$) <> 0 THEN SOUND 1000, 1: SOUND 500, 1
        GOTO pelfc
        '
pelfz:  aam$ = ""        'esc exit
        RETURN
        '
pdlst:  COLOR wfg, wbg
        IF fxntot > 16 THEN fxtmp = fxn + 15 ELSE fxtmp = fxntot
        FOR DFG = fxn TO fxtmp
         LOCATE ddd, wx + 2: PRINT " "; fxnam$(DFG);
         PRINT SPACE$(12 - LEN(fxnam$(DFG)));
         ddd = ddd + 1
        NEXT DFG
        ddd = wy + 4
        RETURN
        '
ppoint: IF MID$(xx$, 2, 1) = CHR$(80) AND dline = fxntot THEN GOTO ppo
er
        IF MID$(xx$, 2, 1) = CHR$(72) AND dline < 2 THEN GOTO ppoer
        IF MID$(xx$, 2, 1) = CHR$(80) THEN
                GOSUB ppoff
                dline = dline + 1: flnam = flnam + 1
                IF flnam > ddd + 15 THEN
                        flnam = flnam - 1: fxn = fxn + 1
                        GOSUB pdlst
                END IF
                GOSUB ppon
        END IF
        IF MID$(xx$, 2, 1) = CHR$(72) THEN
                GOSUB ppoff
                dline = dline - 1: flnam = flnam - 1
                IF flnam < ddd THEN
                        flnam = flnam + 1: fxn = fxn - 1
                        GOSUB pdlst
                END IF
```

Page 70

Veripro

```
                GOSUB ppon
        END IF
        RETURN
        '
ppon:   LOCATE flnam, wx + 2: COLOR wbg, wfg
        PRINT " "; : PRINT fxnam$(dline);
        PRINT SPACE$(12 - LEN(fxnam$(dline)));
        xxxnam$ = RTRIM$(LEFT$(fxnam$(dline), 8))
        xxxnam$ = xxxnam$ + RTRIM$(MID$(fxnam$(dline), 10, 3))
        COLOR wfg, wbg
        RETURN
        '
ppoff:  LOCATE flnam, wx + 2: COLOR wfg, wbg
        PRINT " "; : PRINT fxnam$(dline);
        PRINT SPACE$(12 - LEN(fxnam$(dline)));
        RETURN
        '
ppoer:  SOUND 1000, 1: SOUND 500, 1
        RETURN
        '
pelxxx:
        aam$ = xxxnam$
        RETURN              'exit exit
        '
sfini:
END SUB
```

We claim:

1. A method of mounting cards to carriers, comprising the steps of:

reading card information from each of the cards;

sensing a code printed on the carriers;

automatically determining which of a plurality of different possible types of codes corresponds to the code sensed from each carrier;

decoding from each carrier the code in accordance with the type of code automatically determined to correspond to the code of each carrier to obtain carrier information;

comparing the card information from each card with the obtained carrier information to determine if there is a match;

rejecting cards which do not match the carrier information decoded from the carrier; and mounting cards to carriers which have carrier information decoded from said plurality of codes that matches the card information of the cards including the steps of storing a plurality of different subroutines for decoding a plurality of different types of codes, and automatically actuating a corresponding one of the plurality of different subroutines to decode the code read from the carrier form in response to automatic determination of which type a code is on the carrier form.

2. The method of claim 1 in which the plurality of different types of codes includes at least one of bar code, interleaved two of five code, interleaved three of nine code, Codabar UPC-A&E code, EAN-8 code, and EAN-13 code.

3. An embossed card package production system for mounting cards to carriers, comprising;

means for reading card information from each of the cards;

means for sensing a code printed on the carriers;

means for automatically determining which of a plurality of different possible types of codes corresponds to the code sensed from each carrier;

means for decoding from each carrier the code in accordance with the type of code automatically determined to correspond to the code of each carrier to obtain carrier information;

means for comparing the card information from each card with the obtained carrier information to determine if there is a match;

means for rejecting cards which do not match the carrier information decoded from the carrier; including means for mounting cards to carriers which have carrier information decoded from said plurality of codes that matches the card information of the cards, and means for storing a plurality of different subroutines for decoding a plurality of different types of codes, and means for automatically actuating a corresponding one of the plurality of different subroutines to decode the code read from the carrier form in response to automatic determination of which type a code is on the carrier form.

4. The embossed card package production system of claim 3 in which the plurality of different types of codes includes at least one of bar code, interleaved two of five code, interleaved three of nine code, Codabar UPC-A&E code, EAN-8 code, and EAN-13 code.

* * * * *